(12) United States Patent
Ting et al.

(10) Patent No.: US 11,052,149 B2
(45) Date of Patent: Jul. 6, 2021

(54) METHODS AND COMPOSITIONS FOR INDUCING AN IMMUNE RESPONSE

(71) Applicant: The University of North Carolina at Chapel Hill, Chapel Hill, NC (US)

(72) Inventors: Jenny P.-Y. Ting, Chapel Hill, NC (US); Robert Junkins, Durham, NC (US); Brandon Johnson, Durham, NC (US); Kristy Ainslie, Chapel Hill, NC (US); Eric Bachelder, Chapel Hill, NC (US); Matthew Gallovic, Carrboro, NC (US); Michael Collier, Durham, NC (US); Ning Cheng, Cary, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 16/334,153

(22) PCT Filed: Sep. 19, 2017

(86) PCT No.: PCT/US2017/052270
§ 371 (c)(1),
(2) Date: Mar. 18, 2019

(87) PCT Pub. No.: WO2018/053508
PCT Pub. Date: Mar. 22, 2018

(65) Prior Publication Data
US 2019/0275144 A1    Sep. 12, 2019

Related U.S. Application Data

(60) Provisional application No. 62/396,774, filed on Sep. 19, 2016.

(51) Int. Cl.
| | | |
|---|---|---|
| *A61K 39/39* | (2006.01) | |
| *A61K 39/145* | (2006.01) | |
| *A61P 31/16* | (2006.01) | |
| *A61P 35/00* | (2006.01) | |
| *A61P 37/04* | (2006.01) | |
| *C07K 16/28* | (2006.01) | |
| *A61K 39/00* | (2006.01) | |
| *A61K 31/7084* | (2006.01) | |
| *A61K 39/12* | (2006.01) | |
| *A61K 9/127* | (2006.01) | |
| *A61K 31/4745* | (2006.01) | |
| *A61K 9/16* | (2006.01) | |
| *A61P 25/28* | (2006.01) | |
| *A61K 9/00* | (2006.01) | |

(52) U.S. Cl.
CPC .......... *A61K 39/39* (2013.01); *A61K 9/0019* (2013.01); *A61K 9/1272* (2013.01); *A61K 9/1647* (2013.01); *A61K 31/4745* (2013.01); *A61K 31/7084* (2013.01); *A61K 39/0008* (2013.01); *A61K 39/0011* (2013.01); *A61K 39/12* (2013.01); *A61K 39/145* (2013.01); *A61P 25/28* (2018.01); *A61P 31/16* (2018.01); *A61P 35/00* (2018.01); *A61P 37/04* (2018.01); *C07K 16/2818* (2013.01); *C07K 16/2827* (2013.01); *A61K 2039/5154* (2013.01); *A61K 2039/55505* (2013.01); *A61K 2039/55555* (2013.01); *A61K 2039/55561* (2013.01); *A61K 2039/55566* (2013.01); *A61K 2039/55572* (2013.01); *A61K 2039/55577* (2013.01); *Y02A 50/30* (2018.01)

(58) Field of Classification Search
CPC .................. A61K 39/39; A61K 39/145; A61K 2039/55561; C07K 16/2827; A61P 31/16; A61P 37/04; A61P 35/00
USPC ......................................................... 514/44
See application file for complete search history.

(56) References Cited

U.S. PATENT DOCUMENTS

| | | | |
|---|---|---|---|
| 4,474,893 A | 10/1984 | Reading | |
| 4,676,980 A | 6/1987 | Segal et al. | |
| 4,816,567 A | 3/1989 | Cabilly et al. | |
| 2007/0081972 A1 | 4/2007 | Sandler et al. | |
| 2011/0229550 A1 | 9/2011 | Frechet et al. | |
| 2011/0262485 A1* | 10/2011 | Barber | |
| 2014/0205653 A1 | 7/2014 | Dubensky, Jr. et al. | |
| 2015/0056224 A1 | 2/2015 | Dubensky, Jr. et al. | |

FOREIGN PATENT DOCUMENTS

WO       2010005847       1/2010

OTHER PUBLICATIONS

Glossary of medical education terms, Institute of International Medical Education. http://www.iime.org/glossary.htm Accessed in Mar. 2013. (Year: 2013).*
Wu TYH. Strategies for designing synthetic immune agonists. Immunology, 148, 315-325, 2016. (Year: 2016).*
Corrales et al. Extremely potent immunotherapeutic activity of a STING agonist in the B16 melanoma model in vivo. Journal for ImmunoTherapy of Cancer 2013, 1(Suppl 1):O15. (Year: 2013).*
Duong et al. Electrospray Encapsulation of Toll-Like Receptor Agonist Resiquimod in Polymer Microparticles for the Treatment of Visceral Leishmaniasis. Mol. Pharmaceutics 2013, 10, 1045-1055. (Year: 2013).*
Almeria et al. "A multiplexed electrospray process for single-step synthesis of stabilized polymer particles for drug delivery" Journal of Controlled Release, 154(2):203-210 (2011) (Abstract only).
Bachelder et al. "Acetal-Derivatized Dextran: An Acid-Responsive Biodegradable Material for Therapeutic Applications" Journal of the American Chemical Society, 130(32):10494-10495 (2008).
Bachelder et al. "In vitro analysis of acetalated dextran microparticles as a potent delivery platform for vaccine adjuvants" Molecular Pharmaceutics, 7(3):826-835 (2010).

(Continued)

*Primary Examiner* — Yih-Horng Shiao
(74) *Attorney, Agent, or Firm* — Myers Bigel, P.A.

(57) ABSTRACT

The present invention provides a composition comprising a) a polyacetal polymer, a polyester polymer and/or a biodegradable polymer; b) a cyclic dinucleotide; and c) an antigen and/or an antibody, as well as methods of using same.

2 Claims, 52 Drawing Sheets

(56) References Cited

OTHER PUBLICATIONS

Bachelder et al. "Acetalated Dextran: A Tunable and Acid-Labile Biopolymer with Facile Synthesis and a Range of Applications" Chemical Reviews, 117(3):1915-1926 (2017) (Abstract only).
Blaauboer et al. "The mucosal adjuvant cyclic di-GMP enhances antigen uptake and selectively activates pinocytosis-efficient cells in vivo" eLife, 4:e06670 (2015).
Borteh et al. "Electrospun Acetalated Dextran Scaffolds for Temporal Release of Therapeutics" Langmuir, 29(25):7957-7965 (2013) (Abstract only).
Bystricky et al. "Candida albicans mannan-protein conjugate as vaccine candidate" Immunology Letters, 85(3):251-255 (2003) (Abstract only).
Chen et al. "The potential of 3',5'-cyclic diguanylic acid (c-di-GMP) as an effective vaccine adjuvant" Vaccine, 28(18):3080-3085 (2010) (Abstract only).
Chen et al. "Degradation of acetalated dextran can be broadly tuned based on cyclic acetal coverage and molecular weight" International Journal of Pharmaceutics, 512(1):147-157 (2016) (Abstract only).
Chen et al. "Investigation of tunable acetalated dextran microparticle platform to optimize M2e-based influenza efficacy" Journal of Controlled Release, 289:114-124 (2018) (Abstract only).
Chen et al. "Prevention of Type 1 Diabetes with Acetalated Dextran Microparticles Containing Rapamycin and Pancreatic Peptide P31" Advanced Healthcare Materials, 7(18):e1800341 (2018) (Abstract only).
Chen et al. "Tunable Degradation of Acetalated Dextran Microparticles Enables Controlled Vaccine Adjuvant and Antigen Delivery to Modulate Adaptive Immune Responses" Journal of Controlled Release, 273:147-159 (2018).
Cheng et al. "A nanoparticle-incorporated STING activator enhances antitumor immunity in PD-L1-insensitive models of triple-negative breast cancer" JCI Insight, 3(22):e120638 (2018).
Collier et al. "Delivery of host cell-directed therapeutics for intracellular pathogen clearance" Expert Review of Anti-infective Therapy, 11(11):1225-1235 (2013).
Collier et al. "Host-mediated Leishmania donovani treatment using AR-12 encapsulated in acetalated dextran microparticles" International Journal of Pharmaceutics, 499(1-2):186-194 (2016).
Collier et al. "Saquinavir Loaded Acetalated Dextran Microconfetti—a Long Acting Protease Inhibitor Injectable" Pharmaceutical Research, 33(8):1998-2009 (2016).
Collier et al. "Acetalated Dextran Microparticles for Codelivery of STING and TLR7/8 Agonists" Molecular Pharmaceutics, 15(11):4933-4946 (2018) (Abstract only).
Demaria et al. "STING activation of tumor endothelial cells initiates spontaneous and therapeutic antitumor immunity" Proceedings of the National Academy of Sciences, USA, 112(50):15408-15413 (2015).
Dubensky, Jr. et al. "Rationale, progress and development of vaccines utilizing STING-activating cyclic dinucleotide adjuvants" Therapeutic Advances in Vaccines, 1(4):131-143 (2013).
Duong et al. "One Step Encapsulation of Small Molecule Drugs in Liposomes via Electrospray-Remote Loading" Molecular Pharmaceutics, 13(1):92-99 (2016) (Abstract only).
Ebensen et al. "Bis-(3',5')-cyclic dimeric adenosine monophosphate: strong Th1/Th2/Th17 promoting mucosal adjuvant" Vaccine, 29(32):5210-5220 (2011) (Abstract only).
Foged et al. "Particle size and surface charge affect particle uptake by human dendritic cells in an in vitro model" International Journal of Pharmaceutics, 298(2):315-322 (2005) (Abstract only).
Fu et al. "STING agonist formulated cancer vaccines can cure established tumors resistant to PD-1 blockade" Science Translational Medicine, 7(283):283ra52 (2015).
Gallovic et al. "Acetalated Dextran Microparticulate Vaccine Formulated via Coaxial Electrospray Preserves Toxin Neutralization and Enhances Murine Survival Following Inhalational Bacillus Anthracis Exposure" Advanced Healthcare Materials, 5(20):2617-2627 (2016) (Abstract only).
Gallovic et al. "Chemically modified inulin microparticles serving dual function as a protein antigen delivery vehicle and immunostimulatory adjuvant" Biomaterials Science, 4(3):483-493 (2016) (Abstract only).
Gillies et al. "Acetals as pH-Sensitive Linkages for Drug Delivery" Bioconjugate Chemistry, 15(6):1254-1263 (2004) (Abstract only).
Graham-Gurysh et al. "Sustained Delivery of Doxorubicin via Acetalated Dextran Scaffold Prevents Glioblastoma Recurrence after Surgical Resection" Molecular Pharmaceutics, 15(3):1309-1318 (2018).
Gray et al. "Evidence for cyclic diguanylate as a vaccine adjuvant with novel immunostimulatory activities" Cellular Immunology, 278(1-2):113-119 (2012) (Abstract only)
Hanson et al. "Nanoparticulate STING agonists are potent lymph node-targeted vaccine adjuvants" The Journal of Clinical Investigation, 125(6):2532-2546 (2015).
He et al. "Potential therapeutic targets in the process of nucleic acid recognition: opportunities and challenges" Trends in Pharmacological Sciences, 36(1):51-64 (2015) (Abstract only).
Hirota et al. "Optimum conditions for efficient phagocytosis of rifampicin-loaded PLGA microspheres by alveolar macrophages" The Journal of Controlled Release, 119(1):69-76 (2007) (Abstract only).
Hoang et al. "Acetalated Dextran Encapsulated AR-12 as a Host-directed Therapy to Control *Salmonella* Infection" International Journal of Pharmaceutics, 477:334-343 (2014).
Hoang et al. "Needle-Free Delivery of Acetalated Dextran-Encapsulated AR-12 Protects Mice from Francisella tularensis Lethal Challenge" Antimicrobial Agents and Chemotherapy, 60(4):2052-2062 (2016).
International Preliminary Report on Patentability corresponding to International Patent Application No. PCT/US2017/052270 (9 pages) (dated Mar. 28, 2019).
Irvine et al. "Synthetic Nanoparticles for Vaccines and Immunotherapy" Chemical Reviews, 115(19):11109-11146 (2015).
Johansen et al. "Development of synthetic biodegradable microparticulate vaccines: a roller coaster story" Expert Reveiw of Vaccines, 6(4):471-474 (2007).
Johnson et al. "In Vivo and Cellular Trafficking of Acetalated Dextran Microparticles for Delivery of a Host-Directed Therapy for *Salmonella enterica* Serovar Typhi Infection" Molecular Pharmaceutics, 15(11):5336-5348 (2018) (Abstract only).
Junkins et al. "A robust microparticle platform for a STING-targeted adjuvant that enhances both humoral and cellular immunity during vaccination" Journal of Controlled Release, 270:1-13 (2018).
Kanthamneni et al. "Enhanced stability of horseradish peroxidase encapsulated in acetalated dextran microparticles stored outside cold chain conditions" International Journal of Pharmaceutics, 431:101-110 (2012).
Kauffman et al. "Optimization of rapamycin-loaded acetalated dextran microparticles for immunosuppression" International Journal of Pharmaceutics, 422:356-363 (2012).
Kauffman et al. "Synthesis and Characterization of Acetalated Dextran Polymer and Microparticles with Ethanol as a Degradation Product" ACS Applied Materials & Interfaces, 4(8):4149-4155 (2012) (Abstract only).
Krovi et al. "Injectable long-acting human immunodeficiency virus antiretroviral prodrugs with improved pharmacokinetic profiles" International Journal of Pharmaceutics, 552(1-2):371-377 (2018).
Lee et al. "Submicron-sized hydrogels incorporating cyclic dinucleotides for selective delivery and elevated cytokine release in macrophages" Acta Biomaterialia, 29:271-287 (2016) (Abstract only).
Lemos et al. "Activation of the Stimulator of Interferon Genes (STING) adaptor attenuates experimental autoimmune encephalitis" The Journal of Immunology, 192(12):5571-5578 (2014).
Lemos et al. "STING, nanoparticles, autoimmune disease and cancer: a novel paradigm for immunotherapy?" Expert Review of Clinical Immunology, 11(1):155-165 (2015).
Li et al. "Pivotal Roles of cGAS-cGAMP Signaling in Antiviral Defense and Immune Adjuvant Effects" Science, 341(6152):1-10 (2013).

(56) References Cited

OTHER PUBLICATIONS

Li et al. "Antitumor Activity of cGAMP via Stimulation of cGAS-cGAMP-STING-IRF3 Mediated Innate Immune Response" Scientific Reports, 6:19049 (2016).
Libanova et al. "Cyclic di-nucleotides: new era for small molecules as adjuvants" Microbial Biotechnology, 5(2):168-176 (2012).
Major et al. "Intranasal vaccination with a plant-derived H5 HA vaccine protects mice and ferrets against highly pathogenic avian influenza virus challenge" Human Vaccines & Immunotherapeutics, 11(5):1235-1243 (2015).
Meenach et al. "Synthesis, optimization, and characterization of camptothecin-loaded acetalated dextran porous microparticles for pulmonary delivery" Molecular Pharmaceutics, 9(2):290-298 (2012) (Abstract only).
Miyabe et al. "A new adjuvant delivery system 'cyclic di-GMP/YSK05 liposome' for cancer immunotherapy" Journal of Controlled Release, 184:20-27 (2014) (Abstract only).
Moon et al. "Engineering nano- and microparticles to tune immunity" Advanced Materials, 24(28):3724-3746 (2012).
Murthy et al. "A macromolecular delivery vehicle for protein-based vaccines: Acid-degradable protein-loaded microgels" Proceedings of the National Academy of Sciences, 100(9):4995-5000 (2003).
Nakamura et al. "Liposomes loaded with a STING pathway ligand, cyclic di-GMP, enhance cancer immunotherapy against metastatic melanoma" Journal of Controlled Release, 216:149-157 (2015) (Abstract only).
Paramonov et al. "Fully acid-degradable biocompatible polyacetal microparticles for drug delivery" Bioconjugate Chemistry, 19(4):911-919 (2008) (Abstract only).
Paulo et al. "Nanoparticles for intracellular-targeted drug delivery" Nanotechnology, 22:494002 (2011).
Peine et al. "Efficient delivery of the toll-like receptor agonists polyinosinic:polycytidylic acid and CpG to macrophages by acetalated dextran microparticles" Molecular Pharmaceutics, 10(8):2849-2857 (2013) (Abstract only).
Peine et al. "Treatment of Experimental Autoimmune Encephalomyelitis by Codelivery of Disease Associated Peptide and Dexamethasone in Acetalated Dextran Microparticles" Molecular Pharmaceutics, 11(3):828-835 (2014).
Schully et al. "Rapid Vaccination Using an Acetalated Dextran Microparticulate Subunit Vaccine Confers Protection Against Triplicate Challenge by Bacillus Anthracis" Pharmaceutical Research, 30(5):1349-1361 (2013).
Schully et al. "Evaluation of a biodegradable microparticulate polymer as a carrier for Burkholderia pseudomallei subunit vaccines in a mouse model of melioidosis" International Journal of Pharmaceutics, 495(2):849-861 (2015) (Abstract only).
Skrnjug et al. "Cyclic GMP-AMP Displays Mucosal Adjuvant Activity in Mice" PLoS ONE, 9(10):e110150 (2014).
Skrnjug et al. "The Mucosal Adjuvant Cyclic di-AMP Exerts Immune Stimulatory Effects on Dendritic Cells and Macrophages" PLoS ONE, 9(4):e95728 (2014).
Svindland et al. "A study of Chitosan and c-di-GMP as mucosal adjuvants for intranasal influenza H5N1 vaccine" Influenza and Other Respiratory Viruses, 7(6):1181-1193 (2013).
Swanson et al. "A noncanonical function of cGAMP in inflammasome priming and activation" Journal of Experimental Medicine, 214(12):3611-3626 (2017).
Temizoz et al. "TLR9 and STING agonists synergistically induce innate and adaptive type-II IFN" European Journal of Immunology, 45(4):1159-1169 (2015).
Tracy, Mark A. "Development and scale-up of a microsphere protein delivery system" Biotechnology Progress, 14(1):108-115 (1998) (Abstract only).
Walter et al. "Hydrophilic poly(DL-lactide-co-glycolide) microspheres for the delivery of DNA to human-derived macrophages and dendritic cells" The Journal of Controlled Release, 76(1-2):149-168 (2001) (Abstract only).
Watkins-Schulz et al. "A microparticle platform for STING-targeted immunotherapy enhances natural killer cell and CD8+ T cell-mediated anti-tumor immunity" Biomaterials, 205:94-105 (2019).
Xu et al. "Coaxial electrohydrodynamic atomization process for production of polymeric composite microspheres" Chemical Engineering Science, 104:330-346 (2013).
Yildiz et al. "Enhanced immunostimulatory activity of cyclic dinucleotides on mouse cells when complexed with a cell-penetrating peptide or combined with CpG" European Journal of Immunology, 45:1170-1179 (2015).
Broaders et al. "Acetalated dextran is a chemically and biologically tunable material for particulate immunotherapy" Proceedings of the National Academy of Sciences 106(14):5497-5502 (2009).
Duong et al. "Electrospray Encapsulation of Toll-Like Receptor Agonist Resiquimod in Polymer Microparticles for the Treatment of Visceral Leishmaniasis" Molecular Pharmacology 10(3):1-26 (2013)
Hiremath et al. "Entrapment of H1N1 Influenza Virus Derived Conserved Peptides in PLGA Nanoparticles Enhances T Cell Response and Vaccine Efficacy in Pigs" PLoS ONE 11(4):e0151922 (2016).
Huse et al. "Generation of a Large Combinatorial Library of the Immunoglobulin Repertoire in PhageLambda" Science (1989) 246(4935):1275-1281.
International Search Report and the Written Opinion of the International Searching Authority corresponding to International Patent Application No. PCT/US2017/052270 (12 pages) (dated Dec. 14, 2017).
Kang et al. "Antibody redesign by chain shuffling from random combinatorial immunoglobulin libraries" Proceedings of the National Academy of Sciences USA 88:11120-11123 (1991).
Kohler et al. "Continuous cultures of fused cells secreting antibody of predefined specificity" Nature 265:495-97 (1975).
Madhun et al. "Intranasal c-di-GMP-adjuvanted plant-derived H5 influenza vaccine induces multifunctional Th1 CD4+ cells and strong mucosal and systemic antibody responses in mice" Vaccine 29:4973-4982 (2011).
Morrison et al. "Chimeric human antibody molecules: mouse antigen-binding domains with human constant region domains" Proceedings of the National Academy of Sciences USA 81:6851-6855 (1984).
Neuberger et al. "Recombinant antibodies possessing novel effector functions" Nature 312(5995):604-608 (1984) (Abstract only).
Sridhar et al. "Electrosprayed nanoparticles for drug delivery and pharmaceutical applications" Biomatter 3(3):e24281 (2013).
Takeda et al. "Construction of chimaeric processed immunoglobulin genes containing mouse variable and human constant region sequences" Nature 314(6010):452-454 (1985) (Abstract only).
Walker et al. "Interaction of human IgG chimeric antibodies with the human FcRI and FcRII receptors: requirements for antibody-mediated host cell-target cell interaction" Molecular Immunology 26(4):403-411 (1989) (Abstract only).

* cited by examiner

METHODS AND COMPOSITIONS FOR INDUCING AN IMMUNE RESPONSE

STATEMENT OF PRIORITY

This application is a 35 U.S.C. § 371 national phase application of International Application Serial No. PCT/US2017/052270, filed Sep. 19, 2017, which claims the benefit, under 35 U.S.C. § 119(e), of U.S. Provisional Application No. 62/396,774, filed Sep. 19, 2016, the entire contents of each of which are incorporated by reference herein.

STATEMENT OF GOVERNMENT SUPPORT

This invention was made with government support under Grant Nos. U19 AI109784, T32-HL007106 and T32-AI007151 awarded by the National Institutes of Health. The government has certain rights in the invention.

FIELD OF THE INVENTION

The present invention relates to methods and compositions for inducing an immune response, inducing production of interferons and treating various disorders in a subject.

BACKGROUND OF THE INVENTION

Immune responses can be induced to prevent or treat various conditions such as viral infections, bacterial infections, or cancer. These responses can be prompted in certain immune cells such as phagocytes via activation of pathogen recognition receptors (PRRs) with molecules known as pathogen-associated molecular patterns (PAMPs). Activation of one PRR in particular, stimulator of interferon genes (STING, a.k.a. MITA, MPYS, ERIS), is interesting due to its role in anti-viral immunity. This pathway can be exploited for prevention or treatment of viral infections, bacterial infections, or cancer. However, a major hindrance to activating STING and other intracellular PRRs is their phagosomal or cytosolic localization which requires intracellular delivery of their respective agonists. Using biodegradable polymers formulated into particulate delivery vehicles incorporating cyclic dinucleotide STING agonist(s) or other PAMP cargo is one way to overcome this barrier. Furthermore, these delivery vehicles can allow for more targeted delivery to phagocytes, resulting in safer PAMP formulations and PAMP dose-sparing.

With regard to the prevention of infections via prophylactic vaccines, many FDA-approved vaccines are live-attenuated or inactivated pathogens. Subunit protein-based formulations are a safer alternative, but protein antigens often suffer from poor immunogenicity and require addition of an immunostimulatory agent known as an adjuvant.

Although adjuvants such as alum and squalene-based emulsions have proven to be effective inducers of potent Th2-biased responses and humoral immunity, they frequently fail to induce significant Th1-biased cellular responses that drive protective immunity against intracellular pathogens. Furthermore, their mechanisms of action are poorly understood. As a result, there is a significant need for novel vaccine adjuvants such as cyclic dinucleotide (CDN) STING agonists or other PAMPs formulated with biodegradable polymer delivery vehicles, which are capable of inducing balanced Th1 and Th2 immunity that act through more well-defined mechanisms.

Acute and chronic intracellular infections can lead to life long, and/or life threatening conditions. Few treatment options are available for many of these infections. Intracellular PRRs play a key role in detecting and coordinating a response against intracellular pathogens, and can be targeted therapeutically to enhance their clearance. Infections can be treated with STING agonists such as cyclic dinucleotides or other PAMPs formulated with biodegradable polymer delivery vehicles, leading to the production of cytokines that can help direct the immune system to clear the infection. This approach is superior to current state-of-the-art as it boosts the body's innate ability to clear dangerous intracellular pathogens, rather than targeting the pathogen itself. As a result there is a lower change of the pathogen acquiring resistance, and less opportunity for toxicity associated with anti-microbial drugs.

Finally, immunotherapy has revolutionized cancer therapy through harnessing the power of the patients own immune system to kill tumor cells. However, immunotherapies available in clinic target only acquired immunity, while ignoring the arguably more important innate immune response. By harnessing innate immunity it is possible to both drive acquired immunity against, and target the pro-tumorigenic microenvironment. This approach has significant advantages over non-specific state-of-the-art cancer treatment regimens such as radiation and chemotherapeutics that can be very toxic to the patient. Using immunotherapies such as cyclic dinucleotide STING agonists or other PAMPs formulated with biodegradable polymer delivery vehicles can be used to treat cancer by targeting the tumor microenvironment and by training the host immune system to combat cancer cells in a more specific and tolerable way.

The present invention addresses the shortcomings in the art by providing methods and compositions for inducing an immune response and treating various disorders in a subject.

SUMMARY OF THE INVENTION

In one aspect, the present invention provides a composition comprising: a) a biodegradable polymer selected from the group consisting of polymers such as polyacetalated dextran or a polyester; b) a cyclic dinucleotide such as cyclic guanosine monophosphate-adenosine monophosphate (cGAMP) selected from the group consisting of 3'3'cGAMP (cyclic [G(3',5')pA(3',5')p]) and 2'3'cGAMP (cyclic [G(2',5')pA(3',5')p]) and/or one or more other immunostimulatory agent; and c) an antigen.

In an additional aspect, the present invention provides a composition comprising: a) a biodegradable polymer selected from the group consisting of polymers such as polyacetalated dextran or a polyester; b) a cyclic dinucleotide such as cyclic guanosine monophosphate-adenosine monophosphate (cGAMP) selected from the group consisting of 3'3'cGAMP (cyclic [G(3',5')pA(3',5')p]) and 2'3'cGAMP (cyclic [G(2',5')pA(3',5')p]) and/or one or more other immunostimulatory agent.

In a further aspect, the present invention provides a method of inducing an immune response in a subject, comprising administering to the subject an effective amount of the composition of this invention.

In another aspect, the present invention provides a method of treating a viral infection and/or preventing a disorder associated with viral infection in a subject, comprising administering to the subject an effective amount of the composition of this invention.

Further provided herein is a method of treating a bacterial infection and/or preventing a disorder associated with bacterial infection in a subject, comprising administering to the subject an effective amount of the composition of this invention.

Further provided herein is a method of treating a parasitic infection and/or preventing a disorder associated with parasitic infection in a subject, comprising administering to the subject an effective amount of the composition of this invention.

An additional aspect of this invention is a method of treating cancer in a subject (e.g., a subject in need thereof), comprising administering to the subject an effective amount of the composition of this invention.

Another aspect of this invention includes a method of inducing production of interferon and/or a cytokine in a subject (e.g., a subject in need thereof), comprising administering to the subject an effective amount of a composition of this invention.

Additionally provided herein is a method of treating an autoimmune disorder in a subject (e.g., a subject in need thereof), comprising administering to the subject an effective amount of a composition of this invention.

In a further aspect, the present invention provides a composition comprising: a) a biodegradable polyacetalated polymer; and b) an antibody. In further embodiments, the composition will include c) a cyclic dinucleotide such as a cyclic guanosine monophosphate-adenosine monophosphate (cGAMP) selected from the group consisting of 3'3'cGAMP (cyclic [G(3',5')pA(3',5')p]) and 2'3'cGAMP (cyclic [G(2',5')pA(3',5')p]).

DETAILED DESCRIPTION OF THE INVENTION

Figure 1:
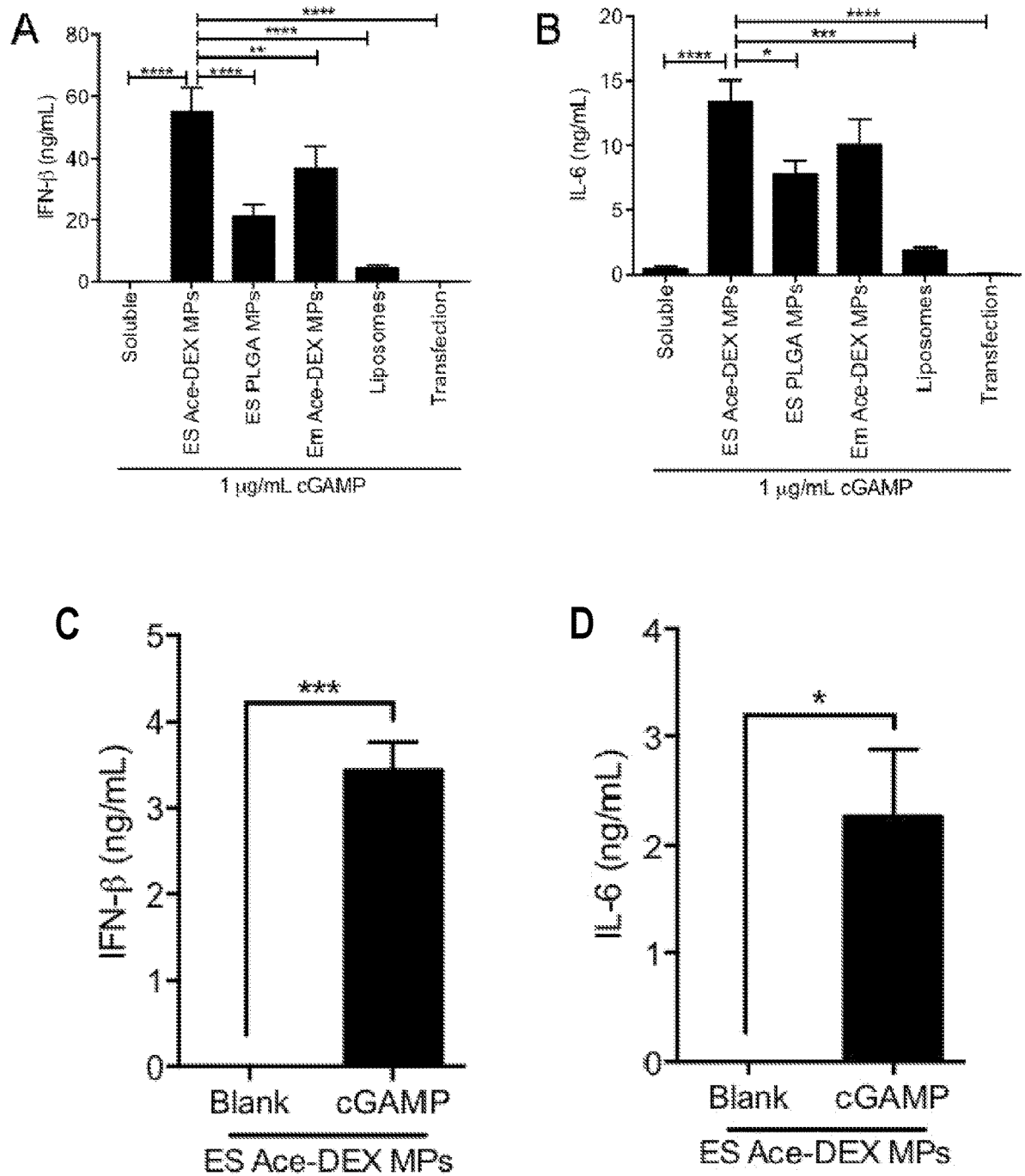
FIG. 1. Evaluation of cGAMP delivery platforms: (A, B) Bone marrow derived dendritic cells (BMDCs) from C57BL/6 mice were treated with 1 µg/mL soluble cGAMP, or an equivalent dose of cGAMP delivered in electrosprayed acetalated dextran microparticles (ES Ace-DEX MPs), electrosprayed poly(lactic-co-glycolic acid) microparticles (ES PLGA MPs), emulsion acetalated dextran microparticles (EM Ace-DEX MPs), SoyPC-DOTAP liposomes (Liposomes) or Lipofectamine 3000 transfection reagent (Transfection). Supernatants were collected 6 hours later and assayed for interferon-beta (IFN-β) and interleukin-6 (IL-6). (C, D) Cytokine production from BMDCs treated with blank or 1 µg/mL cGAMP ES Ace-DEX MPs after incubation for 28 days in RPMI media containing 10% FBS at pH 7.2 (all data represent BMDCs cultured from 3-4 individual mice±SEM. *p<0.05, p<0.01, *p<0.001, ****p<0.0001).

The present invention will now be described more fully hereinafter with reference to the accompanying drawings and specification, in which preferred embodiments of the invention are shown. This invention may, however, be embodied in different forms and should not be construed as limited to the embodiments set forth herein.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of dose (e.g., an amount of a non-viral vector) and the like, is meant to encompass variations of ±20%, ±10%, ±5%, ±1%, ±0.5%, or even ±0.1% of the specified amount.

As used herein, the transitional phrase "consisting essentially of" (and grammatical variants) means that the scope of a claim is to be interpreted to encompass the specified materials or steps recited in the claim, "and those that do not materially affect the basic and novel characteristic(s)" of the claimed invention. Thus, the term "consisting essentially of" when used in a claim of this invention is not intended to be interpreted to be equivalent to "comprising."

The present invention is based on the unexpected discovery that cGAMP microparticles as described herein can activate STING (stimulator of interferon genes), which is a master regulator of the host interferon (IFN) response. Thus, in one embodiment, the present invention provides a composition comprising: a) a polymer selected from the group consisting of acetalated dextran, polyacetals, polyketals, polyesters (e.g., poly(lactic-co-glycolic acid) (PLGA)), polyanhydrides, polyorthoesters, poly(beta-amino)esters, polystyrenes, and poly vinyl alcohol (PVA), singly or in any combination; b) a cyclic dinucleotide selected from the group consisting of cyclic-di-AMP, cyclic di-GMP, or cyclic guanosine monophosphate-adenosine monophosphate (cGAMP) selected from the group consisting of 3'3'cGAMP (cyclic [G(3',5')pA(3',5')p]) and 2'3'cGAMP (cyclic [G(2',5')pA(3',5')p]) singly or in any combination; and c) one or more (e.g., 2, 3, 4, 5, 6, 7, 8, 9, 10, etc.) antigen. In some embodiments, this composition can also comprise one or more (e.g., 2, 3, 4, 5, 6, 7, 8, 9, 10, etc.) immunostimulatory agents. The antigens and immunostimulatory agents of this invention can be present in any combination in the compositions of this invention.

The present invention further provides a composition comprising, consisting essentially of or consisting of: a) a polymer selected from the group consisting of acetalated dextran, polyacetals, polyketals, polyesters (e.g., poly(lactic-co-glycolic acid) (PLGA)), polyanhydrides, polyorthoesters, poly(beta-amino)esters, polystyrenes, and poly vinyl alcohol (PVA), singly or in any combination; and b) a cyclic dinucleotide selected from the group consisting of cyclic-di-AMP, cyclic di-GMP, or cyclic guanosine monophosphate-adenosine monophosphate (cGAMP) selected from the group consisting of 3'3'cGAMP (cyclic [G(3',5')pA(3',5')p]) and 2'3'cGAMP (cyclic [G(2',5')pA(3',5')p]) singly or in any combination. In this embodiment, the composition does not comprise an antigen.

In further embodiments, the present invention provides a composition comprising: a) a polyacetal polymer; b) a cyclic dinucleotide and/or a first immunostimulatory agent; and c) an antigen.

In yet another embodiment, the present invention provides a composition comprising: a) a polyester polymer; b) a cyclic dinucleotide and/or a first immunostimulatory agent; and c) an antigen.

In an additional embodiment, the present invention provides a composition comprising: a) a biodegradable polymer; b) a cyclic dinucleotide and/or a first immunostimulatory agent; and c) an antigen.

In some embodiments, the cyclic dinucleotide of this invention is a cyclic guanosine monophosphate-adenosine monophosphate (cGAMP) selected from the group consisting of 3'3'cGAMP (cyclic [G(3',5')pA(3',5')p]) and 2'3'cGAMP (cyclic [G(2',5')pA(3',5')p]).

In some embodiments, the cyclic dinucleotide is c-di-GMP, c-di-AMP, c-di-UMP, c-di-IMP, di-thio-(Rp,Rp)-[cyclic[A(2',5')pA(3',5')p]], derivatives or analogs thereof, or an agonist of the stimulator of interferon genes (STING) receptor.

In some embodiments, the composition of this invention can be a nanoparticle or microparticle. In some embodiments, the nanoparticle or microparticle is an electrosprayed biodegradable polymer particle. In some embodiments, the nanoparticle or microparticle is an electrosprayed polyacetalated dextran particle. In some embodiments, the nanoparticle or microparticle is an electrosprayed polyester particle. In some embodiments, the nanoparticle or microparticle is an emulsion biodegradable polymer particle. In some embodiments, the nanoparticle or microparticle is an emulsion polyacetalated dextran particle. In some embodiments, the nanoparticle or microparticle is an emulsion polyester particle.

In some embodiments, the nanoparticle or microparticle of this invention is made by spray drying, coacervation, nanoprecipitation, solvent displacement, phase separation, or any other particle fabrication technique.

In some embodiments, an antigen of this invention is a viral antigen. In some embodiments, the viral antigen is from a virus selected from the group consisting of an orthomyxovirus, a flavivirus, a filovirus, a paramyxovirus, a lentivirus, a hepatotropic virus, and any combination thereof. In some embodiments, the orthomyxovirus is an influenza virus. In some embodiments, the viral antigen is an influenza HA antigen, an influenza HA stalk region antigen, an influenza NP antigen, an influenza M1 antigen, an influenza M2e antigen, a B cell epitope, a CD4 T cell epitope, a CD8 T cell epitope, or any combination thereof. In some embodiments, the flavivirus is Zika virus. In some embodiments, the flavivirus is dengue virus. In some embodiments, the filovirus is Ebola virus. In some embodiments, the lentivirus is human immunodeficiency virus (HIV). In some embodiments, the hepatotropic virus is hepatitis A, hepatitis B, hepatitis C, hepatitis D, hepatitis E, or any combination thereof.

In some embodiments, the antigen of this invention is a bacterial antigen.

In some embodiments, the antigen of this invention is a parasite antigen.

In some embodiments, the antigen of this invention is a tumor antigen.

In some embodiments, the composition of this invention can comprise a second, third, fourth, or more (e.g., fifth, sixth, seventh, eighth, ninth, tenth, eleventh, twelfth, thirteenth, fourteenth, fifteenth, sixteenth, seventeenth, eighteenth, nineteenth, or twentieth) immunostimulatory agent.

In some embodiments, the immunostimulatory agent of this invention is a pathogen-associated molecular pattern. In some embodiments, the pathogen-associated molecular pattern is a nucleotide-binding and oligomerization domain 2 (NOD2) agonist, a toll-like receptor (TLR) 4 agonist, poly (dA:dT), a TLR 9 agonist oligodeoxynucleotide containing CpG motif, a TLR 3/retinoic acid-inducible gene (RIG)-I agonist, or any combination thereof. In some embodiments, the pathogen-associated molecular pattern is a TLR 7/8 agonist, resiquimod, N-[4-[(4-amino-2-butyl-1H-imidazo[4,5-c]quinolin-1-yl)oxy]butyl]-octadecanamide, 5-(4-amino-2-methyl-1H-imidazo[4,5-c]quinolin-1-yl)-4,4-dimethyl-2-pentanone, N-[4-(4-amino-2-ethyl-1H-imidazo[4,5-c]quinolin-1-yl)butyl]-methanesulfonamide, N-[2-[4-amino-2-(ethoxymethyl)-1H-imidazo[4,5-c]quinolin-1-yl]-1,1-dimethylethyl]-methanesulfonamide, or any derivatives or analogs thereof. In some embodiments, the pathogen-associated molecular pattern is a TLR 7 agonist, imiquimod, or any derivatives or analogs thereof. In some embodiments, the pathogen-associated molecular pattern is a NOD2 agonist, murabutide, muramyl dipeptide (MDP), or any derivatives or analogs thereof. In some embodiments, the pathogen-associated molecule pattern is a toll-like receptor (TLR) 4 agonist, lipopolysaccharide, synthetic monophosphoryl lipid A, monophosphoryl lipid A from *Salmonella minnesota* R595, glucopyranosyl lipid adjuvant (GLA), or any derivatives or analogs thereof. In some embodiments, the pathogen-associated molecular pattern is TLR 3/RIG-I agonist polyinosinic:polycytidylic acid.

The present invention provides a pharmaceutical composition comprising the composition of this invention and a pharmaceutically acceptable carrier.

Further provided herein are various methods employing the compositions of this invention. Thus, in one embodiment, the present invention provides a method of inducing an immune response for prevention and/or treatment of disease or disorder in a subject, comprising administering to the subject an effective amount of the composition of this invention.

Also provided herein is a method of treating a viral infection and/or treating or preventing a disorder associated with viral infection in a subject, comprising administering to the subject an effective amount of the composition of this invention.

In addition, the present invention provides a method of treating a bacterial infection and/or treating or preventing a disorder associated with bacterial infection in a subject, comprising administering to the subject an effective amount of the composition of this invention.

Further provided herein is a method of treating a parasitic infection and/or treating or preventing a disorder associated with parasitic infection in a subject, comprising administering to the subject an effective amount of the composition of this invention.

In additional embodiments, the present invention provides a method of treating and/or preventing cancer in a subject in need thereof, comprising administering to the subject an effective amount of the composition of this invention.

In further embodiments, the present invention provides a method of inducing immune activation in a subject in need thereof, comprising administering to the subject an effective amount of a composition comprising a biodegradable polymer and a cyclic dinucleotide and/or a first immunostimulatory agent.

Additionally, the present invention provides a method of inducing immune activation in a subject in need thereof, comprising administering to the subject an effective amount of a composition comprising a polyacetal polymer and a cyclic dinucleotide and/or a first immunostimulatory agent.

In another embodiment, the present invention provides a method of inducing immune activation in a subject in need thereof, comprising administering to the subject an effective amount of a composition comprising a polyester polymer and a cyclic dinucleotide and/or a first immunostimulatory agent.

In the methods described above, the composition can comprise a nanoparticle or microparticle that is an electrosprayed biodegradable polymer particle, an electrosprayed polyacetalated dextran particle, or an electrosprayed polyester particle.

In other embodiments of the methods of this invention, the composition can comprise a nanoparticle or microparticle that is an emulsion biodegradable polymer particle, an emulsion polyacetalated dextran particle, or an emulsion polyester particle.

In the methods described above, the nanoparticle or microparticle can be made by spray drying, coacervation, nanoprecipitation, solvent displacement, phase separation, or any other particle fabrication technique, including in any combination.

In some embodiments of the methods described herein, the immune activation leads to production of a cytokine and in some embodiments, the cytokine can be a type-I interferon.

In some embodiments, the cytokine can be interleukin-6 (IL-6), tumor necrosis factor (TNF), a member of the interleukin 1 (IL-1) family, interferon gamma-induced protein 10 (IP-10), interleukin-12 (IL-12), MIP-1α, RANTES, or any combination thereof.

In some embodiments of the methods described herein, the cytokine can be interleukin-8 (IL)-8, interleukin-15 (IL-15), interleukin-27 (IL-27), or any combination thereof.

In some embodiments of the methods of this invention, the subject can be a subject in need of treatment and/or prevention of cancer.

In some embodiments of the methods of this invention, the subject can be a subject in need of treatment and/or prevention of a viral infection.

In some embodiments of the methods of this invention, the subject can be a subject in need of treatment and/or prevention of a bacterial infection.

In some embodiments of the methods of this invention, the subject can be a subject in need of treatment and/or prevention of a parasitic infection.

In some embodiments of the methods of this invention, the subject can be a subject in need of treatment and/or prevention of an autoimmune disorder. In some embodiments, the autoimmune disorder can be multiple sclerosis (MS).

In some embodiments of the methods described herein, the cyclic dinucleotide can be a cyclic guanosine monophosphate-adenosine monophosphate (cGAMP) selected from the group consisting of 3'3'cGAMP (cyclic [G(3',5')pA(3',5')p]) and 2'3'cGAMP (cyclic [G(2',5')pA(3',5')p]).

In some embodiments of the methods described herein, the cyclic dinucleotide can be c-di-GMP, c-di-AMP, c-di-UMP, c-di-IMP, di-thio-(Rp,Rp)-[cyclic[A(2',5')pA(3',5')p]], derivatives or analogs thereof, or an agonist of the stimulator of interferon genes (STING) receptor.

In some embodiments of the methods described herein, the composition can further comprise a second, third, fourth, or more (e.g., fifth, sixth, seventh, eighth, ninth, tenth, eleventh, twelfth, thirteenth, fourteenth, fifteenth, sixteenth, seventeenth, eighteen, nineteenth, or twentieth) immunostimulatory agent.

In some embodiments of the methods described herein, the immunostimulatory agent can be a pathogen-associated molecular pattern. In some embodiments, the pathogen-associated molecular pattern can be a nucleotide-binding and oligomerization domain 2 (NOD2) agonist, a toll-like receptor (TLR) 4 agonist, poly (dA:dT), a TLR 9 agonist oligodeoxynucleotide containing CpG motif, a TLR 3/retinoic acid-inducible gene (RIG)-I agonist, or any combination thereof. In some embodiments, the pathogen-associated molecular pattern can be a TLR 7/8 agonist, including resiquimod, N-[4-[(4-amino-2-butyl-1H-imidazo[4,5-c]quinolin-1-yl)oxy]butyl]-octadecanamide, 5-(4-amino-2-methyl-1H-imidazo[4,5-c]quinolin-1-yl)-4,4-dimethyl-2-pentanone, N-[4-(4-amino-2-ethyl-1H-imidazo[4,5-c]quinolin-1-yl)butyl]-methanesulfonamide, N-[2-[4-amino-2-(ethoxymethyl)-1H-imidazo[4,5-c]quinolin-1-yl]-1,1-dimethylethyl]-methanesulfonamide, or any derivatives or analogs thereof. In some embodiments, the pathogen-associated molecular pattern can be a TLR 7 agonist, imiquimod, or any derivatives or analogs thereof. In some embodiments, the pathogen-associated molecular pattern can be a NOD2 agonist, murabutide, muramyl dipeptide (MDP), or any derivatives or analogs thereof. In some embodiments, the pathogen-associated molecular pattern can be a toll-like receptor (TLR) 4 agonist, lipopolysaccharide, synthetic monophosphoryl lipid A, monophosphoryl lipid A from Salmonella minnesota R595, glucopyranosyl lipid adjuvant (GLA), or any derivatives or analogs thereof. In some embodiments, the pathogen-associated molecular pattern can be TLR 3/RIG-I agonist polyinosinic:polycytidylic acid.

In further embodiments, the present invention provides a composition comprising: a) a polyacetal polymer; and b) an antibody. In some embodiments, this composition can comprise a cyclic dinucleotide, a STING agonist and/or one or more (e.g., 2, 3, 4, 5, 6, 7, 8, 9, 10, 11, 12, etc.) immunostimulatory agent in any combination. In some embodiments of this composition, the antibody can be anti-PD-L1, anti-PD-1 or anti-CTLA-4. In some embodiments of this composition, the antibody can be a bispecific fusion protein. In some embodiments of this composition, the antibody can be conjugated to a drug and/or therapeutic agent and/or a detectable agent.

In additional embodiments, the present invention provides a composition selected from the group consisting of: A) a composition comprising: a) a polyacetal polymer; b) a cyclic dinucleotide and/or a first (e.g., one or more (2, 3, 4, 5, 6, 7, 8, 9, 10, 11, 12, etc.)) immunostimulatory agent; and c) an antigen, B) a composition comprising: a) a polyester polymer; b) a cyclic dinucleotide and/or a first immunostimulatory agent; and c) an antigen, and C) a composition comprising: a) a biodegradable polymer; b) a cyclic dinucleotide and/or a first immunostimulatory agent; and c) an antigen, wherein the antigen is an influenza M2e antigen.

In some embodiments of this invention, the cGAMP is 3', 3' cGAMP and in some embodiments, the cGAMP is 2', 3' cGAMP.

In some embodiments, the polymer of this invention can be a polyhydroxylated polymer, which can be a preformed natural polymer or hydroxyl-containing polymer including but not limited to, a multiply-hydroxylated polymer, a polysaccharide, a carbohydrate, a polyol, polyvinyl alcohol, a poly amino acid such as polyserine, and other polymers such as 2-(hydroxyethyl)methacrylate.

In some embodiments, the polysaccharide that can be used in this invention can be but is not limited to, dextran, mannan, pullulan, maltodextrin, inulin, starch, cellulose and a cellulose derivative, gum (e.g., xanthan, locust bean, etc.), and pectin.

In some embodiments, the polyhydroxylated polymer is modified with pendant acetals, thus providing a polyacetal polymer. These polymers that are modified with acetals include, but not limited to polysaccharides, polyserine, polyol, polyvinyl alcohol, 2-hydroxyethylmethacrylate, singly or in any combination.

In some embodiments, a polysaccharide of this invention can have pendant acetals, thus providing acetal-derivatized polysaccharides. In some embodiments, a polyhydroxylated polymer of this invention can be acetal-derivatized dextran, acetal-derivatized inulin, acetal-derivatized mannan or acetal-derivatized polyvinyl alcohol, singly or in any combination.

In some embodiment, a polyhydroxylated polymer of this invention can be made into particles for such applications as vaccine delivery. Nonlimiting examples of formulations for therapeutic agents incorporated in these delivery systems include solid particle dispersions, encapsulated agent dispersions, excipients, emulsions, suspensions, liposomes, microparticles or nanoparticles.

In particular embodiments, the composition of this invention can be a microparticle or nanoparticle and in particular embodiments, the acetalated dextran microparticle or nanoparticle is formed by electrohydrodynamic spraying (electrospray). In some embodiments, the microparticle or nanoparticle can be an emulsion acetalated dextran microparticle or nanoparticle. In some embodiments, the microparticle or nanoparticle can be an electrosprayed PLGA microparticle or nanoparticle and in some embodiments, the microparticle or nanoparticle can be an emulsion PLGA microparticle or nanoparticle. In some embodiments the particles are made via co-axial electrospray. In some embodiments the particles are made via single axial/monoaxial electrospray. In some embodiments the particles are made though double emulsion particle synthesis. In some embodiments the particles are made through single emulsion particle synthesis. In some embodiments the particles are made through coacervation. In some embodiments the particles are made through the salting out method. In some embodiments the particles are made through nanoprecipitation. In some embodiments the particles are made through spray drying.

In some embodiments, an acetalated polyhydroxylated polymer of this invention can be made into particles that are 5 to 80,000 nm in size. In general, particles can be synthesized by various techniques, such as double emulsion or spray drying methods, as is known in the art. In some embodiments, the particles can be made by double emulsion, single emulsion, or precipitation processes.

In some embodiments, single emulsion and double emulsion methods and precipitation processes can be used to produce particles from sub-micrometer to multi-micrometer sizes. Exemplary size ranges can be from about 30 nm to about 500,000 nm, about 30 nm to about 2000 nm, and about 40 nm to about 200 nm. Other exemplary size ranges are about 5000 nm to about 500,000 nm, including any value from about 20 to about 500,000 not specifically recited here (e.g., about 30, 40, 50, 60, 70, 80, 90, 100, 200, 300, 400, 500, 600, 700, 800, 900, 1000, 10,000, 20,000, 30,000, 40,000, 50,000, 60,000, 70,000, 80,000, 90,000, 100,000, 200,000, 300,000, 400,000, 500,000, etc.)

In some embodiments, the antigen can be a viral antigen and in particular embodiments, the viral antigen can be from a virus selected from the group consisting of an orthomyxovirus, a flavivirus, a filovirus, a paramyxovirus, a lentivirus, a hepatotropic virus, and any combination thereof.

In particular embodiments, the orthomyxovirus can be an influenza virus and in various embodiments, the viral antigen can be an influenza HA antigen, an influenza HA stalk region antigen, an influenza NP antigen, an influenza M1 antigen, an influenza M2e antigen or any combination thereof.

In some embodiments, the flavivirus can be Zika virus and/or dengue virus.

In some embodiments, the filovirus can be Ebola virus.

In some embodiments, the lentivirus can be human immunodeficiency virus (HIV).

In some embodiments, the hepatotropic virus can be hepatitis A, hepatitis B, hepatitis C, hepatitis D, or hepatitis E.

In some embodiments, the antigen can be a bacterial antigen and in some embodiments, the antigen can be a tumor antigen.

Nonlimiting examples of antigens of this invention include, singly or in any combination: Mesothelin, Wilms' tumor-1 associated protein (Wt-1), including isoform A; isoform B; isoform C; isoform D, Stratum corneum chymotryptic enzyme (SCCE), and variants thereof, MHC class I chain-related protein A (MICA); MHC class I chain-related protein A (MICB), Gastrin and peptides derived from gastrin; gastrin/CCK-2 receptor (also known as CCK-B), Glypican-3 (an antigen of, e.g., hepatocellular carcinoma and melanoma), Coactosin-like protein, Prostate stem cell antigen (PSCA), Prostate acid phosphatase (PAP); prostate-specific antigen (PSA); PSM; PSMA, Six-transmembrane epithelial antigen of prostate (STEAP), Prostate carcinoma tumor antigen-1 (PCTA-1), Prostate tumor-inducing gene-1 (PTI-1), Prostate-specific gene with homology to G protein-coupled receptor, Prostase (an androgen regulated serine protease), Proteinase 3, Cancer-testis antigens, e.g., NY-ESO-1; SCP-1; SSX-1; SSX-2; SSX-4; GAGE, CT7, CT8; CT10; MAGE-1; MAGE-2; MAGE-3; MAGE-4; MAGE-6; LAGE-1, MAGE-A1, MAGE-A2; MAGE-A3; MAGE-A4; MAGE-A6; MAGE-A9; MAGE-A10; MAGE-A12; GAGE-3/6; NT-SAR-35; BAGE; CA125, GAGE-1; GAGE-2; GAGE-3; GAGE-4; GAGE-5; GAGE-6; GAGE-7; GAGE-8; GAGE-65; GAGE-11; GAGE-13; GAGE-7B, HIP1R; LMNA; KIAA1416; Seb4D; KNSL6; TRIP4; MBD2; HCAC5; MAGEA3, DAM family of genes, e.g., DAM-1; DAM-6, RCAS1, RU2, CAMEL, Colon cancer associated antigens, e.g., NY-CO-8; NY-CO-9; NY-CO-13; NY-CO-16; NY-CO-20; NY-CO-38; NY-CO-45; NY-CO-9/HDAC5; NY-CO-41/MBD2; NY-CO-42/TRIP4; NY-CO-95/KIAA1416; KNSL6; seb4D, N-Acetylglucosaminyl-transferase V (GnT-V), Elongation factor 2 mutated (ELF2M), HOM-MEL-40/SSX2, BRDT, SAGE; HAGE, RAGE, MUM-1 (melanoma ubiquitous mutated); MUM-2; MUM-2 Arg-Gly mutation; MUM-3, LDLR/FUT fusion protein antigen of melanoma, NY-REN series of renal cancer antigens, NY-BR series of breast cancer antigens, e.g., NY-BR-62; NY-BR-75; NY-BR-85; NY-BR-62; NY-BR-85, BRCA-1; BRCA-2, DEK/CAN fusion protein, Ras, e.g., wild type ras, ras with mutations at codon 12, 13, 59, or 61, e.g., mutations G12C; G12D; G12R; G12S; G12V; G13D; A59T; Q61H. K-RAS; H-RAS; N-RAS, BRAF (an isoform of RAF), Melanoma antigens, including HST-2 melanoma cell antigens, Survivin, MDM-2, Methyl-CpG-binding proteins (MeCP2; MBD2), NA88-A, Histone deacetylases (HDAC), e.g., HDAC5, Cyclophilin B (Cyp-B), CA 15-3; CA 27.29, Heat shock protein Hsp70, GAGE/PAGE family, e.g., PAGE-1; PAGE-2; PAGE-3; PAGE-4; XAGE-1; XAGE-2; XAGE-3, MAGE-A, B, C, and D families. MAGE-B5; MAGE-B6; MAGE-C2; MAGE-C3; MAGE-3; MAGE-6, Kinesin 2; TATA element modulatory factor 1; tumor protein D53; NY, Alpha-fetoprotein (AFP), SART1; SART2; SART3; ART4, Preferentially expressed antigen of melanoma (PRAME), Carcinoembryonic antigen (CEA), CAP 1-6D enhancer agonist peptide, HER-2/neu, Cdk4; cdk6; p16 (INK4); Rb protein, TEL; AML1; TEL/AML1, Telomerase (TERT), 707-AP, Annexin, e.g., Annexin II, BCR/ABL; BCR/ABL p210; BCR/ABL p190; CML-66; CML-28, BCL2; BLC6; CD10 protein, CDC27 (this is a melanoma antigen), Sperm protein 17 (SP17); 14-3-3-zeta; MEMD; KIAA0471; TC21, Tyrosinase-related proteins 1 and 2 (TRP-1 and TRP-2), Gp100/pmel-17, TARP, Tyrosinase-related proteins 1 and 2 (TRP-1 and TRP-2), Melanocortin 1 receptor (MC1R); MAGE-3; gp100; tyrosinase; dopachrome tautomerase (TRP-2); MART-1, MUC-1; MUC-2, Spas-1, CASP-8; FLICE; MACH, CEACAM6; CAP-1, HMGB1 (a DNA binding protein and cytokine), ETV6/AML1, Mutant and wild type forms of adenomatous polyposis coli (APC); beta-catenin; c-met; p53; E-cadherin; cyclooxygenase-2 (COX-2), Renal cell carcinoma bound by mAB G250, EphA2, EGFRvIII, *Francisella tularensis* A and B, Circumsporozoite protein (CSP); SSP2; HEP17; Exp-1 orthologs found in *P. falciparum*; and LSA-1, Ring-infected erythrocyte surface protein (RESA); merozoite surface protein 2 (MSP2); Spf66; merozoite surface protein I(MSP1); 195A; BVp42, Apical membrane antigen 1 (AMA1), Hepatitis A, Hepatitis B, Hepatitis C, Hepatitis D, Human papillomavirus, including all 200+ subtypes (classed in 16 groups), such as the high risk subtypes 16, 18, 30, 31, 33, 45, Human T-cell lymphotropic virus (HTLV) types I and II, including the HTLV type I subtypes Cosmopolitan, Central African, and Austro-Melanesian, and the HTLV type II subtypes IIa, IIb, IIc, and IId, Coronaviridae, including Coronaviruses, such as SARS-coronavirus (SARS-CoV), and Toroviruses, Rubella virus, Mumps virus, including the genotypes A, C, D, G, H, and I, Coxsackie virus A including the serotypes 1, 11, 13, 15, 17, 18, 19, 20, 21, 22, and 24 (also known as human enterovirus C; HEV-C), Coxsackie virus B, including subtypes 1-6, Human enteroviruses including, e.g., human enterovirus A (HEV-A, CAV2 to CAV8, CAV10, CAV12, CAV14, CAV16, and EV71) and also including HEV-B (CAV9, CBV1 to CBV6, E1 to E7, E9, E1 to E21, E24 to E27, E29 to E33, and EV69 and E73), as well as HEV, Polioviruses including PV1, PV2, and PV3, Viral encephalitides viruses, including equine encephalitis, Venezuelan equine encephalitis (VEE) (including subtypes IA, IB, IC, ID, IIIC, IIID), Eastern equine encephalitis (EEE), Western equine encephalitis (WEE), St. Louis encephalitis, Murray Valley (Australian) encephalitis, Japanese encephalitis, and tick-born encephalitis, Human herpesviruses, including cytomegalovirus (CMV), Epstein-Barr virus (EBV), human herpes virus-1 (HHV-1), HHV-2, HHV-3, HHV-4, HHV-5, HHV-6, HHV-7, HHV-8, herpes B virus, herpes simplex virus types 1 and 2 (HSV-1, HSV-2), and varicella zoster virus (VZV), HIV-1 including group M (including subtypes A to J) and group O (including any distinguishable subtypes (HIV-2, including subtypes A-E, Epstein-Barr virus (EBV), including subtypes A and B, reovirus, including serotypes and strains 1, 2, and 3, type 1 Lang, type 2 Jones, and type 3 Dearing, Cytomegalovirus (CMV) subtypes include CMV subtypes I-VII, Rhinovirus, including all serotypes, Adenovirus, including all serotypes, filoviruses, including Marburg virus and Ebola virus, and strains such as Ebola-Sudan (EBO-S), Ebola-Zaire (EBO-Z), and Ebola-Reston (EBO-R), arenaviruses, including lymphocytic choriomeningitis (LCM) virus, Lassa virus, Junin virus, and Machupo virus, rabies virus, arboviruses, including West Nile virus, dengue viruses 1 to 4, Colorado tick fever virus, Sindbis virus, Togaviridae, Flaviviridae, Bunyaviridae, Reoviridae, Rhabdoviridae, Orthomyxoviridae, and the like, poxvirus including orthopoxvirus (variola virus, monkeypox virus, vaccinia virus, cowpox virus), yatapoxvirus (tanapox virus, Yaba monkey tumor virus), parapoxvirus, and molluscipoxvirus, Yellow fever, Hantaviruses, including serotypes Hantaan (HTN), Seoul (SEO), Dobrava (DOB), Sin Nombre (SN), Puumala (PUU), and Dobrava-like Saaremaa (SAAV), flaviviruses, including dengue virus, Japanese encephalitis virus, West Nile virus, and yellow fever virus, Measles virus, Human parainfluenzaviruses (HPV), including HPV types 1-56, Influenza virus, including influenza virus types A, B, and C, Influenza A virus subtypes, e.g., swine viruses (SIV): H1N1 influenza A and swine influenza virus, Respiratory syncytial virus (RSV) including subgroup A and subgroup B, Rotaviruses, including human rotaviruses A to E, bovine rotavirus, rhesus monkey rotavirus, and human-RVV reassortments, Polyomavirus, including simian virus 40 (SV40), JC virus (JCV) and BK virus (BKV), Coltiviruses, including Colorado tick fever virus, Eyach virus, Calciviruses, including the genogroups Norwalk, Snow Mountain group (SMA), and Saaporo, Parvoviridae, including dependovirus, parvovirus (including parvovirus B19), and erythrovirus.

The composition of this invention can further comprise one or more than one (e.g., 2, 3, 4, 5, 6, 7, 8, 9, 10, etc.) immunostimulatory agent. Nonlimiting examples of immunostimulatory agents that could be combined with cyclic dinucleotides according to the present invention include the following singly and/or in any combination:

Squalene-based emulsions.
Saponin-based molecules or derivatives.
Immune stimulating complexes (ISCOMs) or derivatives.
Agonists for toll-like receptor 1.
Agonists for toll-like receptors 2 and/or 6, including but not limited to, lipoarabinomannans, lipomannans, lipoteichoic acid, peptidoglycans, diacylated lipoproteins, diacylated lipopeptides, zymosan, Pam2CGDPKHPKSF (FSL-1), Pam2CSK4, Pam3CSK4, and heat-killed bacteria.
Agonists for toll-like receptor 3, including but not limited to, double-stranded RNA, polyadenylic-polyuridylic acid, and polyinosinic-polycytidylic acid.
Agonists for toll-like receptor 4, including but not limited to, lipopolysaccharides, synthetic monophosphoryl lipid A, monophosphoryl lipid A from *Salmonella minnesota* R595, glucopyranosyl lipid adjuvant (GLA), GLA formulated in a stable nano-emulsion of squalene oil-in-water (GLA-SE), and heat-killed bacteria.
Agonists for toll-like receptor 5, including but not limited to, flagellin and heat-killed bacteria.
Agonists for toll-like receptors 7 and/or 8, including but not limited to, single-stranded RNAs (e.g., ORN02, ORN06, ssPoly(U), ssRNA40), imidazoquinolines (e.g., gardiquimod, imiquimod (R837), resiquimod (R848)), thiazoloquinolone derivatives (e.g., CL075), imidazoquinoline derivatives (e.g., CL097), 9-benzyl-8 hydroxyadenine derivatives (e.g., CL264), N-glycinyl[4-((6-amino-2-(butylamino)-8-hydroxy-9H-purin-9-yl)methyl) benzoyl] spermine and derivatives (e.g., CL307, CL347), guanosine analog derivatives (e.g., loxoribine), thymidine homopolymer phosphorothioate ODNs (e.g., polydT), motolimod/VTX-2337, benzoazepine compounds (e.g., TL8-506), 8-hydroxyadenine, N-[4-[(4-amino-2-butyl-1H-imidazo[4,5-c]quinolin-1-yl) oxy]butyl]-octadecanamide, 5-(4-amino-2-methyl-1H-imidazo[4,5-c]quinolin-1-yl)-4,4-dimethyl-2-pentanone, N-[4-(4-amino-2-ethyl-1H-imidazo[4,5-c]quinolin-1-yl)butyl]-methanesulfonamide, and N-[2-[4-amino-2-(ethoxymethyl)-1H-imidazo[4,5-c]quinolin-1-yl]-1,1-dimethylethyl]-methanesulfonamide.

Agonists for toll-like receptor 9, including but not limited to, unmethylated CpG oligodinucleotides (ODNs) (e.g., ODN 1585, ODN 2216, ODN 2336, ODN 1668, ODN 1826, ODN 2006, ODN 2007, ODN BW006, ODN D-SL01, ODN 2395, ODN M362, ODN D-SL03) and bacterial DNA.

Agonists for toll-like receptors 10, 11, and 12.

Agonists for toll-like receptor 13, including but not limited to, rRNA derived oligoribonucleotides (e.g., ORN Sa19).

Agonists of toll-like receptors 2 and 7, including 8-hydroxyadenine conjugated to Pam2C (CL401), 8-hydroxyadenine conjugated to the terminal acid function of Pam2CSK4 (CL413), S-(2,3-bis(palmitoyloxy)-(2RS)propyl)-(R)-cysteinyl-(S)-seryl-(S)-lysyl-Ne-(4-((6-amino-2-(butylamino)-8-hydroxy-9H-purin-9-yl)methyl) benzylamido)(S)-lysyl-(S)-lysyl-(S)-lysine (CL531), and S-(2-myristoyloxy ethyl)-(R)-cysteinyl 4-((6-amino-2-(butylamino)-8-hydroxy-9H-purin-9-yl)methyl) aniline (CL572). Agonists for NOD-like receptors (NLRs), including but not limited to, those against NOD1 (e.g., γ-D-Glu-mDAP (iE-DAP), acylated derivative of iE-DAP (C12-iE-DAP), γ-D-Glu-Lys (iE-Lys), L-Ala-γ-D-Glu-mDAP (Tri-DAP), L-Ala-γ-D-Glu-Lys (Tri-Lys)), those against NOD2 (e.g., muramyl dipeptide (MDP), MDP with a 6-O-acyl derivative with a stearoyl fatty acid (L18-MDP), MurNAc-Ala-D-isoGln-Lys (M-TrisLYS), murabutide, N-Glycolyl-MDP), those against NOD1/2 [MurNAc-L-Ala-γ-D-Glu-mDAP (M-TriDAP), insoluble peptidoglycan from *Escherichia coli* K12 (PGN-ECndi), soluble sonicated peptidoglycan from *Escherichia coli* K12 (PGN-ECndss), insoluble peptidoglycan from *Staphylococcus aureus* (PGN-Sandi), peptidoglycans, γ-D-glutamyl-meso-diaminopimelic acid, lauroyl-γ-D-glutamyl-meso-diaminopimelic acid, L-alanyl-γ-D-glutamyl-meso-diaminopimelic acid, L-alanyl-γ-D-glutamyl-lysine, and γ-D-glutamyl-lysine, muramyl dipeptides and their derivatives, muramyl tripeptides and their derivatives, and murabutide and its derivatives.

Agonists for toll-like receptor 2 and NLRs, including murabutide covalently linked to Pam2C (CL429).

Agonists for RIG-I-Like receptors, including but not limited to, 5' triphosphate double stranded RNA (5'ppp-dsRNA), poly(deoxyadenylic-deoxythymidylic) acid (poly(dA:dT)), and polyinosinic-polycytidylic acid (poly (I:C)).

Agonists for C-type lectin receptors, including but not limited to, β-glucans (e.g., curdlan, laminarin, lichenan, pustulan, schizophyllan, scleroglucan), heat-killed bacteria, whole glucan particles, zymosan, furfurman, and trehalose-6,6-dimycolate and its analogs (e.g., trehalose-6,6-dibehenate).

Agonists for cytosolic DNA sensors, including but not limited to, double-stranded DNA, oligonucleotide containing viral DNA motifs (e.g., HSV-60, VACV-70), non-CpG oligomers (e.g., interferon stimulatory DNA), plasmids entirely devoid of CpG dinucleotides and containing AT-rich regions (e.g., pCpGfree-giant), poly(deoxyadenylic-deoxythymidylic) acid, single-stranded DNA sequence of polydeoxyadenylic acid, and poly(deoxyguanylic-deoxycytidylic) acid.

Other agonists for the stimulator of interferon genes receptor, including but not limited to, cyclic dinucleotides (e.g., 2'3'-cGAMP, 2'2'-cGAMP, c-di-AMP, 2'3'-c-di-AMP, c-di-GMP, c-di-IMP, c-di-UMP) and xanthenone derivatives (e.g., DMXAA).

Inflammasome inducers, including but not limited to, aluminum-based salts (e.g., aluminum potassium sulfate), adenosine 5'-triphosphate (ATP), chitosan, calcium pyrophosphate dihydrate (CPPD) crystals, synthetic heme crystals (e.g., hemozoin), monosodium urate (MSU) crystals, nanoparticles of silica dioxide, nigericin, trehalose-6,6-dibehenate, lipopolysaccharide, poly (dA:dT), flagellin, and any of the aforementioned molecules above. Complement activators, including but not limited to, inulin.

In some embodiments of this invention, a signal peptide can be attached to the particle. Any suitable signal peptide can be used in the particles of the invention. The peptide should be able to target (i.e., mediate entry and accumulation) the particle to a subcellular compartment and/or organelle of interest. Signal peptides are typically about 5 to about 200 amino acids in length. Suitable signal peptides include, e.g., nuclear localization signal peptides, peroxisome-targeting signal peptides, cell membrane-targeting signal peptides, mitochondrial-targeting signal peptides, and endoplasmic reticulum-targeting signal peptides, and trans-Golgi body-targeting signal peptides. Signal peptides may also target the particles to any cell surface receptor including e.g., epidermal growth factor receptors (EGFR), fibroblast growth factor receptors (FGFR), vascular endothelial cell growth factor receptor (VEGFR), integrins, chemokine receptors, platelet-derived growth factor receptor (PDGFR), tumor growth factor receptor, and tumor necrosis factor receptor (TNF).

In some embodiments, a particle of this invention can comprise a targeting functional group or other cell penetrating peptide to penetrate non-phagocytic cells. Nonlimiting examples of targeting functional groups include antibodies, oligopeptides and carbohydrate moieties.

In particular embodiments, an immunostimulatory agent can be attached to, displayed on, and/or encapsulated in the particle. Nonlimiting examples of immunostimulatory agents include mannose, plasmid DNA, oligonucleotides, ligands for toll-like receptors, interleukins and chemokines.

In some embodiments, targeting antibodies can be attached to the particle. Any antibody specific for a target in vivo can be attached to the particle to target and allow particle delivery of the bioactive material.

The present invention further provides a pharmaceutical composition comprising the composition of this invention and a pharmaceutically acceptable carrier.

The composition of this invention can be used in various methods. Thus, the present invention provides a method of inducing an immune response in a subject, comprising administering to the subject an effective amount of the composition of this invention. In particular embodiments, the immune response in the subject can be a humoral, or a Th1 and/or a Th2 cellular response.

Further provided herein is a method of treating a viral infection or preventing a disorder associated with viral infection in a subject, comprising administering to the subject an effective amount of the composition of this invention.

Additionally provided herein is a method of treating a bacterial infection or preventing a disorder associated with bacterial infection in a subject, comprising administering to the subject an effective amount of the composition of this invention.

In further embodiments, the present invention provides a method of treating and/or preventing cancer in a subject in need thereof, comprising administering to the subject an effective amount of the composition of this invention.

Also provided herein is a method of inducing production of interferon and/or a cytokine in a subject in need thereof, comprising administering to the subject an effective amount of a composition of this invention.

Additionally provided herein is a method of treating an autoimmune disorder in a subject in need thereof, comprising administering to the subject an effective amount of a composition of this invention.

In embodiments of the methods above, the composition can be: a) an electrosprayed acetalated dextran nano/microparticle; b) an emulsion acetalated dextran nano/microparticle; c) an electrosprayed polyester nano/microparticle; d) an emulsion polyester nano/microparticle; and e) any combination of (a)-(d).

In the methods described herein, the composition further comprises the TLR7/8 agonist resiquimod.

In the methods described above, the interferon can be type I interferon. Type-I interferon has potent antiviral effects. Induction of endogenous type-I interferon production has considerable therapeutic application for the treatment of acute, and persistent viral infections, including but not limited to hepatitis B virus (HBV) and hepatitis C virus (HCV).

Tumor associated macrophages (TAMs) significantly contribute to tumor microenvironment where they promote tumor progression. TAMs display a plastic M2 phenotype and represent an exciting target for cancer immunotherapy. Hence there is a significant need for, and the present invention provides compounds for use in converting M2 macrophages into M1 cells. Thus, in one embodiment Ace-DEX cGAMP microparticles (MPs) of this invention can be used to switch M2 polarized macrophages towards M1 polarized macrophages for use in cancer immunotherapy, as one nonlimiting example.

In the methods described above, the cytokine can be interleukin-6 (IL-6), IL-12, tumor necrosis factor (TNF), MIP-1α, IP-10, RANTES, or any combination thereof.

The present invention further provides a method of treating an autoimmune disorder in a subject, comprising administering to the subject an effective amount of the composition of this invention. In particular embodiments, the autoimmune disorder is multiple sclerosis.

Any of the methods described herein can further comprise administering an immunostimulatory agent to the subject.

As used herein, the terms "express," "expressing," or "expression" (or grammatical variants thereof) in reference to a gene or coding sequence can refer to transcription to produce an RNA and, optionally translation to produce a polypeptide. Thus, unless the context indicates otherwise, the terms "express," "expressing," "expression" and the like can refer to events at the transcriptional, post-transcriptional, translational and/or post-translational level.

In some embodiments of the present invention, the autoimmune, immune related and/or inflammatory disease or disorder can be, but is not limited to, sepsis; colitis; malignancies; systemic lupus erythematosus (SLE); arthritis, including, but not limited to, rheumatoid arthritis, osteoarthritis, juvenile chronic arthritis, and spondyloarthropathies; systemic sclerosis; idiopathic inflammatory myopathies; Sjögren's syndrome; systemic vasculitis; sarcoidosis; autoimmune hemolytic anemia; autoimmune thrombocytopenia; thyroiditis; diabetes; immune-mediated renal disease; demyelinating diseases of the central and peripheral nervous systems such as multiple sclerosis, idiopathic demyelinating polyneuropathy or Guillain-Barre syndrome, and chronic inflammatory demyelinating polyneuropathy; Alzheimer's disease; myocarditis; kidney disease; obesity; cardiovascular disease; hepatobiliary diseases such as infectious, autoimmune chronic active hepatitis, primary biliary cirrhosis, hepatitis, granulomatous hepatitis, and sclerosing cholangitis; inflammatory bowel disease; gluten-sensitive enteropathy; Whipple's disease; autoimmune or immune-mediated skin diseases including bullous skin diseases, erythema multiforme and contact dermatitis or hypersensitivity; psoriasis; allergic diseases such as asthma, allergic rhinitis, atopic dermatitis, food hypersensitivity and urticaria; immunologic diseases of the lung such as asthma, allergies, COPD (chronic obstructive pulmonary disease), eosinophilic pneumonias, idiopathic pulmonary fibrosis and hypersensitivity pneumonitis; transplantation associated diseases including graft rejection and graft-versus-host-disease; inflammation of the eye including but not limited to retinitis and uveitis; and any/or combination thereof.

A "subject" of this invention includes any subject that is susceptible to the various diseases and/or disorders described herein. Nonlimiting examples of subjects of this invention include mammals, such as humans, nonhuman primates, domesticated mammals (e.g., dogs, cats, rabbits, guinea pigs, rats), livestock and agricultural mammals (e.g., horses, bovine, pigs, goats). In other embodiments, a subject may additionally be an animal such as a bird or reptile. Thus, in some embodiments, a subject can be any domestic, commercially or clinically valuable animal. In particular embodiments, the compositions and methods of this invention have utility in veterinary applications. Subjects may be male or female and may be any age including neonate, infant, juvenile, adolescent, adult, and geriatric subjects. In particular embodiments, the subject is a human. A human subject of this invention can be of any age, gender, race or ethnic group (e.g., Caucasian (white), Asian, African, black, African American, African European, Hispanic, Mideastern, etc.).

A "subject in need thereof" is a subject known to have, or suspected of having, diagnosed with, or at risk of having an autoimmune disease, or an immune related and/or inflammatory disease or disorder. A subject of this invention can also include a subject not previously known or suspected to have an autoimmune, immune related and/or inflammatory disease or disorder or in need of treatment for an autoimmune, immune related and/or inflammatory disease or disorder. For example, a subject of this invention can be administered the compositions of this invention even if it is not known or suspected that the subject has an autoimmune, immune related and/or inflammatory disease or disorder (e.g., prophylactically). A subject of this invention is also a subject known or believed to be at risk of developing an autoimmune, immune related and/or inflammatory disease or disorder.

As used herein, the term "antibody" includes intact immunoglobulin molecules as well as active fragments thereof, such as Fab, F(ab')2, and Fc, which are capable of binding the epitopic determinant of an antigen (i.e., antigenic determinant). Antibodies that bind the polypeptides of this invention are prepared using intact polypeptides and/or fragments containing small peptides of interest as the immunizing antigen. The polypeptide or fragment used to immunize an animal can be derived from enzymatic cleavage, recombinant expression, isolation from biological materials, synthesis, etc., and can be conjugated to a carrier protein, if desired. Commonly used carriers that are chemically coupled to peptides and proteins for the production of antibody include, but are not limited to, bovine serum albumin, thyroglobulin and keyhole limpet hemocyanin. The coupled peptide or protein is then used to immunize a host animal (e.g., a mouse, rat, goat, sheep, human or rabbit). The polypeptide or peptide antigens can also be administered with an immunostimulatory agent, as described herein and as otherwise known in the art.

The terms "antibody" and "antibodies" as used herein refer to all types of immunoglobulins, including IgG, IgM, IgA, IgD, and IgE. The antibody can be monoclonal or polyclonal and can be of any species of origin, including, for example, mouse, rat, rabbit, horse, goat, sheep or human, and/or can be a chimeric or humanized antibody. See, e.g., Walker et al., *Molec. Immunol.* 26:403-11 (1989). The antibodies can be recombinant monoclonal antibodies produced according to the methods disclosed in U.S. Pat. No. 4,474,893 or 4,816,567. The antibodies can also be chemically constructed according to the method disclosed in U.S. Pat. No. 4,676,980. The antibody can further be a single chain antibody (scFv) or bispecific antibody.

Techniques for the production of chimeric antibodies or humanized antibodies by splicing mouse antibody genes to human antibody genes to obtain a molecule with appropriate antigen specificity and biological activity can be used (Morrison et al. 1984. *Proc. Natl. Acad. Sci.* 81:6851-6855; Neuberger et al. 1984. *Nature* 312:604-608; Takeda et al. 1985. *Nature* 314:452-454). Alternatively, techniques described for the production of single chain antibodies can be adapted, using methods known in the art, to produce single chain antibodies specific for the polypeptides and/or fragments and/or epitopes of this invention. Antibodies with related specificity, but of distinct idiotypic composition, can be generated by chain shuffling from random combinatorial immunoglobulin libraries (Burton 1991. *Proc. Natl. Acad. Sci.* 88:11120-3).

Active antibody fragments included within the scope of the present invention include, for example, Fab, F(ab')2, and Fc fragments, and the corresponding fragments obtained from antibodies other than IgG. Such fragments can be produced by known techniques. For example, F(ab')2 fragments can be produced by pepsin digestion of the antibody molecule, and Fab fragments can be generated by reducing the disulfide bridges of the F(ab')2 fragments. Alternatively, Fab expression libraries can be constructed to allow rapid and easy identification of monoclonal Fab fragments with the desired specificity (Huse et al., (1989) *Science* 254:1275-1281).

Monoclonal antibodies can be produced in a hybridoma cell line according to the technique of Kohler and Milstein (*Nature* 265:495-97 (1975)). For example, a solution containing the appropriate antigen can be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in bacterial cell such as *E. coli* by recombinant techniques known to those skilled in the art. See, e.g., W. Huse, (1989) *Science* 246:1275-81.

Antibodies can also be obtained by phage display techniques known in the art or by immunizing a heterologous host with a cell containing an epitope or immunogen of interest.

As used herein, the term "polypeptide" encompasses both peptides and proteins, unless indicated otherwise.

The terms "polypeptide," "protein," and "peptide" refer to a chain of covalently linked amino acids. In general, the term "peptide" can refer to shorter chains of amino acids (e.g., 2-50 amino acids); however, all three terms overlap with respect to the length of the amino acid chain. Polypeptides, proteins, and peptides may comprise naturally occurring amino acids, non-naturally occurring amino acids, or a combination of both. The polypeptides, proteins, and peptides may be isolated from sources (e.g., cells or tissues) in which they naturally occur, produced recombinantly in cells in vivo or in vitro or in a test tube in vitro, and/or synthesized chemically. Such techniques are known to those skilled in the art. See, e.g., Sambrook et al., *Molecular Cloning: A Laboratory Manual 2nd Ed.* (Cold Spring Harbor, N.Y., 1989); Ausubel et al. Current Protocols in Molecular Biology (Green Publishing Associates, Inc. and John Wiley & Sons, Inc., New York).

The term "fragment," as applied to a polypeptide, will be understood to mean an amino acid sequence of reduced length relative to a reference polypeptide or amino acid sequence and comprising, consisting essentially of, and/or consisting of an amino acid sequence of contiguous amino acids identical, or substantially identical, to the reference polypeptide or amino acid sequence. Such a polypeptide fragment according to the invention may be, where appropriate, included in a larger polypeptide of which it is a constituent. In some embodiments, such fragments can comprise, consist essentially of, and/or consist of peptides having a length of at least about 4, 6, 8, 10, 12, 15, 20, 25, 30, 35, 40, 45, 50, 75, 100, 150, 200, or more consecutive amino acids of a polypeptide or amino acid sequence according to the invention.

A fragment of a polypeptide or protein of this invention can be produced by methods well known and routine in the art. Fragments of this invention can be produced, for example, by enzymatic or other cleavage of naturally occurring peptides or polypeptides or by synthetic protocols that are well known. Such fragments can be tested for one or more of the biological activities of this invention according to the methods described herein, which are routine methods for testing activities of polypeptides, and/or according to any art-known and routine methods for identifying such activities. Such production and testing to identify biologically active fragments of the polypeptides described herein would be well within the scope of one of ordinary skill in the art and would be routine.

The term "therapeutically effective amount" or "effective amount," as used herein, refers to that amount of a composition of this invention that imparts a modulating effect, which, for example, can be a beneficial effect, to a subject afflicted with a disorder, disease or cosmetic condition, including improvement in the disease or disorder of the subject (e.g., in one or more symptoms), delay or reduction in the progression of the disease or disorder, prevention or delay of the onset of the disease or disorder, and/or change in clinical parameters of the disease or disorder, as would be well known in the art. The effective amount will vary with the age, general condition of the subject, the severity of the disease, disorder or condition being treated, the particular agent or composition administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation. (See, for example, Remington, *The Science and Practice of Pharmacy* (20th ed. 2000)). For example, a therapeutically effective amount or effective amount can refer to the amount of a composition, compound, or agent that improves a disease or disorder in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

Although individual needs may vary, the determination of optimal ranges for effective amounts of a composition of this invention is within the skill of the art. Human doses can also readily be extrapolated from animal studies (Katocs et al., Chapter 27 In: Remington's Pharmaceutical Sciences, 18.sup.th Ed., Gennaro, ed., Mack Publishing Co., Easton, Pa., 1990). Generally, the dosage required to provide an effective amount of a composition of this invention, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., Chapter 3 In: Goodman & Gilman's The Pharmacological Basis of Therapeutics, 9.sup.th Ed., Hardman et al., eds., McGraw-Hill, New York, N.Y., 1996).

Thus, the amount of the composition or particle of this invention needed to deliver a pharmaceutically effective dosage will vary based on such factors including but not limited to, the polymer solubility, the therapeutic loading capacity and efficiency, the toxicity levels of the polymer, the amount and type of bioactive material needed to effect the desired response, the subject's species, age, weight, and condition, the disease and its severity, the mode of administration, and the like. One skilled in the art would be able to determine the pharmaceutically effective dosage. In general, the amount of composition of this invention that could be administered by the delivery systems of the invention is from about 1 pg to more than about 100 g quantities.

The pharmaceutical compositions according to the present invention may be administered as a single dose or in multiple doses. The pharmaceutical compositions of the present invention may be administered either as individual therapeutic agents or in combination with other therapeutic agents, which when combined may be administered sequentially or simultaneously.

By the terms "treat," "treating" or "treatment of" (or grammatically equivalent terms) it is meant that the severity of the subject's disease or disorder is reduced or at least partially improved or ameliorated and/or that some alleviation, mitigation or decrease in at least one clinical symptom is achieved and/or there is a delay in the progression of the disease or disorder, as would be well known in the art. Thus, in some embodiments, the terms "treat," "treating" or "treatment of" refer only to therapeutic regimens. In other embodiments, the terms "treat," "treating" or "treatment of" (or grammatically equivalent terms) refer to both prophylactic and therapeutic regimens.

The terms "prevent," "preventing" and "prevention" (and grammatical variations thereof) refer to avoidance, prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is delayed and/or is less than what would occur in the absence of the method of the present invention.

An "effective amount," as used herein, refers to an amount that imparts a desired effect, which is optionally a therapeutic or prophylactic effect.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

Pharmaceutical compositions comprising the composition of this invention and a pharmaceutically acceptable carrier are also provided. The compositions described herein can be formulated for administration in a pharmaceutical carrier in accordance with known techniques. See, e.g., Remington, *The Science And Practice of Pharmacy* (latest edition). In the manufacture of a pharmaceutical composition according to embodiments of the present invention, the composition of this invention is typically admixed with, inter alia, a pharmaceutically acceptable carrier.

By "pharmaceutically acceptable carrier" is meant a carrier that is compatible with other ingredients in the pharmaceutical composition and that is not harmful or deleterious to the subject. The carrier may be a solid or a liquid, or both, and is preferably formulated with the composition of this invention as a unit-dose formulation, for example, a tablet, which may contain from about 0.01 or 0.5% to about 95% or 99% by weight of the composition. The pharmaceutical compositions are prepared by any of the well-known techniques of pharmacy including, but not limited to, admixing the components, optionally including one or more accessory ingredients. In certain embodiments, the pharmaceutically acceptable carrier is sterile and would be deemed suitable for administration into human subjects according to regulatory guidelines for pharmaceutical compositions comprising the carrier.

Furthermore, a "pharmaceutically acceptable" component such as a salt, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components include any of the standard pharmaceutical carriers such as phosphate buffered saline solutions, water, emulsions such as oil/water emulsion, microemulsions and various types of wetting agents.

Exemplary modes of administration of the compositions of this invention can include oral, rectal, intranodal, transmucosal, topical, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intraperitoneal, intradermal, intrapleural, intracerebral, intracranial, and intraarticular), topical (e.g., to both skin and mucosal surfaces, including airway surfaces, and transdermal administration, and the like, as well as direct tissue or organ injection (e.g., to liver, skeletal muscle, cardiac muscle, diaphragm muscle or brain). The most suitable route in any given case will depend on the nature and severity of the condition being treated and on the nature of the particular protein, peptide, fragment, nucleic acid and/or vector that is being used.

The compositions of the present invention may be administered to a subject in need of treatment prior to, during or after onset of the disease or disorder. Thus, the compositions of the present invention can be used to treat ongoing immune-related and/or inflammatory diseases or disorders or to prevent diseases or delay the development of immune-related and/or inflammatory diseases or disorders.

In some embodiments, an effective dose or effective amount can comprise one or more (e.g., two or three or four or more) doses of the composition of this invention at any time interval (e.g., hourly, daily, weekly, monthly, yearly, as needed) so as to achieve and/or maintain the desired therapeutic benefit.

The following examples are included to demonstrate various embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention.

EXAMPLES

Example 1: A New Microparticle Platform for a STING-Targeted Adjuvant that Enhances Both Humoral and Cellular Immunity We evaluated the adjuvant activity of a STING agonist, 3'3'-cGAMP (cGAMP), encapsulated in acid-sensitive acetalated dextran (Ace-DEX) polymeric microparticles (MPs) which target antigen-presenting cells for intracellular release. This formulation was superior to all particle-delivery systems tested. It enhanced interferon responses 1000-fold in vitro and 50-fold in vivo over soluble cGAMP. Compared to soluble cGAMP, encapsulated cGAMP caused up to 10-fold increases in antibody titers, enhanced Th1-associated responses, expanded germinal center B cells and memory T cells. It also provided protection against a lethal influenza challenge. Thus encapsulated STING-agonist in microparticles represents a new vaccine adjuvant of humoral and cellular immunity.

Among the many adjuvant candidates in development, considerable interest has been generated over the potential use of interferons (IFNs). IFNs are a class of cytokines produced in response to infection and cancer. IFNs can be broadly categorized by type, with type-I IFNs (IFN-α, IFN-β, IFN-ε, IFN-κ, IFN-ω) binding to the IFN-α/β receptor (IFNAR). Transient expression of type-I IFNs can enhance activation of dendritic cells (DCs) through increasing expression of chemokine receptors, co-stimulatory molecules, and major histocompatibility complex (MHC) class I and class II. Consequently, DC maturation following exposure to IFNs can lead to enhanced priming of protective CD4 and CD8 T cell responses. IFNs upregulate CD69 and CD86 expression on naïve B cells, reduce the threshold for B cell activation, and retain B cells in secondary lymphoid organs, thus increasing the likelihood that they will encounter relevant antigens. IFNs also act on mature B cells, leading to increased germinal center formation and antibody class switching. Finally, IFNs enhance lymphocyte cell division[1] and survival.

As an adjuvant, exogenously-delivered type I IFN, which is applied clinically for treatment of various cancers, viral infections and multiple sclerosis, has many practical drawbacks, including high manufacturing costs and short in vivo half-life. An alternative to exogenous application is to stimulate endogenous type-I IFN production via innate immune receptor, one central one being the stimulator of interferon genes (STING) pathway (a.k.a. MITA, MPYS, ERIS). Cyclic dinucleotides (CDNs) produced by a variety of pathogens or endogenous cytosolic nucleic acid sensor pathways bind to STING. One of these STING activating CDNs is 3'3' cyclic GMP-AMP (cGAMP, also known as guanosine monophosphate-adenosine monophosphate/cyclic [G(3',5') pA(3',5')p]), first identified in *Vibrio cholera*. This ligand binds directly to STING, leading to activation of the downstream effector TANK-binding kinase 1 (TBK-1) which, in turn phosphorylates interferon regulatory factor 3 (IRF3) and IB kinase (IKK), causing transcriptional activation of the type-I IFN and NFκB pathways, respectively.

Although cGAMP and other CDNs represent an exciting novel class of vaccine adjuvants that have generated promising results in early pre-clinical models, CDN delivery is still faced with the formidable physiological plasma membrane barrier that separates extracellular CDNs from their cognate cytosolic STING receptor. To overcome this obstacle, we have encapsulated cGAMP within acetalated dextran (Ace-DEX) polymeric microparticles (MPs), an especially appealing platform for the targeted delivery of cGAMP.

Ace-DEX is derived from dextran, an FDA-approved glucose homopolysaccharide, and is an attractive biomaterial due to its cytocompatibility, tunable biodegradability, and ease of synthesis. Ace-DEX MPs can be fabricated to passively target antigen presenting cells (APCs), since only these cells can internalize material larger than 200 nm. In particular, MPs 1-2 µm in size are engulfed predominantly by CD11c$^+$CD11b$^+$ dendritic cells (DCs). Moreover, Ace-DEX MPs are acid-sensitive and undergo increased degradation rates in the low pH phagolysosomal environment of APCs. Ace-DEX MP degradation rates are tunable by varying the polymer's acetal coverage, which enables optimization of the desired immune response. Here we demonstrate that Ace-DEX cGAMP MP is superior to all encapsulated or adsorbed cGAMP tested, is a potent adjuvant that activates cytokine responses in both mouse and humans cells, causes robust B and T cell responses and provides protection when used in a protein-based influenza vaccine. Furthermore, this formulation can be easily sterilized by radiation without the loss of biologic activity and can be delivered intramuscularly, which is an easy route of delivery used for human vaccines.

Ace-DEX MPs are a Stable and Efficient Platform for the Delivery of cGAMP.

Previous work has demonstrated the usefulness of STING agonists, primarily c-di-GMP, as a vaccine adjuvant, however very high doses (5-140 ug/mouse) are required, rendering it cost-prohibitive for routine use. Since STING resides in the cytosol, a particle delivery system should improve the efficacy. To identify the optimal cGAMP delivery vehicle, we encapsulated cGAMP in a range of particulate systems, including electrosprayed (ES) Ace-DEX MPs, ES poly(lactic-co-glycolic acid) (PLGA) MPs, emulsion (Em) Ace-DEX MPs, and liposomes. We also attempted to use Em PLGA MPs, but cGAMP could not be reliably encapsulated using this method. A complete characterization of each particle formulation was performed (Table 1).

To assess which platform would result in optimal cGAMP bioactivity, murine bone marrow derived dendritic cells (BMDCs) were treated with identical doses of soluble cGAMP, cGAMP encapsulated within the various platforms, or cGAMP delivered using Lipofectamine, a commonly used micelle-based transfection platform. Type-I IFN and IL-6 production were assayed 6 hours later (FIGS. 1A-B). All of the polymer and liposome formulations significantly enhanced cGAMP mediated IFN production over soluble and transfection controls. However, ES Ace-DEX MPs generated the most robust IFN response and were used in all further experiments.

Ace-DEX MPs can passively target APCs based on particle size and allow for triggered and targeted release of cargo within the acidic lysosomal environment. Consistent with these findings, Ace-DEX MPs loaded with fluorescein dye were rapidly taken up by BMDCs and trafficked to the acidic lysosomal compartment.

Figure 8:
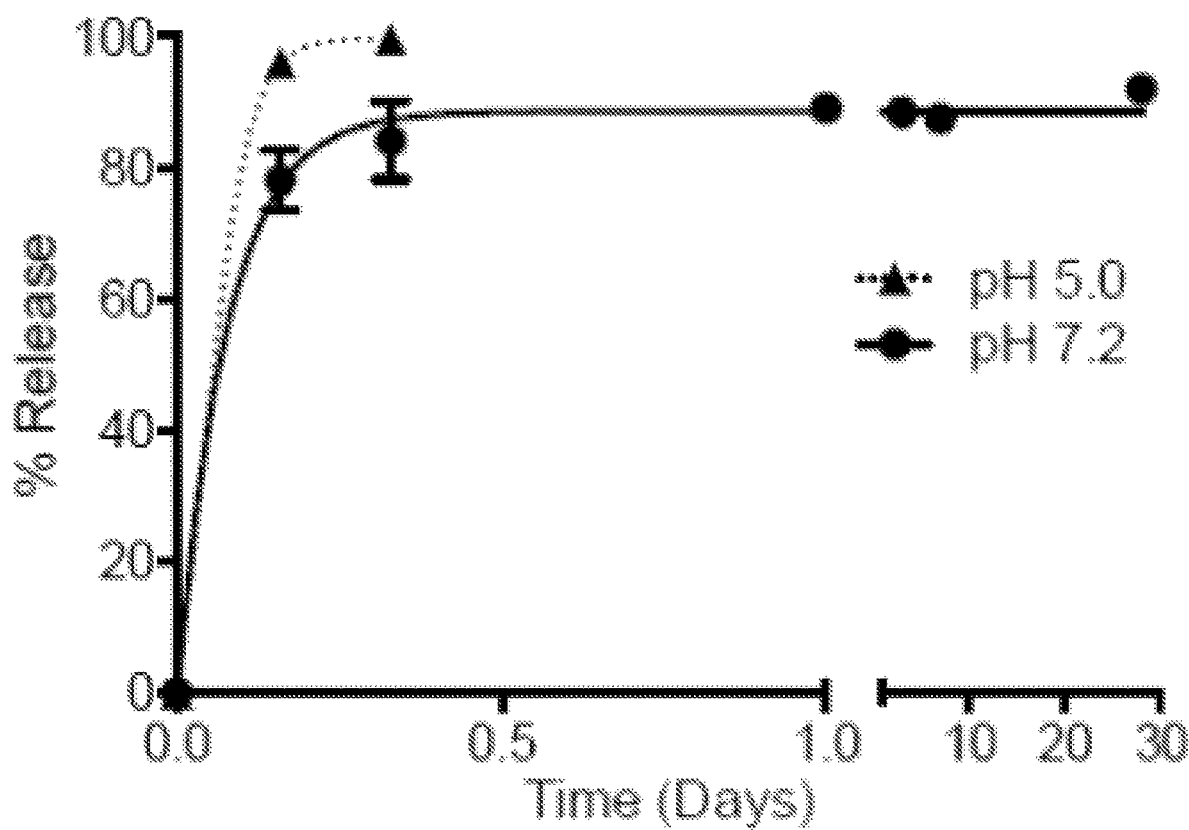
FIG. 8. cGAMP microparticles remain intact under pH neutral physiological conditions for 28 days: Release curve of cGAMP from Ace-DEX microparticles (cGAMP MPs) in RPMI media containing 10% FBS at 37° C. (pH 7.2 or 5.0).

We assessed the cGAMP release kinetics from Ace-DEX MPs at neutral and acidic pH over 28 days in culture media at pH 5.0 and 7.2, representative of the endosomal and extracellular environments, respectively (FIG. 8). At endosomal pH all drug was released within 10 hours. Conversely, a burst release of cGAMP was observed at neutral pH, followed by a plateau of drug release out to 28 days. To assess stability, MPs were incubated for 28 days in media at 37° C., after which particles were intact and the encapsulated cGAMP was still capable of stimulating IFN-β and IL-6 production in BMDCs (FIGS. 1C-D).

Ace-DEX cGAMP MPs are Dose-Sparing, Non-Toxic, and Enhance Immune Activation In Vitro and In Vivo.

Figure 2:
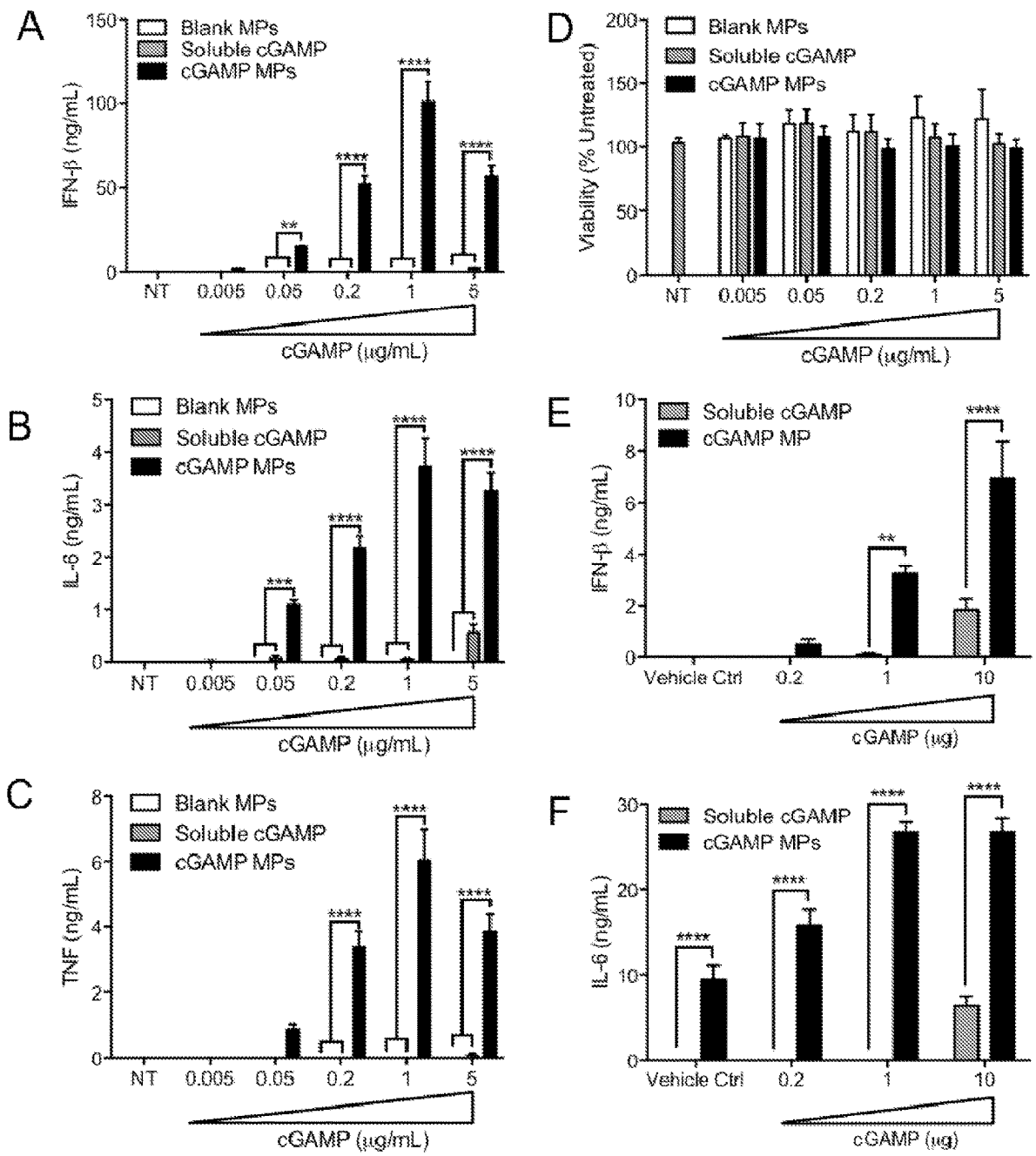
FIG. 2. Microparticle delivery of cGAMP enhances cytokine responses in vitro and in vivo: (A, D) Bone marrow derived dendritic cells from C57BL/6 mice were left untreated (NT) or treated with indicated concentrations of cGAMP delivered as soluble or encapsulated in ES Ace-DEX microparticles (cGAMP MPs), as well as equivalent doses of blank MPs. Supernatants were harvested 6 hours later and subjected to ELISA for (A) IFN-β, (B) IL-6, and (C) tumor necrosis factor (TNF). Cell viability was assessed by MTT assay (n=BMDCs cultured from 3 individual mice±SEM,p<0.01,  p<0.0001). (E, F) C57BL/6 mice were injected intramuscularly (i.m.) with the indicated dose of soluble cGAMP or cGAMP MPs. Alternatively, mice were injected with PBS or blank MPs (Vehicle Ctrl). Six hours later muscle tissue was harvested, and (E) IFN-β and (F) IL-6 concentrations were assessed in tissue homogenates by ELISA (n=5 mice±SD,p<0.01, **** p<0.0001).
Figure 9:
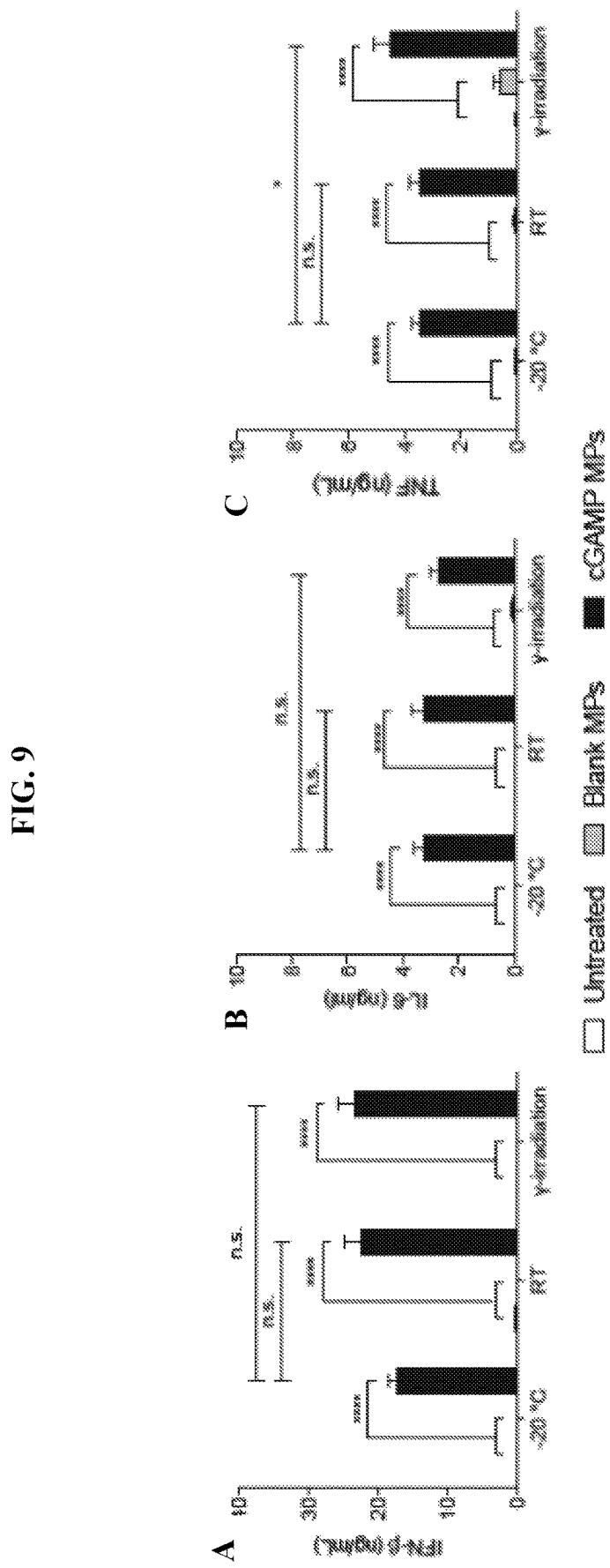
FIG. 9. cGAMP microparticles can be sterilized through gamma irradiation: Bone marrow derived dendritic cells from C57BL/6 mice were treated with 1 μg/mL cGAMP MPs stored at each condition, as well as blank MPs and untreated controls for 6 hours at 37° C. Supernatants were collected and analyzed by ELISA for (A) IFN-β, (B) IL-6, and (C) TNF (n=3 batches of MPs±SEM, *p<0.05, ****p<0.0001).
Figure 10:
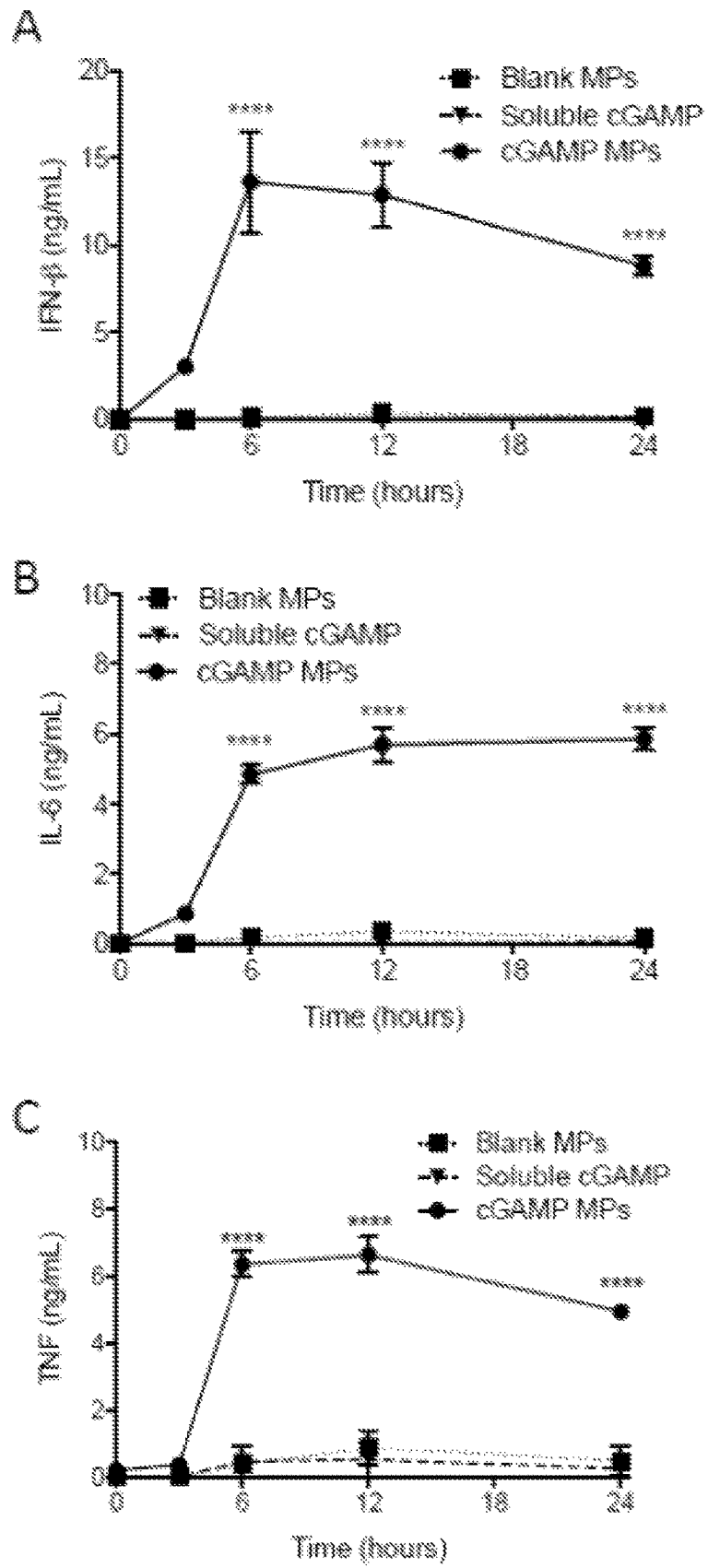
FIG. 10. cGAMP microparticles induced a rapid and sustained cytokine production: Bone marrow derived dendritic cells from C57BL/6 mice were treated with 1 μg/mL soluble cGAMP or cGAMP encapsulated in ES Ace-DEX microparticles (cGAMP MP), or an equivalent dose of blank MPs. Supernatants were harvested at the indicated time point and IFN-β (A), IL-6 (B) and TNF (C) were assessed by ELISA (n=BMDCs cultured from 2 individual mice±SEM, ****p<0.0001).
Figure 11:
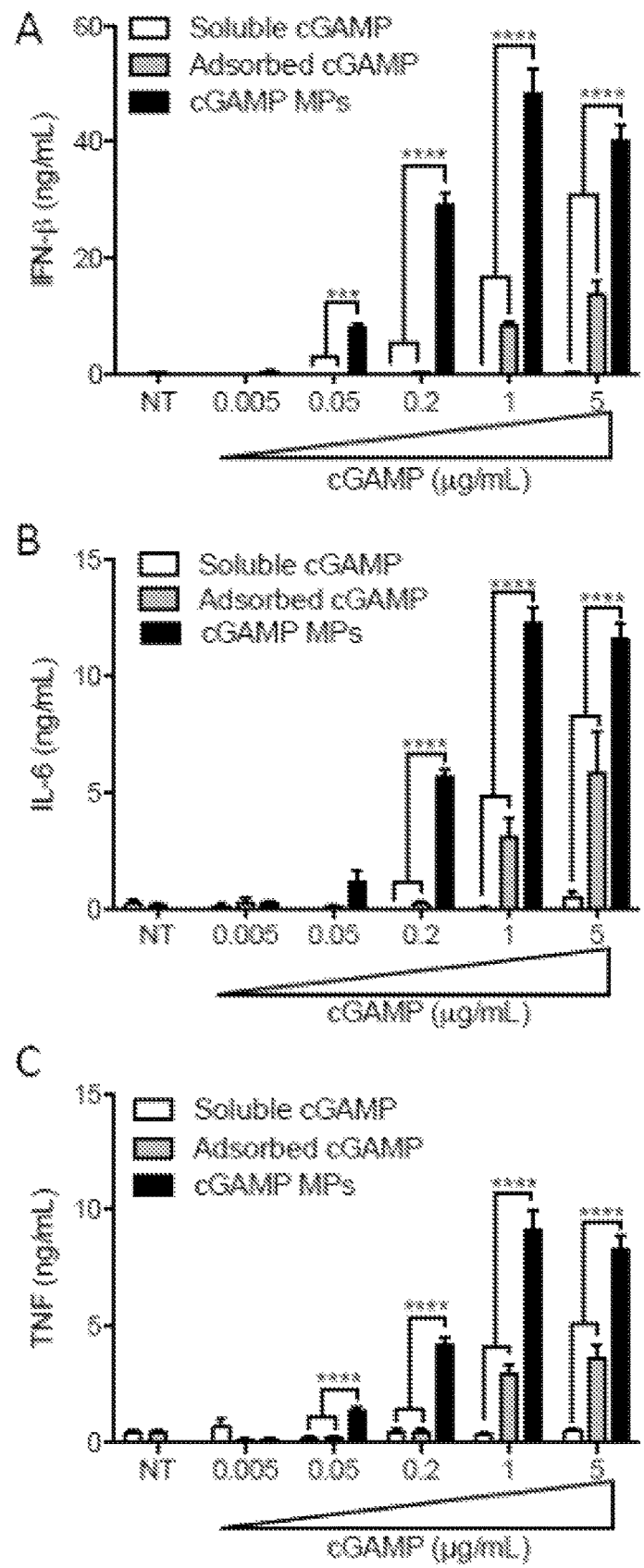
FIG. 11. Encapsulation of cGAMP within Ace-DEX microparticles provides enhanced cytokine responses compared to soluble, or adsorbed cGAMP: Bone marrow derived dendritic cells from C57BL/6 mice were left untreated (NT) or treated with indicated concentrations of cGAMP delivered as soluble, soluble cGAMP adsorbed to blank Ace-DEX microparticles (Adsorbed cGAMP), or encapsulated in ES Ace-DEX microparticles (cGAMP MP). Supernatants were harvested 6 hours later and subjected to ELISA for (A) IFN-β, (B) IL-6, and (C) TNF (n=BMDCs cultured from 3 individual mice±SEM, ****p<0.0001).
Figure 12:
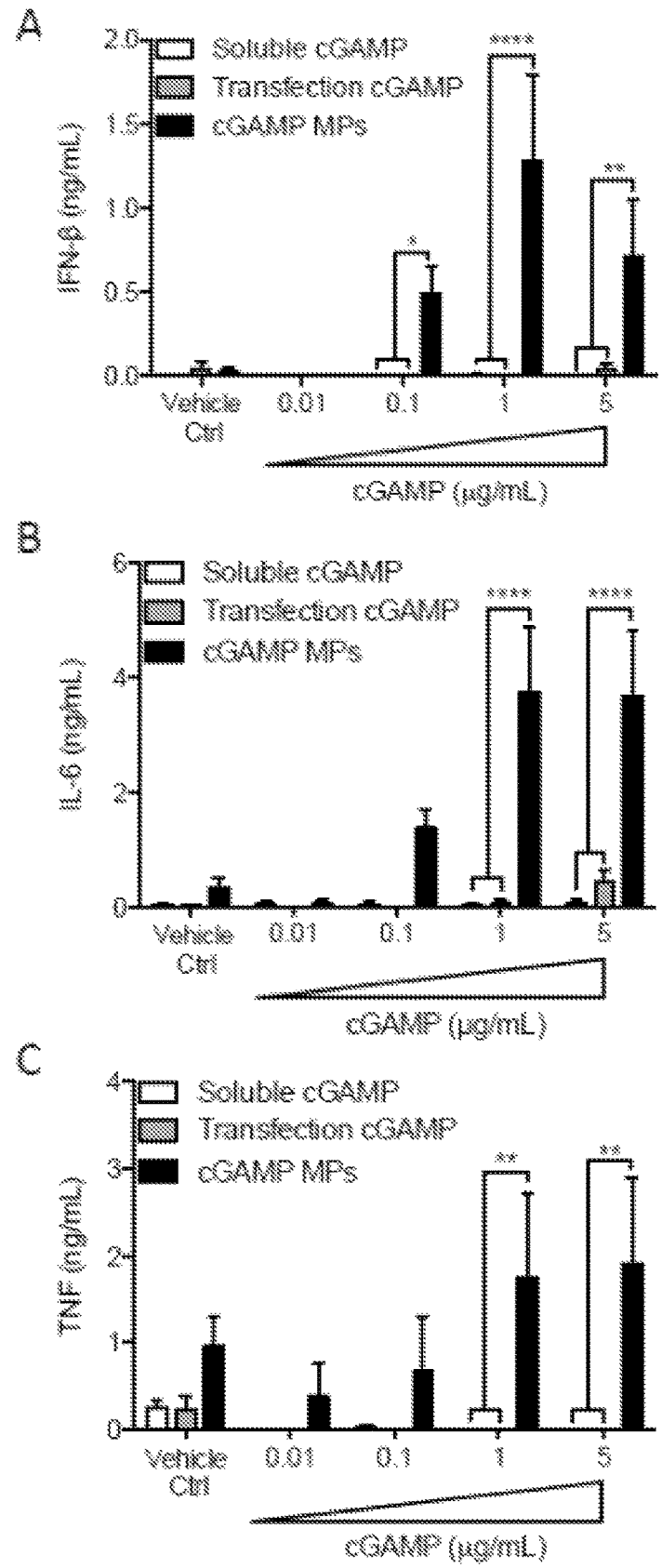
FIG. 12. Microparticle delivery of cGAMP enhances cytokine responses: Peritoneal macrophages from C57BL/6 mice were treated with indicated concentrations of cGAMP delivered as soluble, by Lipofectamine 3000 transfection (Transfection cGAMP), encapsulated in ES Ace-DEX microparticles (cGAMP MPs), or blank MPs control (Vehicle Ctrl). Supernatants were harvested 6 hours later and subjected to ELISA for (A) IFN-β, (B) IL-6, and (C) TNF (n=peritoneal macrophages harvested from 7 individual mice±SEM, *p<0.05, p<0.01, *p<0.001, ****p<0.0001).
Figure 13:
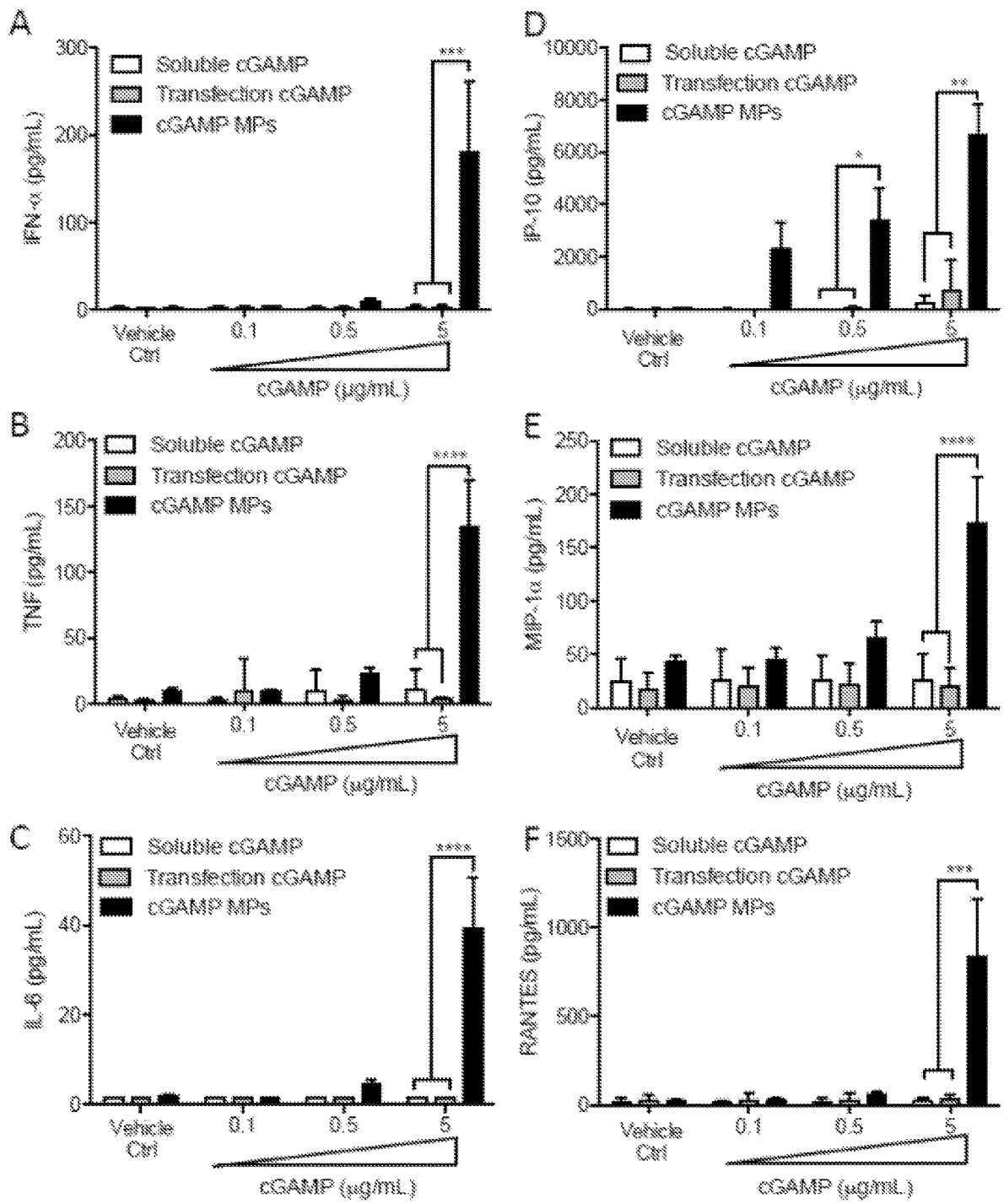
FIG. 13. Microparticle delivery of cGAMP enhances cytokine responses in human dendritic cells: Human dendritic cells were cultured from six donors and treated with indicated concentrations of cGAMP delivered as soluble, by Lipofectamine 3000 transfection (Transfection cGAMP), encapsulated in ES Ace-DEX microparticles (cGAMP MPs), or blank MP control (Vehicle Ctrl). Supernatants were harvested 24 hours later and subjected to Luminex analysis for the indicated cytokines (n=DCs from 6 individual donors±SEM, *p<0.001, **p<0.0001).

BMDCs were treated with various doses of either soluble cGAMP or cGAMP Ace-DEX MPs (hereafter referred to as cGAMP MPs), as well as blank Ace-Dex MP (hereafter referred to as blank MP) controls (FIGS. 2A-C). Soluble cGAMP was unable to induce detectable quantities of pro-inflammatory (TNF and IL-6) or type-I IFN (IFN-β) responses, except at high doses (5 µg/mL). cGAMP MPs resulted in greatly enhanced responses, and provided 100 and 1000-fold dose-sparing compared to soluble cGAMP for pro-inflammatory cytokines and type-I IFN responses, respectively, without inducing any detectable cell death (FIG. 2D). cGAMP MPs subjected to a sterilizing γ-irradiation dose of 25 kGy demonstrated preserved bioactivity (FIG. 9). This indicates an easy approach to sterilize these MP without hampering its biologic activity for potential use in humans. Additionally, storage at room temperature did not affect bioactivity (FIG. 9). A time course study of dendritic cells revealed that cytokine and IFN responses were rapidly induced by cGAMP MPs, and sustained over 24 hours in vitro (FIG. 10). Furthermore, a significant advantage was observed with encapsulation compared to adsorption of cGAMP to the surface of blank MPs (FIG. 11). Similar results were obtained with primary murine peritoneal macrophages, where cGAMP MPs induced dramatically more cytokines than a Lipofectamine transfection reagent (FIG. 12). Additionally, human derived DCs from six individual donors that were treated with cGAMP MPs exhibited greatly enhanced production of type-I IFN, as well as general pro-inflammatory cytokines (TNF and IL-6) and key lymphocyte and leukocyte chemotactants (MIP-1α, IP-10 and RANTES), compared to soluble cGAMP (FIG. 13).

Figure 14:
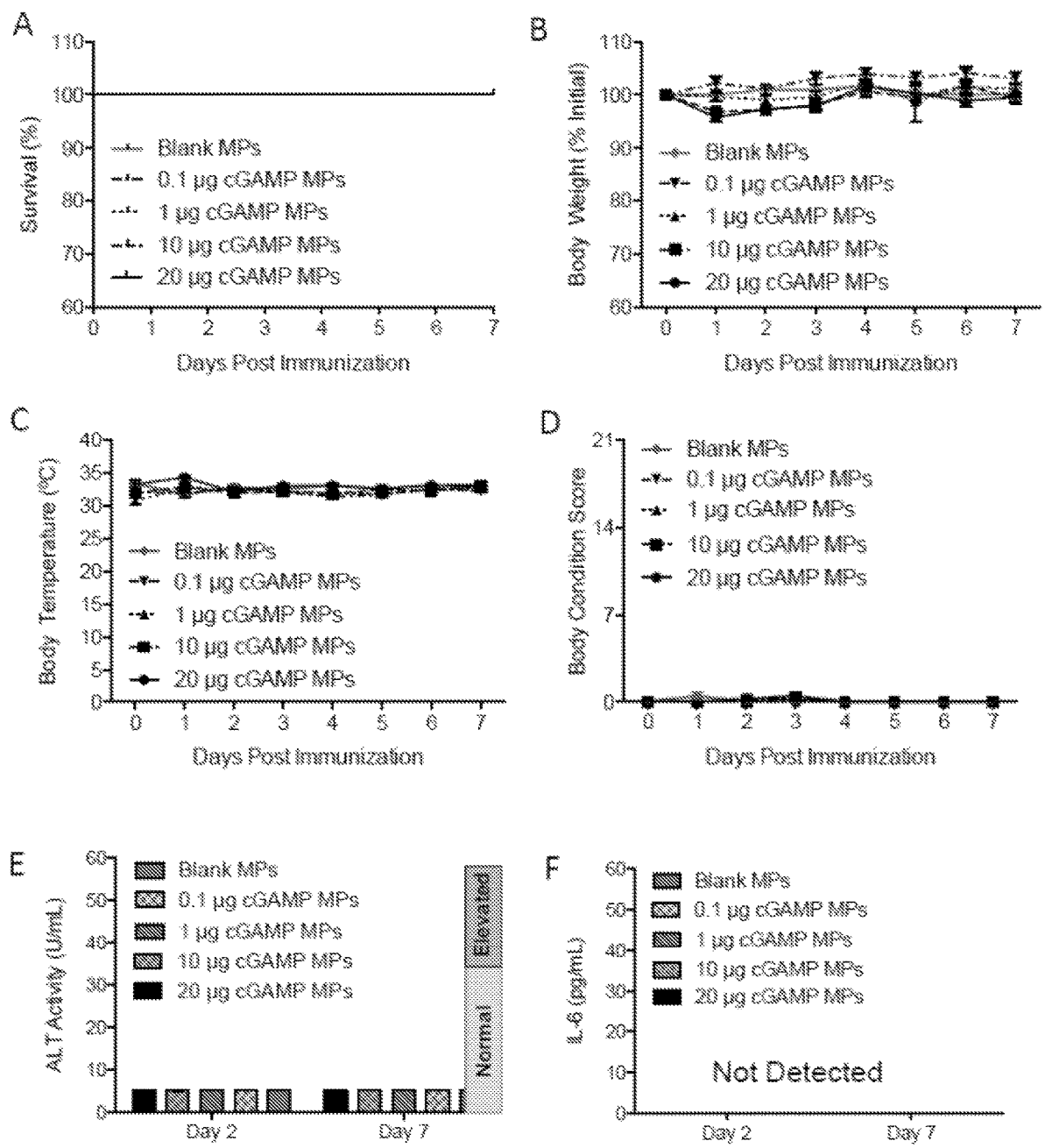
FIG. 14. cGAMP microparticles are not toxic in vivo: C57BL/6 mice were injected i.m. with cGAMP Ace-DEX microparticles (cGAMP MPs) at a final dose of 20, 10, 1, or 0.1 μg of cGAMP. A dose of blank MPs equivalent to 10 μg cGAMP MPs was also injected (Blank MPs). (A) Survival, (B) animal weights, (C) ventral body temperature, and (D) body condition score were tracked daily for one week post injection. Blood was collected 2 and 7 days post immunization and (E) ALT liver enzyme activity, and (F) IL-6 were evaluated. (n=4 mice±SD, all data are non-significant indicating the lack of toxicity).
Figure 25:
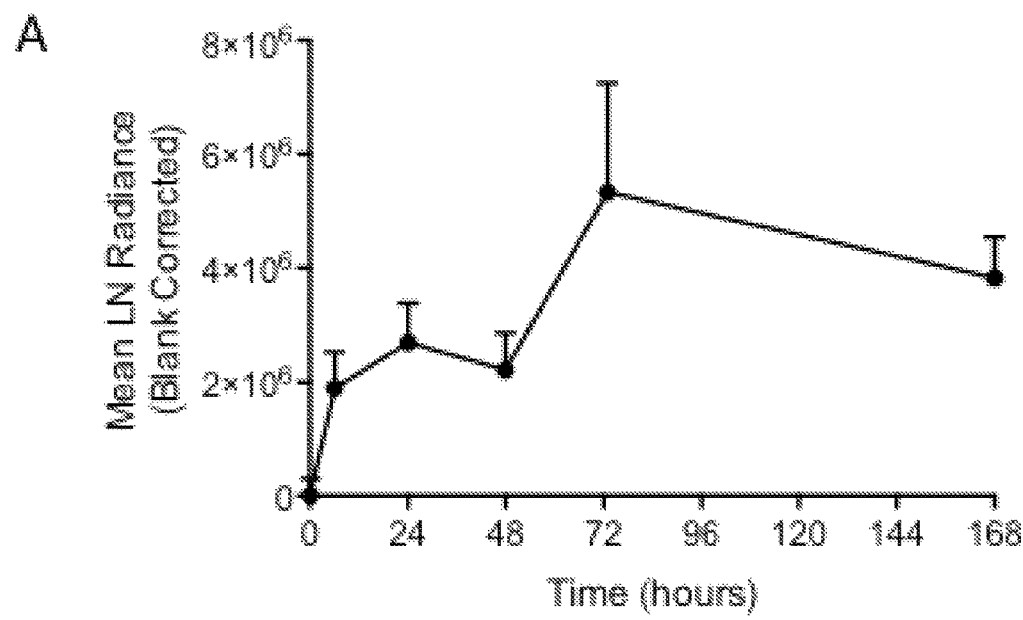
FIG. 25. Ace-DEX MPs traffic to draining lymph nodes following intramuscular injection: Mice were injected i.m. with PBS (time 0) or Texas-Red Ace-DEX particles (10:1 unlabeled dextran: Texas-Red dextran). Fluorescence in the draining inguinal lymph node, as well as the leg in which particles were injected was imaged at the indicated time points using the IVIS-Lumina imaging system. (A) Radiance was quantified in the draining lymph nodes (LN). (B) Representative images on lymph nodes and injection site are shown. (n=6-8±SD)
Figure 25:
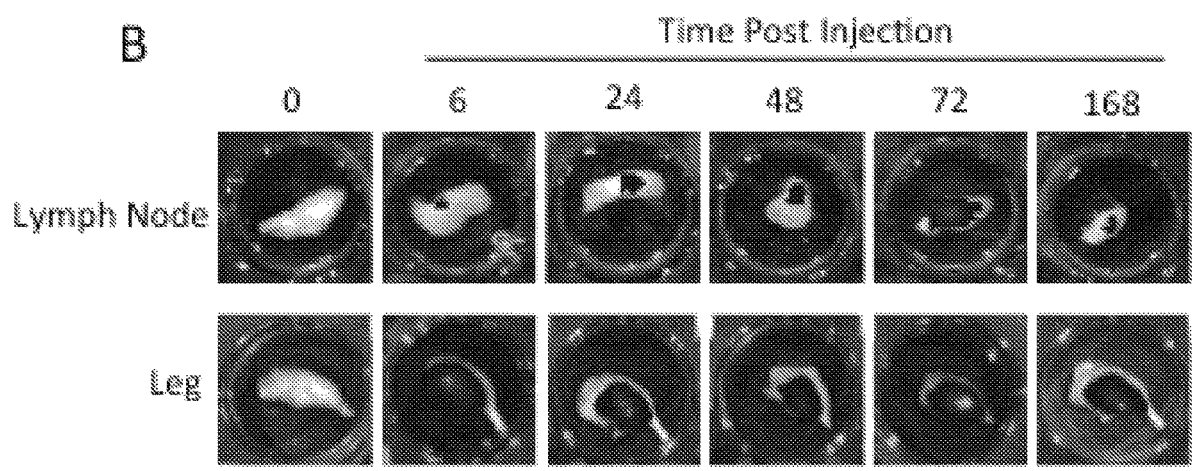

We next tested in vivo biodistribution and potential toxicity of MPs delivered via a route that is used for human immunization. In order to monitor trafficking of Ace-DEX MPs following injection, particles were sprayed using a 10:1 ratio of unlabeled to Texas red labeled acetalated dextran. Biodistribution was then assessed in a preclinical mouse model employing an intramuscular (i.m.) route of administration. Following the injection organs were harvested at set time points and fluorescence was measured by IVIS imaging. Particles were detected at the injection site in the leg throughout the course of the study, and trafficked to the draining inguinal lymph node, peaking 72 hours post injection (FIG. 25). No particles were detected in the liver, spleen, kidneys, lung, heart, thymus, brain, or the inguinal lymph node from the flank opposite the injection site, indicating that the particles were localized to the injection site and immediate draining lymph node, and did not disseminate systemically. To assess toxicity, mice were injected with blank MPs, or cGAMP MPs at doses up to 20 μg cGAMP and monitored for one week. No mortality, weight loss, changes in body temperature, deteriorating body condition, or increase in serum ALT activity or IL-6 concentration were observed (FIG. 14). Local immune activation in muscle tissue was assessed in animals 6 hours after injection with either soluble cGAMP or MPs with various cGAMP weight loadings (FIGS. 2E-F). As with in vitro studies, cGAMP MPs profoundly enhanced local type-I IFN and IL-6 responses in vivo to achieve dose sparing compared to soluble cGAMP. While blank MPs did not induce type-I IFN, they did induce detectable IL-6. However, a dose dependent increase of IL-6 was still observed following cGAMP MP treatment. TNF levels were not detected above background.

cGAMP MPs Induce a Potent Humoral Response to a Model Antigen Independent of MP Dose.

Figure 3:
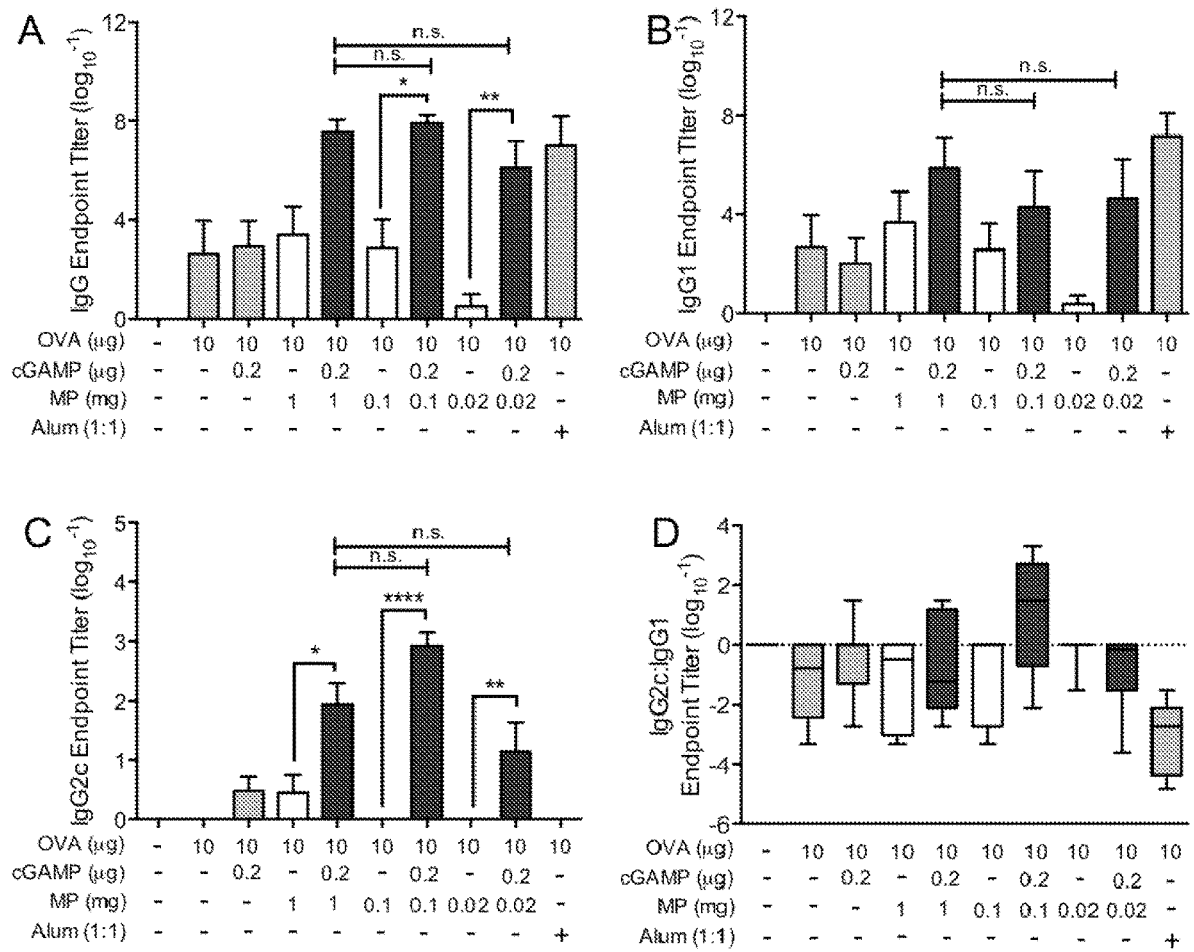
FIG. 3. cGAMP microparticles enhance humoral immune response independent of particle dose: C57BL/6 mice were injected i.m. on days 0 and 21 with PBS, or soluble ovalbumin (OVA, 10 µg) alone or combined with soluble cGAMP (0.2 µg), cGAMP microparticles (MP) (0.2 µg cGAMP in 1-0.02 mg MP), blank MPs (1-0.02 mg) or Alhydrogel 2% (Alum, 1:1 by volume). Serum was collected on day 28 and assayed for OVA specific (A) total IgG titers, (B) IgG1 titers, (C) IgG2c titers, and (D) IgG2c:IgG1 isotype skewing (n=6-10 mice±SEM pooled from two separate experiments, *p<0.05, p<0.01, *p<0.001, ****p<0.0001).

To control for particle-dose effects, Ace-DEX MPs were prepared with various cGAMP weight loadings that allowed for delivery of a fixed cGAMP dose (0.2 fig) in varying amounts of Ace-DEX MPs (0.02-1 mg). Equivalent doses of blank MPs were also tested. Each of the six MP groups was combined with a model antigen, soluble ovalbumin (OVA). In addition, other mice were immunized with soluble OVA alone, soluble OVA delivered with a conventional adjuvant (alum), or soluble OVA with soluble cGAMP. OVA specific antibody titers were assessed seven days after the day 21 boost. While the low concentration of soluble cGAMP did not induce substantial OVA specific total IgG levels over OVA alone, encapsulation of cGAMP in Ace-DEX MPs greatly enhanced these titers by $10^4$ to $10^6$ (FIG. 3A). A level of antigen specific total IgG, equivalent to soluble OVA or soluble cGAMP alone, was observed with higher doses (>0.1 mg) of Blank MPs but wanes at the low 0.02 mg dose of MP. At this low dose of particles and in the presence of OVA, cGAMP MPs yielded >$10^6$-fold increase in titers compared to blank MPs and $10^3$-fold increase compared to soluble cGAMP. cGAMP MPs resulted in titers that were similar to the conventional strong humoral adjuvant alum, independent of the MP dose.

The impact of cGAMP MPs on antibody isotype skewing between Th2-associated IgG1 (FIG. 3B) and Th1-associated IgG2c (FIG. 3C) was next assessed. While IgG1 titers closely reflected total IgG levels described earlier, IgG2c was detected only when OVA was delivered with soluble cGAMP, cGAMP MPs, and the highest dose of blank MPs. At all particle doses, cGAMP MPs induced significantly higher anti-OVA IgG2c titers than blank MP. Most notably, at the medium (0.1 mg) dose of particles, MP alone did not induce any IgG2c, while cGAMP MPs enhanced IgG2c titers to $10^3$. An examination of the IgG2c:IgG1 ratio indicated that while alum skewed towards Th2-associated IgG1, soluble and encapsulated cGAMP yielded a more balanced distribution of IgG isotypes or even a Th1-associated IgG2c response (FIG. 3D).

cGAMP MPs Induce an Antigen Specific T Cell Response.

Figure 4:
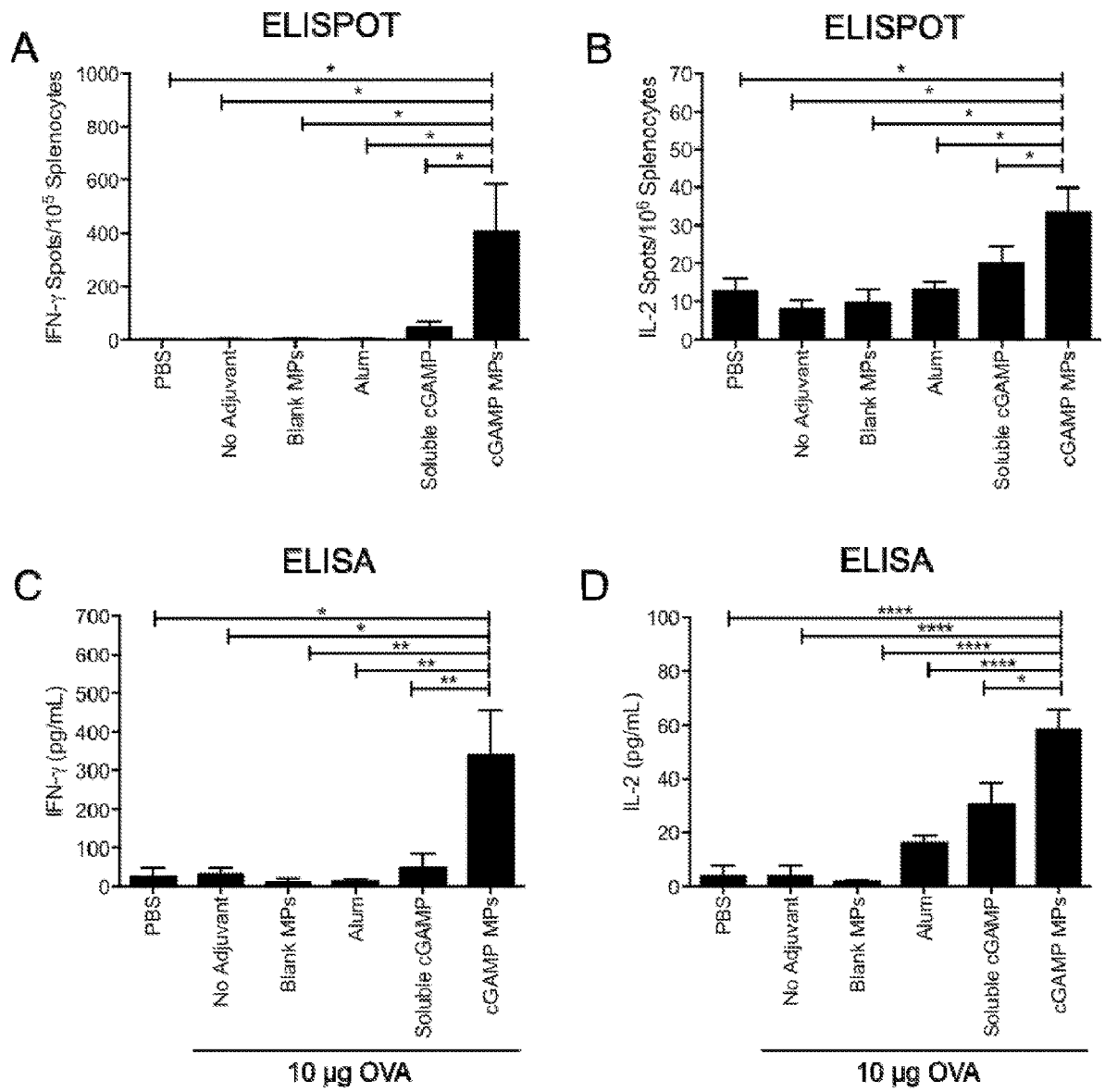
FIG. 4. cGAMP microparticles enhance T cell responses: C57BL/6 mice were injected i.m. on days 0, 21 and 35 with PBS or soluble ovalbumin (OVA, 10 µg) alone or combined with soluble cGAMP (0.2 µg), cGAMP microparticles (cGAMP MP, 0.2 µg cGAMP delivered in 0.65 mg MPs), Blank MPs, or Alhydrogel 2% (Alum, 1:1 by volume). Splenocytes were harvested on day 42 and restimulated with CD8 restricted OVA peptide (SIINFEKL, 10 µg/mL) for 36 hours. (A) IFN-γ, or (B) IL-2 specific T cells were quantified by ELISPOT. Alternatively, splenocytes were re-stimulated using whole OVA protein (10 g/mL) for 36 hours. Supernatants were evaluated by ELISA for (C) IFN-γ, or (D) IL-2 (n=3-5 mice±SEM, representative of two individual experiments. *p<0.05, p<0.01, **p<0.0001).

To assess the impact of cGAMP MPs on cellular immunity, mice were immunized with OVA alone or OVA in combination with blank MPs, 0.2 μg of soluble or Ace-DEX encapsulated cGAMP, or alum. Mice received a prime and two boosts with the same formulation (21 and 35 days later). On day 42, splenocytes were stimulated with the CD8 restricted OVA peptide (SIINFEKL) (FIGS. 4A-B) or whole OVA protein (FIGS. 4C-D). T cell responses were assessed by IFN-γ and IL-2 ELISPOT (FIGS. 4A-B), as well as by ELISA (FIGS. 4C-D). IFN-γ and IL-2 positive spots were significantly increased in cGAMP MP treated splenocytes compared to all other groups. Soluble cGAMP induced a small increase in all of these measurements. Similar results were observed with total cytokine levels following re-stimulation with whole protein (FIGS. 4C-D). These results indicate the cGAMP MPs are inducers of IFN-γ and IL-2 expressing T cells in addition to antibody responses.

cGAMP MP Vaccination Generates a Strong Influenza-Specific Antibody Response.

Figure 5:
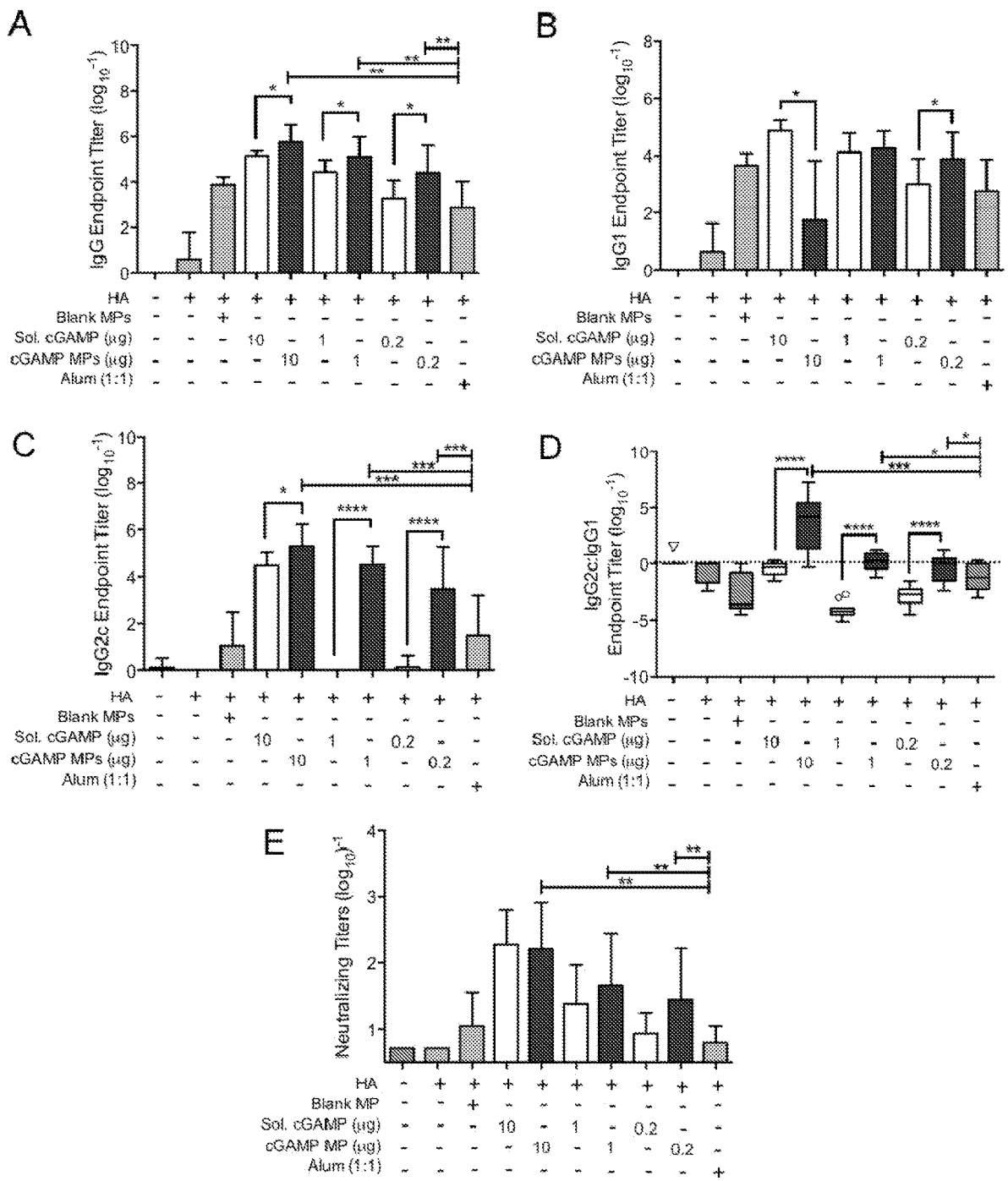
FIG. 5. cGAMP microparticles enhance Influenza specific humoral immune response: C57BL/6 mice were injected i.m. on days 0 and 21 with PBS, or soluble hemagglutinin (HA, 1 µg) alone or combined with soluble cGAMP (Sol. cGAMP, 10-0.2 µg), cGAMP microparticles (cGAMP MP, 10-0.2 µg cGAMP in 1 mg MPs), Blank MPs, or Alhydrogel 2% (Alum, 1:1 by volume). Serum was collected on day 28 and assayed for HA specific (A) total IgG titer, (B) IgG1 titer, (C) IgG2c titer, (D) IgG2c:IgG1 isotype skewing and (E) neutralizing titers (n=12-13 mice±SEM, *p<0.05, p<0.01, *p<0.001, ****p<0.0001).

We next tested cGAMP MP in a viral model. As MP dose did not impact cGAMP MPs' efficacy in the model OVA vaccine, 1 mg of particles was used per injection to allow evaluation of a broader range of cGAMP doses (0.2-10 μg). Mice were immunized with HA influenza protein (strain A/Puerto Rico/8/1934 H1N1 (PR8)) alone or in combination with control blank MPs, indicated doses of cGAMP MPs, soluble cGAMP, or alum. Following a boost on day 21, HA antibody titers were assessed on day 28 (FIG. 5A). Total HA specific IgG was induced by both soluble and cGAMP MPs in a dose dependent fashion. cGAMP MPs increased antibody titers between 9 to 41-fold over soluble cGAMP. It also generated total IgG titers greater than both alum and the blank MP control.

Similar trends noted in the OVA studies were also observed with the anti-HA IgG1 (FIG. 5B) and IgG2a (FIG. 5C) titers. Soluble cGAMP and alum favored Th2-associated IgG1 isotypes, whereas cGAMP MPs profoundly promoted Th1-associated IgG2a production up to $10^5$-fold over soluble cGAMP (FIG. 5C). A comparison of the IgG2c:IgG1 ratio revealed that cGAMP MPs favored a balanced Th1:Th2 response and an even more Th1 skewed response at the 10 μg encapsulated cGAMP dose (FIG. 5D).

In order to assess functional neutralizing capacity of antibodies elicited by each treatment, neutralizing titers were assessed against PR8 influenza virus (FIG. 5E). While no significant difference was observed between soluble and encapsulated cGAMP, all MP groups produced high levels of neutralizing antibodies that were significantly greater than the levels exhibited with alum. However, neutralizing titers did not correlate with survival outcomes.

cGAMP MPs Expand Germinal Center B Cell, and Memory T Cell Populations.

Figure 6:
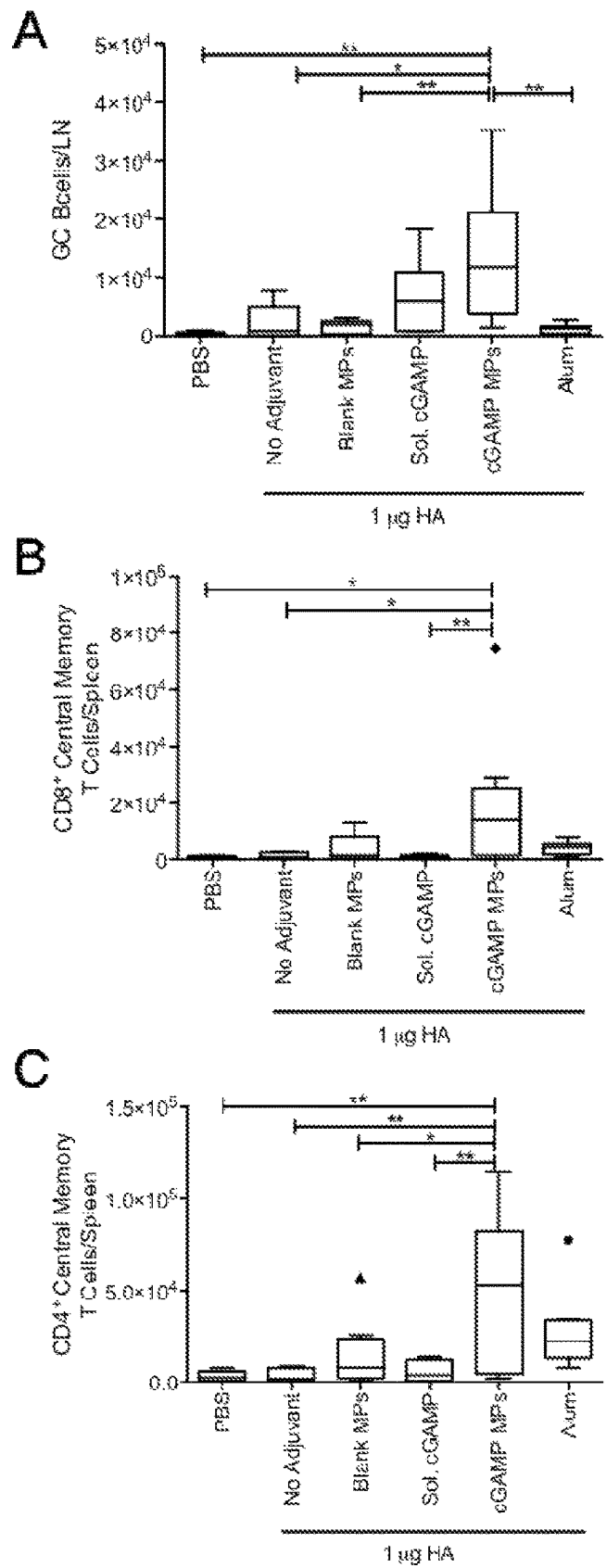
FIG. 6. cGAMP microparticles expand germinal center B cells and central memory T cells: C57BL/6 mice were injected i.m. on days 0 and 21 with PBS, or soluble hemagglutinin (HA, 1 µg) alone or combined with soluble cGAMP (Sol. cGAMP, 10 µg), cGAMP microparticles (cGAMP MPs, 10 µg cGAMP in 1 mg MPs), Blank MPs, or Alhydrogel 2% (Alum, 1:1 by volume). (A) Lymph nodes were collected on day 35 and analyzed for total germinal center B cells (CD19$^+$CL7$^+$CD95$^+$). (B, C) Spleens were collected and analyzed for total central memory CD4$^+$ and CD8$^+$ T cells (CD4/CD8$^+$CD62$^{hi}$CD44$^{hi}$) (n=6-10 mice±SEM pooled from two individual experiments, *p<0.05, **p<0.01).

We next assessed the impact of cGAMP MPs immunization on specific lymphocyte populations. cGAMP MPs (10 μg cGAMP) significantly increased the $CD19^+GL7^+CD95^+$ germinal center B cell population in the draining (inguinal) lymph nodes 14 days post boost compared to alum and blank MPs. The cGAMP MPs were also trending higher than soluble cGAMP. In the spleen, total populations of $CD62^{hi}CD44^{hi}$ central memory CD4 and CD8 T cells were significantly expanded following HA immunization coupled with cGAMP MPs compared to soluble cGAMP (FIG. 6).

cGAMP MP Vaccination Protects Against Lethal Influenza Challenge.

Figure 7:
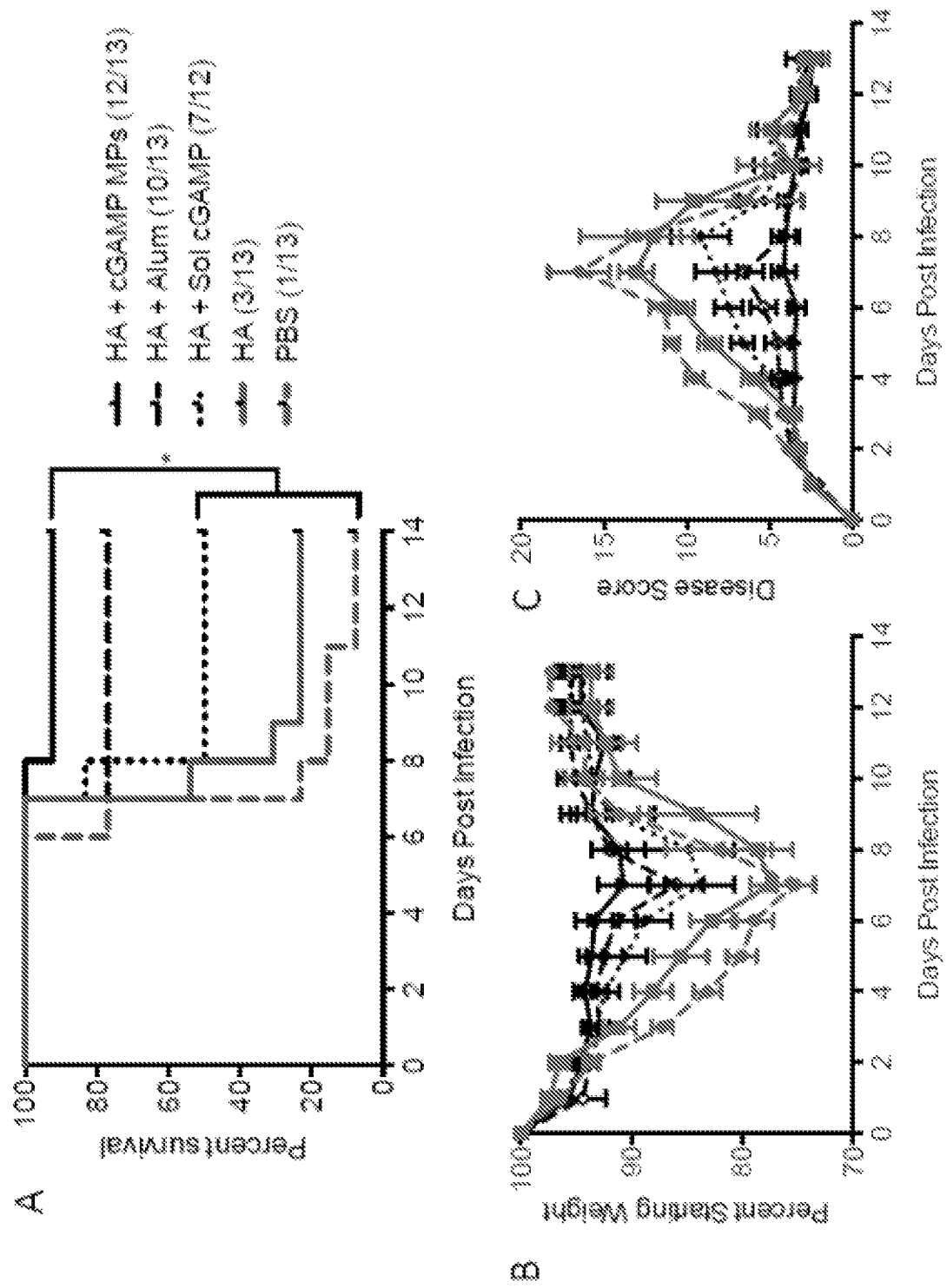
FIG. 7. cGAMP microparticles protect against lethal Influenza infection: 8 week old female C57BL/6 mice were immunized with PBS, or soluble hemagglutinin (HA, 1 µg) from strain A/Puerto Rico/8/1934/H1N1 alone or combined with soluble cGAMP (Sol cGAMP, 0.2 gig), cGAMP microparticles (cGAMP MP, 0.2 µg cGAMP in 1 mg MP) or Alhydrogel 2% (Alum, 1:1 by volume). A boost was administered 21 days later. One month post-boost mice were infected intranasally with 1000 ffu of A/Puerto Rico/8/1934/H1N1. (A) Survival, (B) weight loss and (C) body condition score were assessed daily for 14 days (n=12-13 mice, *p<0.05).

To assess whether a cGAMP MP vaccine is protective against influenza infection, mice were vaccinated with a subset of the above groups, boosted on day 21, and then challenged one month later with a lethal dose (1000 ffu) of PR8 influenza virus. Survival, weight loss and disease score were monitored for 14 days post infection (FIG. 7).

Twelve of thirteen animals vaccinated with HA plus cGAMP MPs were protected from a lethal challenge that killed greater than 90% of unvaccinated mice and greater than 75% of animals vaccinated with the unadjuvanted formulation (FIG. 7A). Soluble cGAMP demonstrated modest 50% protection that was significantly lower than the protection offered by the cGAMP MP formulation. Alum also provided a lower level of protection than cGAMP MPs. In addition to increased survival, cGAMP MP vaccinated animals displayed the least weight loss and the lowest disease scores, which is a composite of multiple body condition criteria (FIGS. 7B-C).

The use of recombinant antigen-based influenza vaccines offers a number of advantages over conventional killed or attenuated vaccine formulations. First, recombinant influenza antigens can be produced quickly and safely (e.g., FluBlok), without the need for the time consuming process of influenza production in eggs, thus enabling a more rapid response to emerging strains. Second, recombinant vaccines allow for rational antigen design; for example, universal influenza antigens such as HA stalk protein or the extracellular domain of influenza Matrix protein (M2e) could be used. The major drawback of recombinant vaccines, however, is poor antigen immunogenicity. Adjuvants have been used extensively to overcome this barrier, but influenza adjuvants (i.e., MF59, AS03) are universally Th2 skewing, which leads to a lack of IFN production and effective long-lasting antiviral immunity.

To date, high manufacturing costs of recombinant IFN, and the lack of safe and effective commercially available IFN-inducing adjuvants, has hampered thorough analysis of the adjuvant effects of type-I IFNs. The recent emergence of the cGAS-STING pathway as a central regulator of type-I IFN response has resulted in the discovery of a new class of CDNs that presents promising IFN-inducing vaccine adjuvants. However, given the cytosolic localization of cGAS and STING, and the high manufacturing costs of CDNs, efficient intracellular delivery and dose-sparing is critical if they are to become viable adjuvant candidates.

To this end, we examined multiple particulate platforms in an attempt to increase intracellular cGAMP delivery. All four platforms examined were able to induce significant IFN production at low doses of adjuvant, supporting the hypothesis that particulate delivery of cGAMP greatly enhances its activity. This is consistent with previous reports regarding c-di-GMP delivery via lipid nanoparticles or liposomes. However, the liposome and emulsion platforms have notable drawbacks. Liposomes have long-term stability issues and are typically fabricated by multi-step, batch techniques. A double emulsion followed by solvent evaporation is also a batch method, and water-soluble small molecule cargo like cGAMP can be easily lost to the continuous outer water phase, decreasing encapsulation efficiency. In addition, emulsion MPs can be difficult to produce in an aseptic environment required for human use. On the other hand, electrospray is a continuous method that fulfills several crucial criteria for a MP fabrication process, highlighted by its ability to efficiently encapsulate cargo, be scaled-up, and create relatively monodisperse MPs. Furthermore, we have demonstrated that Ace-DEX cGAMP MPs can be effectively sterilized using γ-irradiation and stored at room temperature without impacting the immunological activity of the MPs. These characteristics could help clear major manufacturing and application hurdles by removing the need for aseptic production and cold chain storage. With regard to enhanced storage stability, we have previously demonstrated that cargo encapsulated within Ace-DEX MPs has preserved activity for at least 90 days when stored at elevated temperatures.

In addition to these advantages, ES Ace-DEX cGAMP MPs proved to be the most potent vehicle for induction of type-I IFN and IL-6. This improved efficacy may be attributed to the polymer's acid-sensitivity, resulting in rapid MP degradation, triggered release of the cargo within the acidic environment of the phagolysosome, and subsequent endosomal escape via an osmotic swelling mechanism. Although PLGA is attractive because of its biocompatibility and biodegradability, it is very slow-degrading and shows minimal release of its payload within acidic environments. This could help to explain why Ace-DEX MPs outperformed PLGA MPs made through identical methods. In support of this hypothesis, antigen cross-presentation is significantly enhanced through encapsulation in Ace-DEX MPs relative to encapsulation in PLGA MPs. Finally, degradation of PLGA MPs produces acidic byproducts that could be potentially detrimental to vaccine outcomes.

We observed that Ace-DEX cGAMP MPs were safe and potent inducers of type-I IFN and cytokine responses both in vitro and in vivo where they provided greater than 1000 and 50-fold drug dose-sparing, respectively. Vaccination with cGAMP MPs promoted CD4 and CD8 effector and memory cells and Th1-associated IgG2c production, as well as protected against a lethal influenza challenge. Thus, cGAMP MPs represent a promising new vaccine adjuvant ideally suited for recombinant protein vaccines.

Our findings indicate that neutralizing titers were not strongly correlated with weight loss, disease score, or days survived post challenge, suggesting that immune mechanisms other than direct virus neutralization critically contributed to protection induced by cGAMP MPs. Antibody dependent cell-mediated cytotoxicity (ADCC) has emerged as an important component of a protective response to influenza infection and is mediated primarily by NK cells which kill virus infected cells through interactions between FcγRIIIa and virus specific IgG2 subtypes.

While the Ace-DEX cGAMP MPs examined here proved to be extremely effective both at inducing a type-I IFN response and protecting against a lethal influenza virus challenge, the cGAMP release profile indicated that the majority of MP-encapsulated drug quickly diffused into the surrounding aqueous environment. These findings clearly identify the need for more sustained delivery and also highlight further untapped potential of the platform. Given that much of the drug was released within the first 10 hours, it is possible that the observed effects are due to the remaining particle-associated drug. If this were the case, the dose-sparing values of Ace-DEX cGAMP MPs reported herein could be greatly underestimated.

While the current study examines the application of Ace-DEX cGAMP MPs as a subtype specific influenza vaccine adjuvant, this formulation has great potential for multiple applications. First of all, in contrast to virus neutralizing antibodies, influenza specific antibodies capable of mediating ADCC tend to be broadly cross-reactive. Hence, given the strong skewing towards IgG2c observed following cGAMP MP immunization, the potential of this vaccine to induce ADCC and cross protection against heterosubtypic infection, particularly in conjunction with rational immunogen design. In addition, the 'plug and play' nature of these Ace-DEX cGAMP MPs in combination with diverse recombinant antigens is a significant advantage of this platform. Finally, while only soluble antigens were explored in this study, encapsulation of both recombinant vaccine antigens and a cGAMP adjuvant could further improve the efficacy of Ace-DEX delivered vaccines. The utility of these MPs also could extend well beyond the realm of vaccination against infectious diseases. Induction of a potent type-I IFN response has the potential to result in significant anti-viral and anti-tumor therapeutic activity.

In conclusion, encapsulation of cGAMP within Ace-DEX MPs is a highly efficient and scalable system for the production of potent inducers of type-I IFN, and pro-inflammatory cytokine responses both in vitro and in vivo. We demonstrate that these particles produce balanced Th1/Th2 mediated humoral and cellular immune responses, and provide significant dose-sparing compared to soluble cGAMP. Finally, we provide a proof of principle that Ace-DEX cGAMP MPs protect against lethal influenza infection in an animal model. Together these results demonstrate that Ace-DEX cGAMP MPs could represent an effective and commercially viable vaccine adjuvant.

Reagents for Synthesis of cGAMP MPs:

All materials used for MP fabrication were purchased from Sigma Aldrich, unless otherwise indicated. Vaccine grade 3'3'-cGAMP was purchased from Invivogen (San Diego, Calif.).

Synthesis of Ace-DEX:

Ace-DEX was synthesized using 71 kDa (average molecular weight) dextran from *Leuconostoc mesenteroides*[2]. After rapidly hydrolyzing the polymer in 10% v/v deuterium chloride in deuterium oxide, its relative cyclic acetal coverage was determined to be 40±3% using $^1$H-NMR spectroscopy on an Inova 400 MHz spectrometer (Varian Medical Systems, Palo Alto, Calif.).

cGAMP MP Fabrication by Electrospray:

ES cGAMP MPs (Ace-DEX and PLGA, 85:15) were fabricated by a coaxial electrohydrodynamic spraying method using a customized stainless steel needle (Rame-Hart Instrument Co., Succasunna, N.J.). The MPs were collected on a stainless steel plate (McMaster Carr, Elmhurst, Ill.). The needle and plate were charged with opposite polarities using high voltage power sources (Gamma High Voltage Research, Inc., Ormond Beach, Fla.). Egg phosphatidylcholine (Avanti Polar Lipids, Alabaster, Ala.) was added post-fabrication to increase the water-suspendability of the MPs. cGAMP MP Fabrication by Double Emulsion Solvent Evaporation: The emulsion cGAMP MPs were fabricated using a water-in-oil-in-water emulsion solvent evaporation method.

cGAMP Liposome Formulation:

The fabrication of liposomes was modified as described. Briefly, a 100:1 (weight ratio) mixture of hydrogenated (soy)L-α-phosphatidylcholine (PC) and 1,2-dioleoyl-3-trimethyl-ammonium-propane (DOTAP) was dissolved in chloroform and dried by a rotary evaporator (Buchi R-200) to form lipids film. The dry film was then reconstituted in a Krebs-Henseleit (K-H) buffer for 45 min in a 60° C. water bath with cGAMP. Liposomes were freeze-thawed three times, followed by consecutively extruding them through polycarbonate membrane filters 6 times with an Avanti Mini-Extruder/Heating Block. Free drug were removed by passing through a disposable PD-10 column (GE Healthcare). Sucrose was added to the eluted liposome solution, which was rapidly frozen at −80° C. before lyophilization.

Endotoxin Testing:

The endotoxin content of all formulations was measured. All MPs had an endotoxin content of less than 0.25 EU/mg, within the recommended level for preclinical subunit vaccine formulations.

Scanning Electron Microscopy:

MPs were placed on carbon tape attached to aluminum pin stubs (Ted Pella, Inc., Redding, Calif.) and sputter-coated with 10 nm of AuPd using a Sputter Coater 108 Auto attached to a Thickness Monitor MTM-10 (Cressington Scientific Instruments, Hertfordshire, United Kingdom). Electron micrographs were acquired using an S-4700 scanning electron microscope (Hitachi High Technologies America, Schaumburg, Ill.) operating at an accelerating voltage of 2.0 kV.

Quantification of cGAMP MP Loading:

cGAMP loading was determined using high performance liquid chromatography (HPLC). cGAMP MPs were suspended in HPLC-grade water, and dichloromethane at a 1:1 v:v was then added. This mixture was vigorously vortexed for 2 minutes and then centrifuged for 45 minutes at 15,000×g (4° C.). An aliquot of the water phase was injected into an isocratic 80/20 v/v water/methanol mobile phase operating at 0.6 mL/hr. After passing through an Aquasil C18, 150×4.6 mm (Thermo Fisher Scientific, Waltham, Mass.) column, the absorbance of the eluent was measured at 256 nm. A standard curve of cGAMP dissolved in water was subjected to the same conditions, and the cGAMP loading in the MPs (µg cGAMP/mg solids) was determined. Blank MPs subjected to the same process were used as a background correction.

MP Sizing and Zeta Potential:

Each particle formulation was separately suspended in deionized water, and their hydrodynamic size (z-average, nm) and zeta potential (kV) were acquired using a Zetasizer Nano Z (Malvern Instruments Ltd, Malvern, United Kingdom). The reported data are the mean of three values determined by a minimum of ten readings each.

cGAMP Release in Media:

cGAMP MPs were suspended in RPMI media (Life Technologies) and RPMI media made acidic using hydrochloric acid (pH 5.0) at 37° C. on a shaker plate operating at 200 rpm. At predetermined timepoints, aliquots were removed, centrifuged (30 min at 21,000×g, 4° C.), and washed with 1 mL water made basic (0.02% v/v trimethylamine in water). The washed pellets were subjected to the same process as the protocol used to determine cGAMP loading in the MPs. Blank MPs collected at each timepoint were used for background subtractions.

Gamma Irradiation:

Soluble and Ace-DEX cGAMP MPs were stored at −20° C. or room temperature for 39 hours. Alternatively, MPs were subjected to a 25 kGy γ-irradiation dose using a collimator (Model 335) with a $^{137}$Cesium γ-ray source at a dose of 2.2 Gy/min (Model Mark I-68; J.L. Shepherd & Associates, San Fernando, Calif., USA) over the course of 39 hours.

Cell Preparation:

Murine BMDCs used in MP stimulation and co-culture systems were prepared from C57BL/6 mice. Human DCs were generated from patients enrolled in a clinical trial after providing informed consent. The cells were provided as de-identified samples prior to use in the described study. Primary human dendritic cells were generated by culture of CD34$^+$-selected cells from peripheral blood in the presence of Stem Cell Factor (SCF; 50 ng/mL), Flt3L (100 ng/mL), and GM-CSF (800 U/mL) for 72 hours. The pre-DCs were expanded in GM-CSF (800 U/mL Leukine™ Genzyme, Cambridge, Mass.) and IL-4 (500 U/mL) in AIM V medium (GIBCO® AIM V® Medium CTS™, ThermoFisher Scientific, Waltham, Mass.) with 10% human AB serum (Gem-Cell™, Gemini Bioproducts, West Sacramento, Calif.) for 12-14 days in 6 well cluster plates (CoStar #3471, Corning, N.Y.). SCF, Flt3L, IL-4 were obtained from Peprotech, Rocky Hill, N.J.

ELISA and Luminex:

ELISA kits for murine IL-6 and TNF were purchased from BD Biosciences (San Jose, Calif.) and IFN-γ was purchased from BioLegend (San Diego, Calif.). All ELISAs were performed according to manufacturers' instructions. IFN-β was detected by ELISA using murine specific IFN-β antibodies from Santa-Cruz Biotechnology (sc-57201; Dallas, Tex.) and R&D Systems (32400-1; Minneapolis, Minn.), anti-Rabbit IgG HRPO from Cell Signaling Technology (7074; Danvers, Mass.) and recombinant IFN-β standard from R&D Systems (12401-1).

Analysis of cytokines in human DC samples was performed by assaying 25 µL of supernatants in the Human Cytokine custom 13-Plex Luminex Bead Panel (EMD Millipore, St. Charles, Mo.) according to manufacturer's instructions.

Cell Viability:

Cell viability was determined by MTT assay.

Animals and Immunization:

All studies were conducted in accordance with National Institutes of Health guidelines for the care and use of laboratory animals and approved by the Institutional Animal Care and Use Committee at the University of North Carolina (UNC). All animals were maintained in specific pathogen-free facilities at UNC and were between 8 and 15 weeks of age. Age and sex matched C57BL/6 mice were obtained from Jackson Laboratory (Bar Harbor, Me.).

Mice were immunized on days 0, and 21, as well as 35 where indicated. Intramuscular (i.m.) injections were performed with phosphate buffered saline (PBS; Life Technologies), 10 µg of low endotoxin ovalbumin (OVA, Invivogen) or 1 g of recombinant hemagglutinin (HA) from influenza stain A/Puerto Rico/8/1934 H1N1 (Protein Sciences) plus the indicated formulations of soluble cGAMP and/or MPs. Alum controls were injected with antigen plus Alhydrogel 2% (Invivogen) mixed at a 1:1 ratio by volume. The alum dose was 0.25 mg.

In Vivo Cytokines:

Mice were immunized i.m. with 0-10 µg cGAMP delivered in 0.8-1 mg of particles. Six hours later mice were euthanized and quadriceps were collected and homogenized in PBS containing 2 µg of protease inhibitor per mg of muscle tissue, then centrifuged at 12,000×g for 10 minutes. Supernatants were collected and cytokine production was assessed by ELISA.

In Vivo Evaluation of Safety:

Mice were immunized i.m. with 1.12 mg of blank MPs (equivalent to 10 µg dose of cGAMP), or 0.1, 1, 10 or 20 µg of cGAMP encapsulated within Ace-DEX MPs at a loading of 8.9 µg cGAMP/mg MP. Serum was collected 2 and 7 days post immunization and assessed for IL-6 by ELISA, and ALT using an ALT activity assay (Cayman Chemicals, Ann Arbor, Mich.) according to the manufacturers' instructions. Survival, body weight, ventral body temperature, and body condition was monitored daily for 7 days. Body condition score is a composite of activity, posture, physical appearance, appetite, hydration, weight loss, and body temperature.

ELISPOT and T Cell Re-Stimulation:

Splenocytes were isolated from mice immunized as described above. IFN-γ and IL-2 ELISPOTs were performed according to manufacturer's instructions (eBioscience, San Diego, Calif.) using $2\times10^5$ and $2\times10^6$ splenocytes, respectively, stimulated with 10 µg/mL SIINFEKL peptide (Anaspec, Fremont, Calif.) for 36 hours. Plates were dried and spots were quantified using an ELISPOT Reader System (AID, Strassberg, Germany). Alternatively $2\times10^5$ splenocytes were stimulated with 10 µg/mL whole OVA protein for 36 hours. Supernatants were collected and analyzed for IFN-γ and IL-2 by ELISA.

Cells and Influenza Viruses:

Madin-Darby Canine Kidney (MDCK) cells London Strain (Influenza Reagent Resources, FR-58) were maintained in Dulbecco's Modified Eagle's Medium with glucose, L-glutamine, penicillin/streptomycin, and heat inactivated fetal bovine serum (Gibco, Carlsbad, Calif.). Influenza virus strain H1N1 A/Puerto Rico/08/1934 (PR8; Charles River, North Franklin, Conn.) was propagated in embryonated specific pathogen free-chicken hen eggs (Sunrise Farms Inc., Catskill, N.Y.) and harvested as clarified and sequentially filtered allantoic/amniotic fluid.

Influenza Microneutralization (MN) Assay:

Influenza endpoint neutralization titers were determined using an adaptation of the CDC/WHO influenza MN assay similar to as previously described. Two-fold serial dilutions of heat-inactivated sera (starting input 1:10) were incubated with ~100 tissue culture infectious dose 50% units of infectious influenza virus in a 96-well plate. Neutralization reactions were then seeded with MDCK cells and incubated at 37° C. 5% $CO_2$ for 18-22 hours and subsequently assay plates were fixed with 80% acetone in phosphate-buffered saline (PBS). Influenza virus infected MDCK cells were detected immunocytochemically. Briefly, plates were sequentially blocked with avidin (Life Technologies-Molecular Probes, Eugene, Oreg.) and biotin (Sigma-Aldrich, St. Louis, Mo.) in PBS, incubated for one hour with 1:6000 each MAB8257B and MAB8258B (EMD Millipore, Temecula, Calif.), incubated for 30 minutes with 1:4000 streptavidin-HRP (BD Biosciences, San Jose, Calif.) developed using o-Phenylenediamine dihydrochloride dissolved in phosphate-citrate buffer with sodium perborate (Sigma-Aldrich, St. Louis, Mo.) and quenched with a 0.5N solution of sulfuric acid. Absorbance was measured at an optical density (OD) of 490 nm using a Synergy H1 microplate reader (BioTek Instruments Inc., Winooski, Vt.). Batch controls including virus input quantification, analysis of a type-specific hyperimmune antisera (positive control), and mouse strain matched normal sera (negative control) were included with all runs to facilitate evaluation of assay performance. The 50% virus neutralization signal cutoff was calculated from virus and cell only controls included on each assay plate as described. The neutralization endpoint titer for a given sample was reported as the reciprocal of the highest serum dilution at which an $OD_{490} \leq 50\%$ of the calculated neutralization signal cutoff was observed. Seroconversion is defined as a ≥4-fold change in endpoint titer or a change from <10 to ≥40.

Antigen Specific Endpoint Binding Titer (ELISA):

Antigen specific serum antibody binding titers (endpoint) were determined by standard ELISA similar to previously described methods. Two-fold serial dilutions of test sera were performed in 384-well plates coated with influenza HA protein (A/Puerto Rico/08/34 (Protein Sciences Corporation, Meriden, Conn.)) or ovalbumin (Invivogen) at 2.5 μg/mL and blocked for two hours at room temperature using carbonate bicarbonate buffer with 3% (w/v) non-fat dry milk. Plates were incubated overnight at 4° C. then washed four times with PBS plus 0.1% Tween-20. Horseradish peroxidase-conjugated anti-Mouse Ig specific antibodies (Southern Biotech, Birmingham, Ala.) were added to plates at a 1:4,000 dilution. Plates were then incubated at room temperature for two hours and washed four times. TMB peroxidase substrate solution (KPL, Gaithersburg, Md.) was then added to the plates. Following 10 minutes at room temperature, 2N $H_2SO_4$ solution (Sigma, St. Louis, Mo.) was added to stop the reaction. The plates were read at an optical density (OD) of 450 nm using a Perkin Elmer Victor3 plate reader (Perkin Elmer, Waltham, Mass.). The endpoint was set at three times the average plate background OD. Log endpoint titer is reported as the log of the reciprocal of the highest serum dilution at which the OD value was equal to or greater than endpoint.

Influenza Infection and Animal Monitoring:

C57BL/6 mice were immunized as described above, on day 0 and 21. One month after their final boost mice were sedated via i.p. injection of Tribromoethanol (Avertin). Mice were infected intranasally with 1000 ffu of influenza strain A/Puerto Rico/8/1934 H1N1 in 0.9% sterile saline solution in a total volume of 20 μL, followed by a 10 μL saline wash. Animals were monitored daily for survival, body weight and body condition (a composite measure of activity level, appearance, posture, hydration, ventral body temperature, body weight and appetite). Moribund animals were humanely euthanized in accordance with guidelines set for by the Animal Care and Use Committee at the University of North Carolina (UNC).

Statistical Analysis:

Statistical analyses for antibody titers were performed in R using the Wilcoxon rank sum test. All remaining statistical analyses were performed with GraphPad Prism version 6 software. Analysis of groups was performed as indicated in figures. All data points were included in the analyses, and no outliers were excluded in calculations of means or statistical significance.

Example 2: cGAMP MPs Synergize with PAMPs to Induce Diverse Cytokine Profiles

Figure 15:
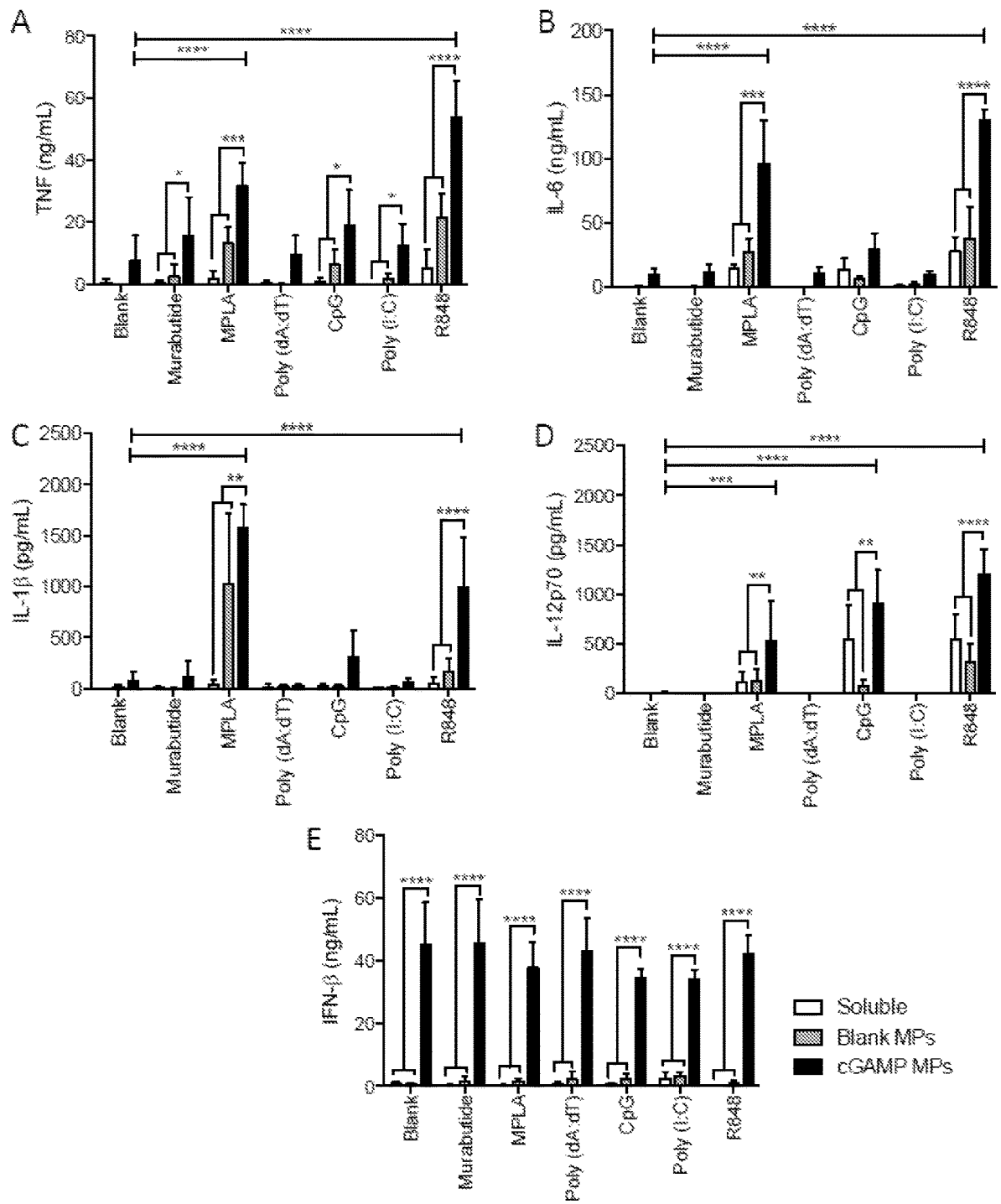
FIG. 15. cGAMP Microparticles synergize with various PAMPs to induce diverse cytokines. Bone marrow derived dendritic cells (BMDCs) from C57BL/6 mice were harvested, and used on culture day 9. Cells were deprived of growth factors overnight, then left untreated (Blank) or treated with soluble Murabutide (10 ug/ml), MPLA (1 ug/mL), Poly (dA:dT) (10 ug/mL), CpG (1 ug/mL), Poly (I:C) (10 ug/mL) or R848 (0.01 ug/mL) alone or in combination with cGAMP MPs (1 ug/mL total cGAMP), or an equivalent amount of Blank MPs. Cell supernatants were collected 22 hours later and were analyzed for TNF (A), IL-6 (B), IL-1β (C), IL-12p70 (D) and IFN-3 (E). Dashed lines indicate upper limit of detection for cytokine ELISAs. (n=4±SEM, *p<0.05, p<0.01, *p<0.001, ****p<0.0001)

Previously, we have demonstrated that Ace-DEX cGAMP MPs are potent inducers of type-I interferon response, as well as select pro-inflammatory cytokines (FIGS. 15A, B and E). However cGAMP MPs alone fail to induce a subset of cytokines known to be beneficial for influenza vaccine outcomes, including interleukin-12 (IL-12) and interleukin-1β (IL-β) (FIGS. 15C and D). In order to elicit a broader cytokine profile, murine BMDCs were treated with blank, or cGAMP MPs alone, or in combination with a variety of PAMPs currently under examination as vaccine adjuvant candidates. Among the PAMPs tested, MPLA (TLR2/4 agonist) and R848 (TLR7/8 agonist) showed the greatest synergy. In combination with cGAMP MPs, both PAMPs synergized to induce significant levels of IL-1β and IL-12p70 which were not achieved with either cGAMP MPs or PAMP alone. Furthermore, cGAMP MPs plus either R848 or MPLA significantly enhanced production of IL-6 and TNF. These data demonstrate synergy between cGAMP MPs and either MPLA or R848. As R848 resulted in the most robust responses, future studies focused on the cGAMP MP/R848 combination.

Figure 16:
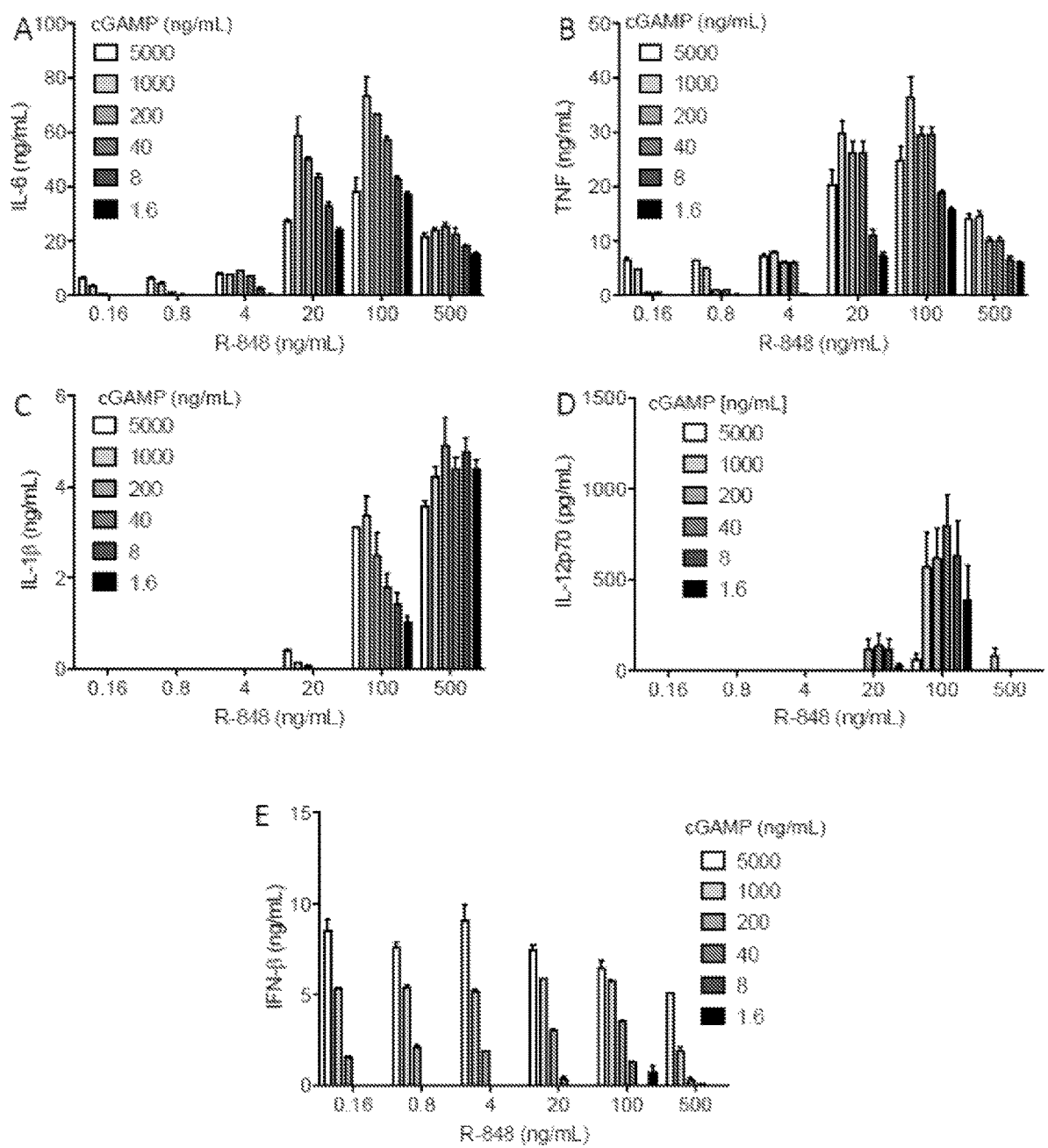
FIG. 16. Resiquimod and cGAMP MPs synergize to induce a diverse cytokine profile: Bone marrow derived dendritic cells from C57BL/6 mice were treated with indicated concentrations of R848 and cGAMP, both of which were encapsulated within Ace-DEX microparticles. Six hours later supernatants were harvested and analyzed for IL-6 (A), TNF (B), IL-1β (C), IL-12p70 (D) and IFN-β (E). (n=4±SEM).

To determine the optimal ratio of cGAMP to R848 for immune cell activation, a dose titration of both cGAMP MPs, and soluble R848 was performed in BMDCs (FIG. 16). For all pro-inflammatory cytokines tested, the optimal ratio of cGAMP MPs to R848 was determined to be 10:1 (FIGS. 16A-D). However the ratio of cGAMP MPs to R848 did not impact the type-I interferon response (FIG. 16E).

Figure 17:
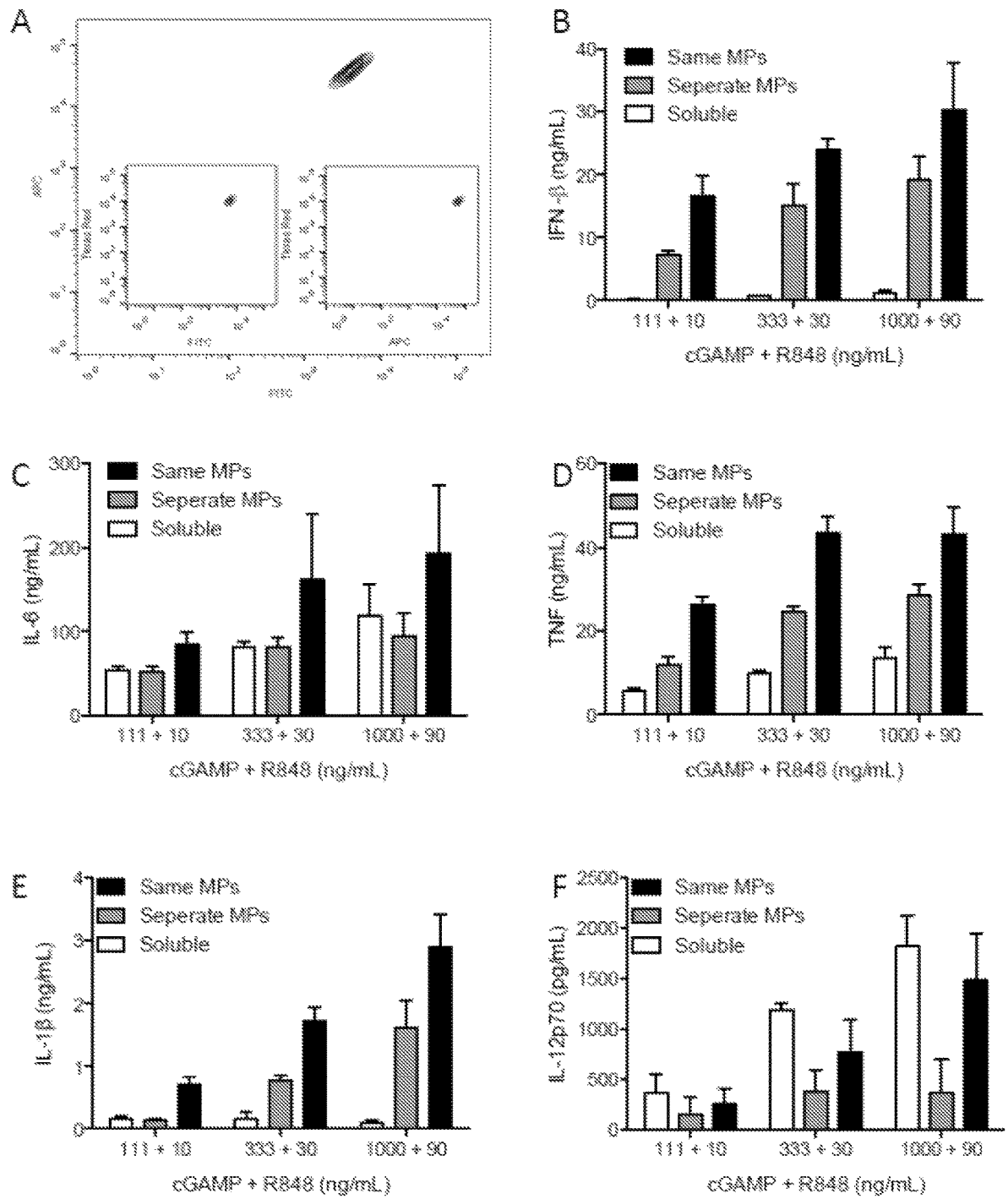
FIG. 17. Co-encapsulation or cGAMP and R848 results in potent and diverse cytokine production: (A) Three hydrophobic dyes were loaded into Ace-DEX MPs in equal ratios. Encapsulation of each dye within individual particles was confirmed by FACS. (B-F) Bone marrow derived dendritic cells from C57BL/6 mice were treated with indicated concentrations of R848 and cGAMP which were delivered as soluble drug, encapsulated in separate Ace-DEX MPs, or co-encapsulated within the same Ace-DEX MP. Six hours later supernatants were harvested and analyzed for IL-6, TNF, IL-1β, IL-12p70 and IFN-β. (n=4±SEM).

Co-Encapsulation of cGAMP and R848 in Ace-DEX MPs Results in Potent Induction of Pro-Inflammatory Cytokines and Type-I Interferon:

Having determined the optimal ratio of cGAMP to R848 for immune cell activation, we examined the potential of co-encapsulation of the two compounds. Proof of principle for the co-encapsulation of multiple compounds was shown through co-encapsulation of three hydrophobic dyes in Ace-DEX MPs. Co-encapsulation was confirmed by FACS which showed a uniform population of particles positive for all three dyes (FIG. 17A). We then co-encapsulated cGAMP and R848 within Ace-DEX MPs at a 10:1 ratio by weight. We compared the ability of these particles to stimulate immune cells to soluble cGAMP and R848, or cGAMP and R848 encapsulated within separate microparticles (FIGS. 17B-F). Encapsulation of the PAMPs, either in separate particles or in the same particle, enhanced type-I interferon and cytokine responses. Co-encapsulated trended towards superior responses when compared to encapsulation within separate particles.

Figure 18:
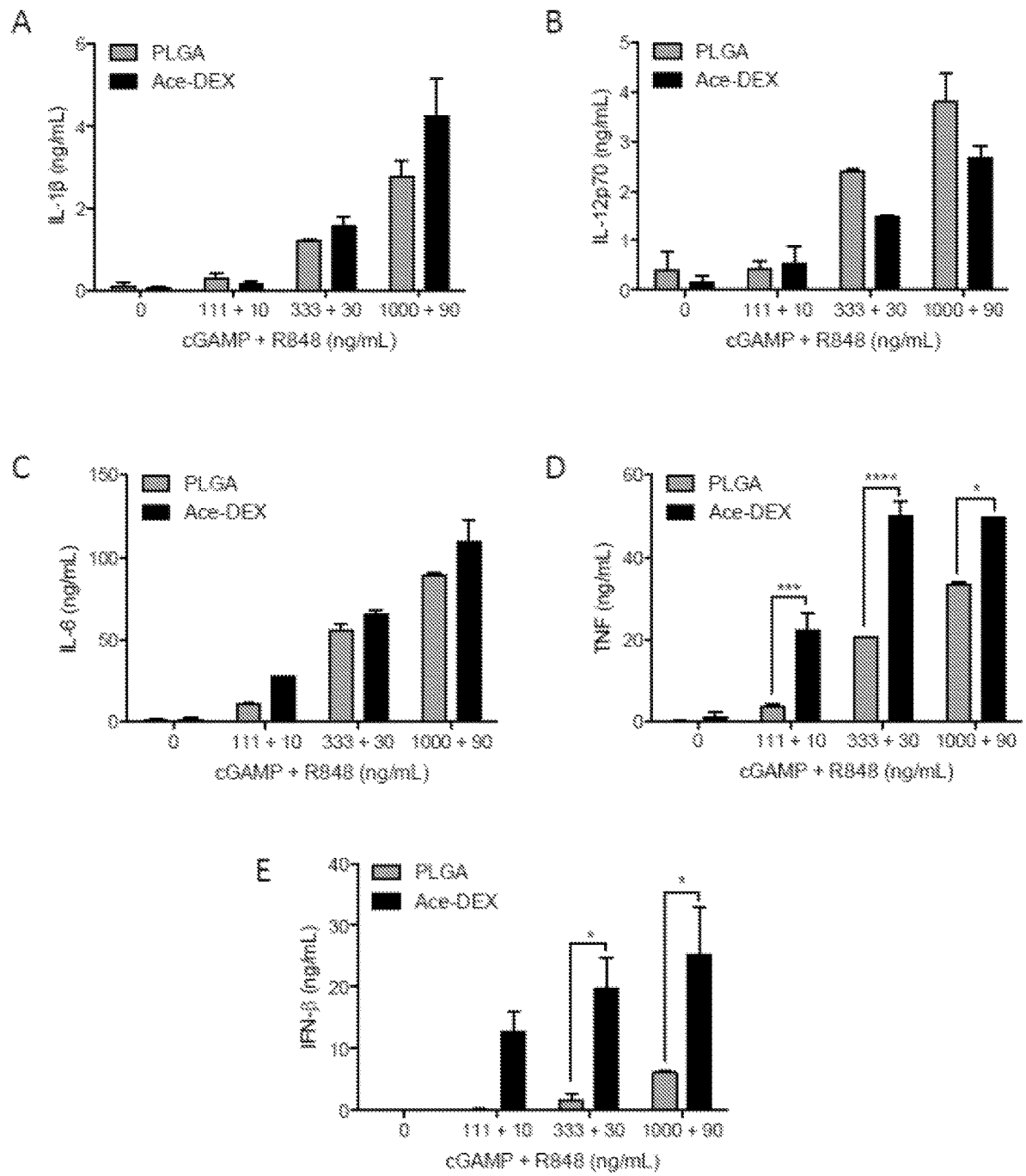
FIG. 18. Co-encapsulation of cGAMP and R848 in Ace-DEX microparticles is superior to PLGA: Bone marrow derived dendritic cells from C57BL/6 mice were treated with indicated concentrations of R848 and cGAMP co-encapsulated within Ace-DEX or PLGA microparticles. Six hours later supernatants were harvested and analyzed for IL-6 (C), TNF (D), IL-1β (A), IL-12p70 (B) and IFN-β (E). (n=2±SEM).

We next compared co-encapsulation of cGAMP and R848 within different polymeric microparticles. PAMPs were co-encapsulated within electrosprayed microparticles composed of either the acid sensitive polymer Ace-DEX, or the slow degrading polymer PLGA at identical 10:1 ratios of cGAMP to R848. The ability of these particles to stimulate immune cells was directly compared in BMDCs (FIG. 18). While both polymeric MPs induced similar levels of IL-6, IL-12p70 and IL-1β (FIGS. 18A-C), the acid sensitive Ace-DEX MPs induced significantly higher levels of TNF and type-I interferon (FIG. 18D-E). These particles are henceforth referred to as Ace-DEX R848/cGAMP MPs and PLGA R848/cGAMP MPs.

Figure 19:
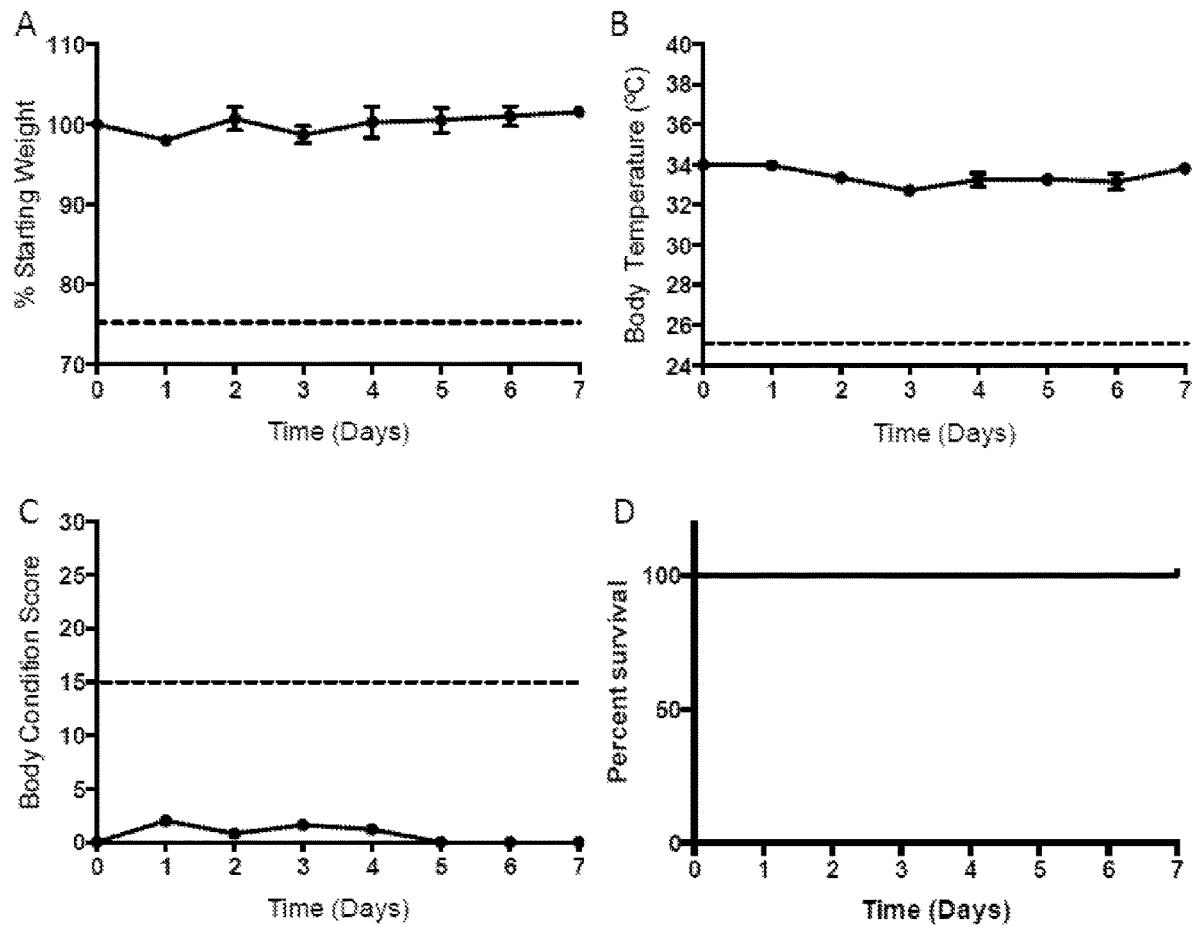
FIG. 19. cGAMP/R848 Ace-DEX microparticles do not induce toxicity: C57BL/6 females were immunized i.m. with cGAMP/R848 Ace-DEX microparticles containing 200 ng of cGAMP and 18.1 ng of R848. Body weight (A), body temperature (B), body condition (C) and survival (D) were monitored for 7 days. (n=5+SD) FIG. 20. Comparison of antibody responses induced by Ace-DEX and PLGA delivered cGAMP and R848 adjuvants: C57BL/6 females were immunized i.m. with PBS or OVA (10 ug) alone or in combination with the indicated combinations of cGAMP (200 ng) and R848 (18.1 ng) delivered as soluble, separate single loaded or dual loaded Ace-DEX microparticles, or blank and dual loaded PLGA microparticles. Animals received a boost with the same formulation 21 days later. One week following the last boost serum was collected and analyzed for ova specific total IgG (A), IgG1 (B) and IgG2c (C). The isotype balance between IgG2c and IgG1 was also assessed (D). (n=4-5±SEM,*p<0.05, p<0.01, *p<0.001, ****p<0.0001)

Ace-DEX R848/cGAMP MPs are Safe, and Induce a Robust Immune Response In Vivo:

To assess toxicity of Ace-DEX R848/cGAMP MPs in vivo, mice were injected i.m. with particles containing 200 ng of cGAMP and 18.2 ng of R848, then monitored for 7 days. No mortality occurred, and no significant changes in body weight, temperature or overall body condition were observed (FIG. 19).

Figure 20:
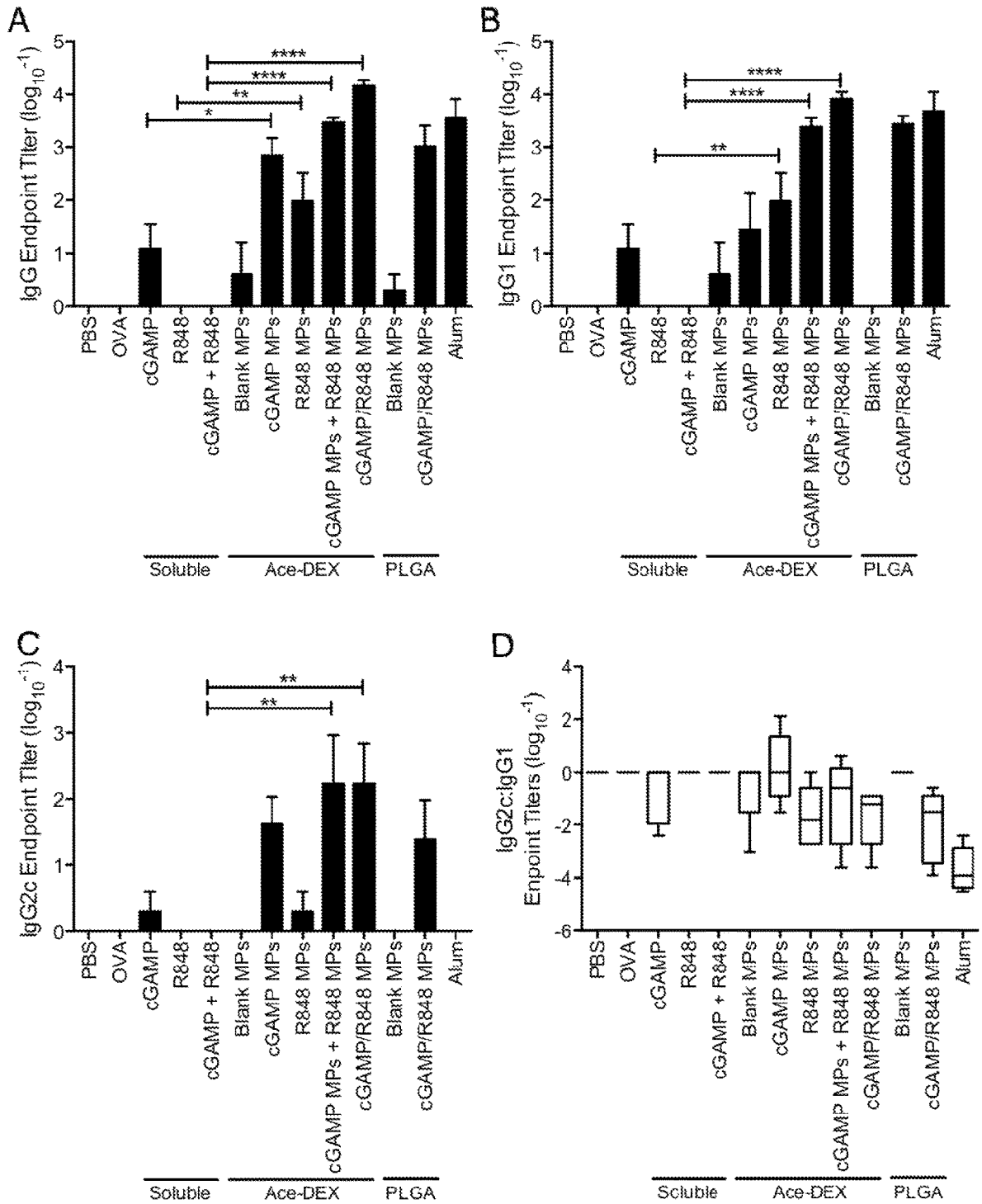
Figure 21:
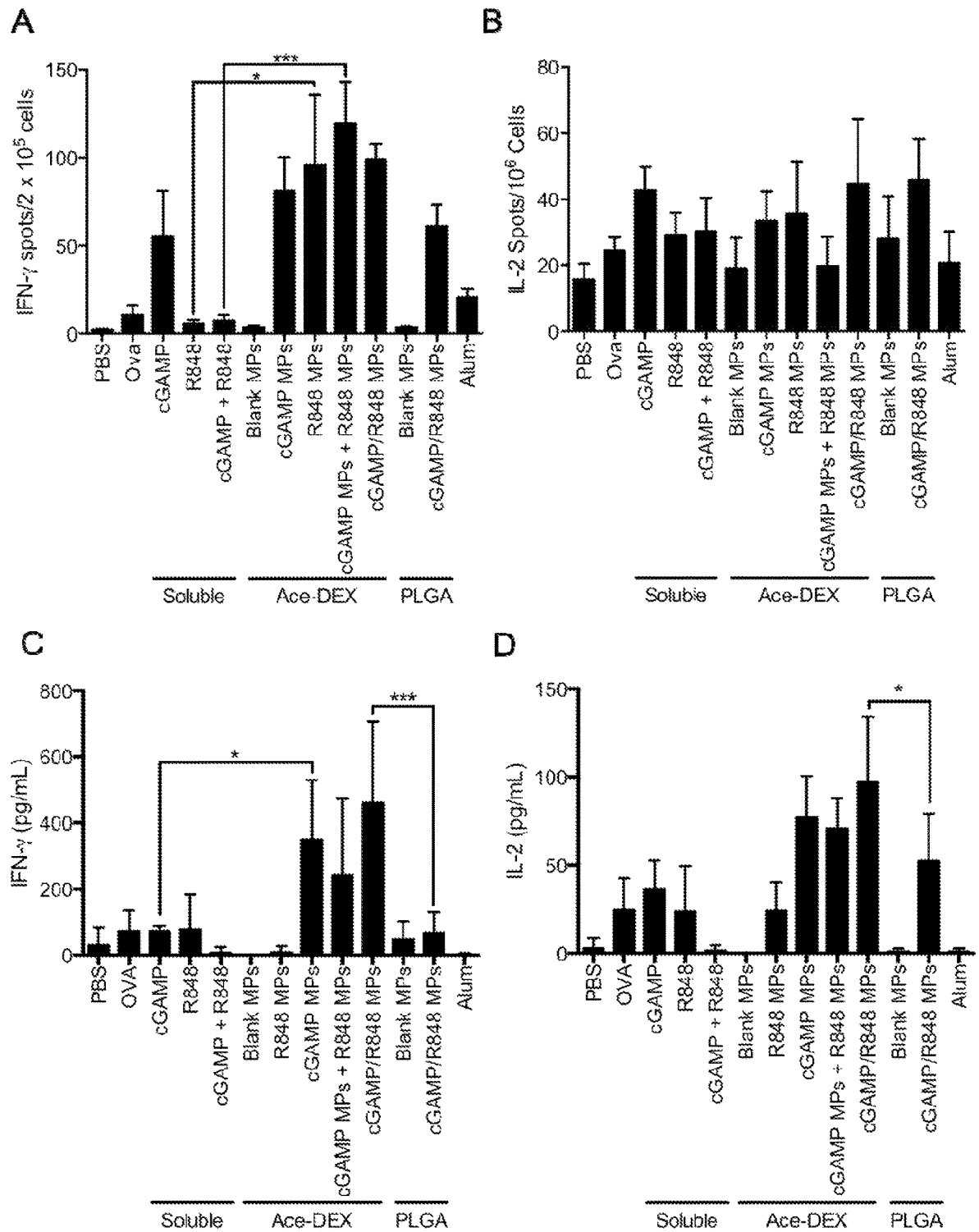
FIG. 21. Comparison of T cell responses induced by Ace-DEX and PLGA delivered cGAMP and R848 adjuvants: C57BL/6 females were immunized i.m. with PBS or OVA (10 ug) alone or in combination with the indicated combinations of cGAMP (200 ng) and R848 (18.1 ng) delivered as soluble, separate single loaded or dual loaded Ace-DEX microparticles, or blank and dual loaded PLGA microparticles. Animals received a boost with the same formulation 21 and 35 days later. One week following the last boost, mice were sacrificed and IFN-γ (A) and IL-2 (B) ELISPOTs were performed on splenocytes restimulated with SIINFEKL peptide (10 ug/mL) for 48 hours. Alternatively $10^6$ splenocytes were stimulated with 10 ug/mL OVA protein for 48 hours. Supernatants were analyzed for IFN-γ (C) and IL-2 (D) by ELISA. (n=4-5±SEM,*p<0.05, ***p<0.001)

We next assessed the adjuvant activity of various combinations of soluble, Ace-DEX encapsulated, or PLGA encapsulated cGAMP and R848 in combination with the model antigen OVA. Mice were immunized with the indicated formulations, then received a boost with the same formulation 21 days later. Titers were assessed 28 days post immunization (FIG. 20). Ace-DEX R848/cGAMP MPs generated the highest overall titers, trending higher than Ace-DEX cGAMP MPs, as well as PLGA R848/cGAMP MPs in total IgG, as well as IgG1 and IgG2c. However these results did not reach significance. All cGAMP containing formulations generated a relatively balanced IgG2c:IgG1 ratio, indicating a balanced Th1:Th2 response (FIG. 20D). Similar results were observed in OVA specific T cell responses (FIG. 21). However a significantly higher number of OVA specific T cells was observed in the Ace-DEX R848/cGAMP MP group compared to the PLGA R848/cGAMP MP group.

Example 3: A Novel Micro Particle Based Platform for the Delivery of Interferon Stimulating PAMPs This project explores the use of PAMPs encapsulated within a proprietary microparticle platform as an adjuvant for a subunit influenza vaccine. Classes of PAMPs examined have been shown to be potent inducers of the type I interferon response, making them an exciting adjuvant candidate for viral vaccines. However, intracellular localization of cognate receptors represents a formidable physiological barrier hampering clinical usefulness and adjuvant design. To overcome this barrier we have employed a novel microparticle (MP) technology allowing targeted release of the PAMP within the cell.

Dose Sparing.

Preliminary in vitro analysis indicated that delivery of the PAMP of interest encapsulated within MPs conferred greater than 200 fold dose sparing when compared to delivery of soluble PAMP, or conventional transfection approaches. In order to examine dose sparing using MPs, and inform doses for further characterization of the immune response, the optimal dose of PAMP loaded MPs will be determined experimentally. Mice will be immunized with 1 μg of PR8 HA alone or in combination with different doses of soluble or MP encapsulated PAMP on day 1 and day 21. Mice will be challenged with 4 $LD_{50}$ of A/Puerto Rico/8/1934 H1N1 influenza virus on day 42. Animal survival, weight loss, body temperature, and day 35 neutralizing titers will be used to characterize dose sparing, and inform doses used in further characterization of immune activation.

Assessment of Immune Activation.

Wild-type B6 mice (8-12 weeks of age) will be immunized intramuscularly with 1 μg of PR8 HA and blank MP control, or PAMP delivered as soluble or encapsulated within MPs. All treatments will be compared to HA protein administered with alum, a conventional vaccine adjuvant. Reimmunization on day 21 will be used to assess secondary and memory responses. A thorough assessment of B and T cell responses as described herein will inform us as to whether PAMP MPs represent a viable vaccine adjuvant.

To date we have generated MPs that encapsulate a PAMP. We have demonstrated that these particles are stable under a range of storage conditions and can be sterilized using gamma-irradiation without impacting biological activity. The encapsulation of PAMP led to a 1000-fold and 50-fold enhancement in type-I-IFN production in vitro and in vivo respectively compared to soluble PAMP. We have also observed a minimum of 50-fold dose sparing of PAMP through encapsulation.

Using a model antigen (OVA) and hemagglutinin (HA) from influenza A, we observed a 40-fold enhancement of antigen-specific antibodies and a 30-fold increase in antigen specific T cells, with PAMP MPs when compared to soluble PAMP. Furthermore we observed a skewing towards Th1 associated IgG isotypes, and vaccination with PAMP MPs completely protected against a lethal influenza challenge. A greater than 50-fold dose sparing of PAMP through encapsulation within MPs was also observed for antibody titer, and antigen specific T development.

Figure 22A:
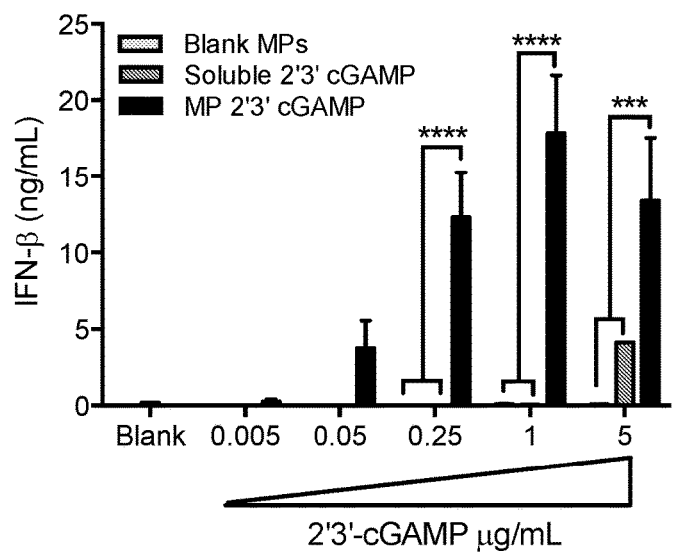
FIG. 22. Encapsulation of 2'3'-cGAMP enhances type-I interferon and cytokine responses. Bone marrow derived dendritic cells from C57BL/6 mice were left untreated (NT) or treated with indicated concentrations of 2'3'- or 3'3-cGAMP delivered as soluble or encapsulated in ES Ace-DEX microparticles, as well as equivalent doses of blank MPs. Cell supernatants were collected 6 hours later and were analyzed for IFN-β (A), TNF (B) and IL-6 (C) by ELISA. (n=4±SEM, p<0.01, *p<0.001, ****p<0.0001)
Figure 22B:
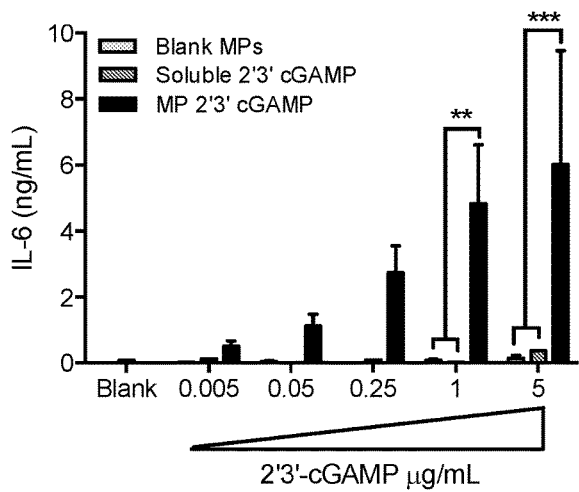
Figure 22C:
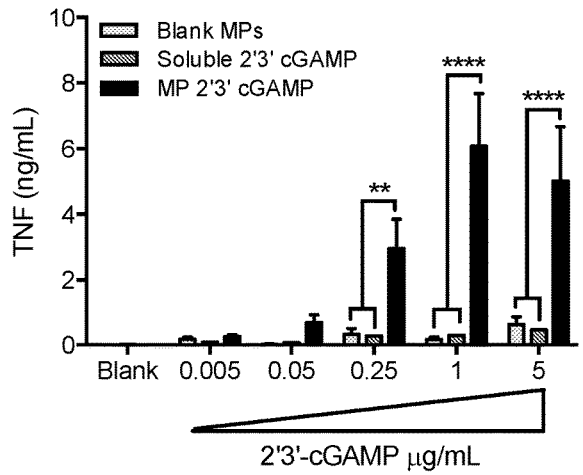

Example 4: Encapsulation of 2'3'-cGAMP Enhances Type-I Interferon and Cytokine Responses Bone marrow derived dendritic cells (BMDCs) from C57BL/6 mice were treated with the indicated doses of soluble or Ace-DEX MP encapsulated 2'3'cGAMP, and an equivalent dose of blank MPs. Cell supernatants were collected 6 hours later and were analyzed for IFN-β (FIG. 22A), TNF (FIG. 22B) and IL-6 (FIG. 22C) by ELISA. (n=4±SEM, p<0.01, *p<0.001, ****p<0.0001).

Example 5: cGAMP MPs Ameliorate Clinical Symptoms in a Model of Experimental Autoimmune Encephalomyelitis (EAE)

Figure 23:
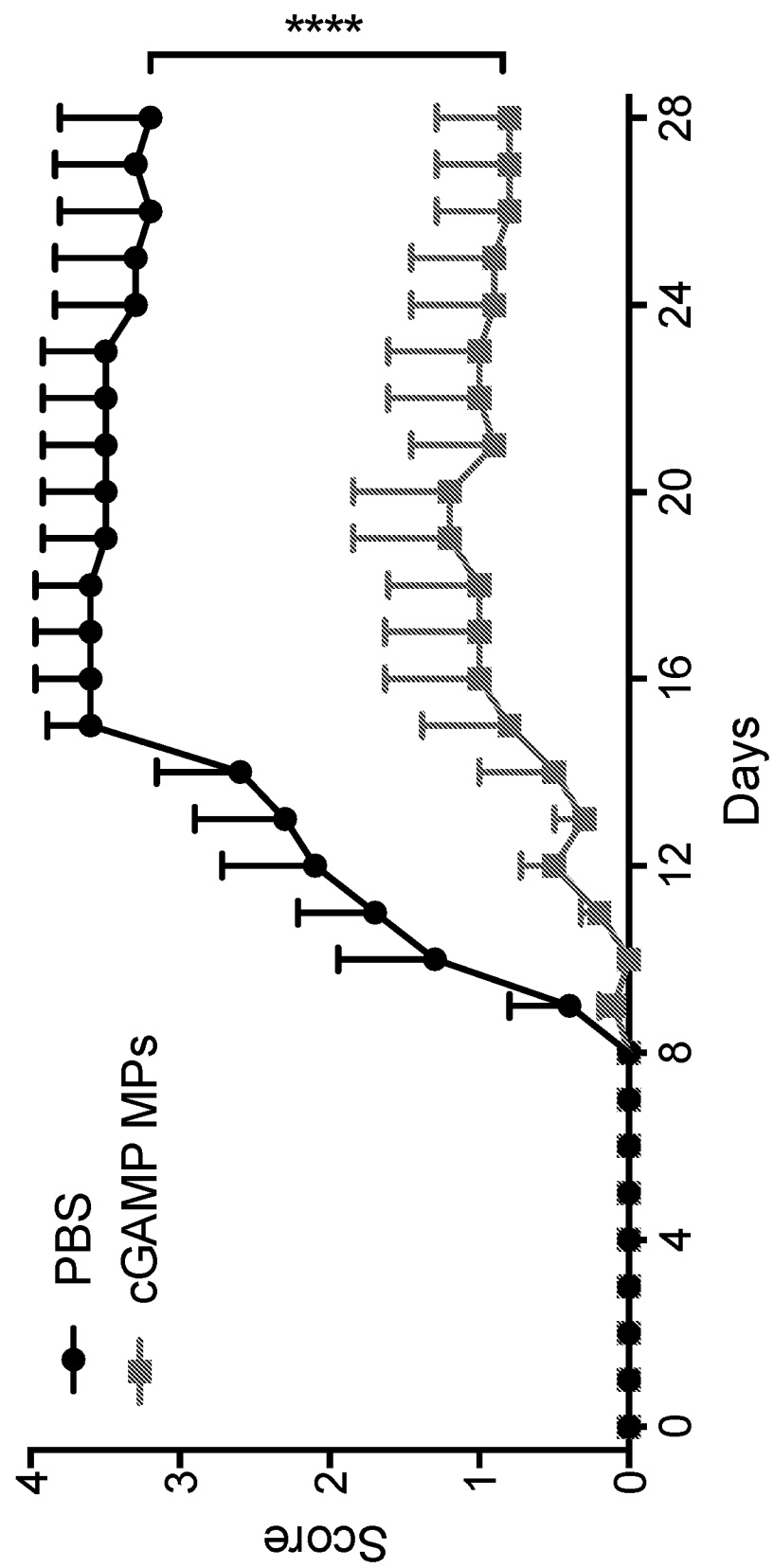
FIG. 23. cGAMP MPs ameliorate clinical symptoms in a model of experimental autoimmune encephalomyelitis (EAE). Starting 9 days post induction of EAE (at first onset of disease), mice received injections of PBS or 5 μg of cGAMP encapsulated within Ace-DEX MPs every 2 days for a total 5 injections. Clinical score (A) and weight change (B) were monitored for 28 days. The following scale was used to assess clinical scores: 0, normal mouse, no overt sign of disease; 0.5, partial tail paralysis (loss of tip tail tonus); 1, limp tail or hind limb weakness but not both; 2, limp tail and hind limb weakness; 3, partial hind limb paralysis; 4, complete hind limb paralysis; and 5, moribund state, sacrifice for humane reasons. (n=5±SD).
Figure 24:
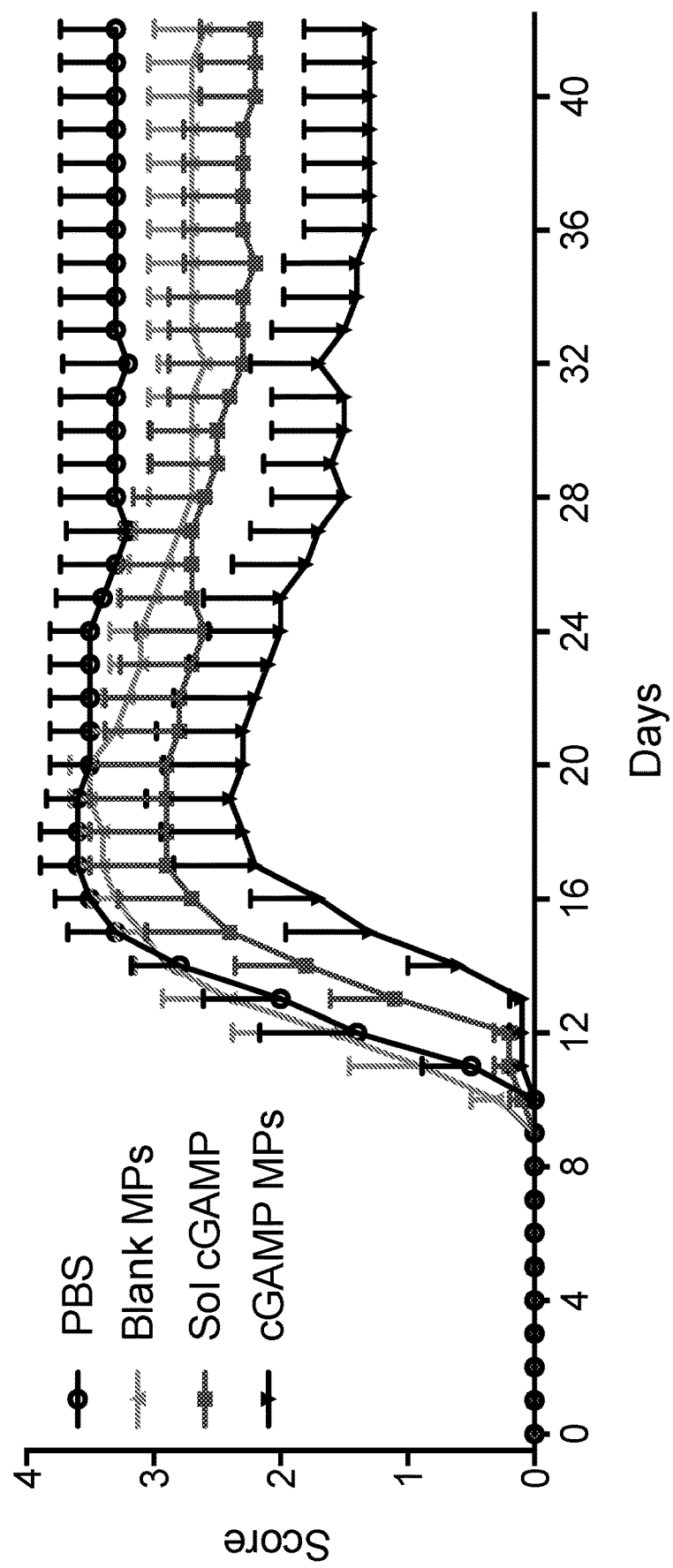
FIG. 24. cGAMP MPs are superior to soluble cGAMP for amelioration of clinical symptoms of EAE. Starting 9 days post induction of EAE (at first onset of disease), mice received injections of PBS, blank Ace-DEX MPs or 5 μg of cGAMP delivered as soluble, or encapsulated within Ace-DEX MPs every 2 days for a total 5 injections. Disease severity was monitored for 42 days. The following scale was used to assess clinical scores: 0, normal mouse, no overt sign of disease; 0.5, partial tail paralysis (loss of tip tail tonus); 1, limp tail or hind limb weakness but not both; 2, limp tail and hind limb weakness; 3, partial hind limb paralysis; 4, complete hind limb paralysis; and 5, moribund state, sacrifice for humane reasons. (n=5±SD).

MOG(35-55) peptide emulsified in complete Freund adjuvant (4 mg/mL) was subcutaneously injected to sites adjacent to mouse tails. On days 0 and 2 post injection, 400 ng of pertussis toxin was injected intraperitoneally (i.p.). After the onset of symptoms (Day 9) mice were left untreated, or received 5 μg of cGAMP MPs (MP dose 500 μg) i.m. every 2 days, for a total of 5 injections. Clinical score (FIG. 23) was monitored for 28 days. Ace-DEX cGAMP MPs significantly reduced EAE symptoms compared to untreated animals. We next compared Ace-DEX cGAMP MPs to blank microparticles and soluble cGAMP using the EAE model and dosing schedule described above (FIG. 24). While both particles and soluble cGAMP reduced EAE scores, Ace-DEX cGAMP MPs resulted in the greatest amelioration of EAE symptoms.

Example 6: cGAMP MPs as Immunotherapy for Triple Negative Breast Cancer

Figure 26:
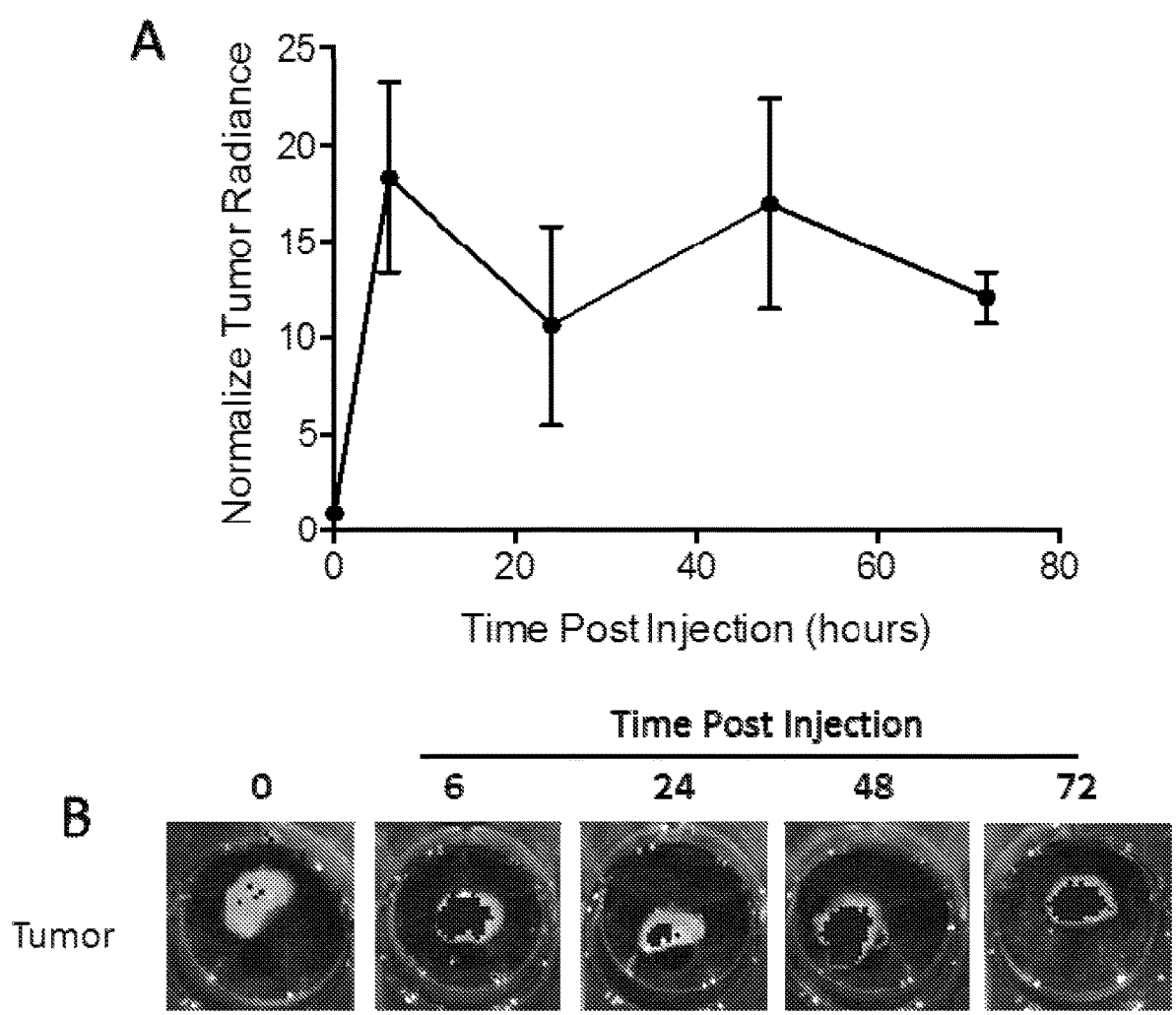
FIG. 26. Ace-DEX MPs traffic to tumors in murine model of triple negative breast cancer. C3(1)/Tag breast cancer cells were inoculated into the mammary fat pad of FVB/NJ mice. When tumors reached 4-6 mm$^3$ in size, mice were injected i.m. with PBS (time 0) or Texas-Red Ace-DEX particles (4:1 unlabeled dextran: Texas-Red dextran). Fluorescence in the tumor and liver was imaged at the indicated time points using the IVIS-Lumina imaging system. (A) Radiance was quantified in the tumor and normalized to liver fluorescence. (B) Representative images of tumors are shown. (n=5±SD)

Type-I interferon has been used extensively in the clinic as an immunotherapy for various cancers. However, recombinant interferon therapy is extremely expensive. Hence there is a significant need for novel and cost-effective immunotherapies that can induce endogenous interferon. To this end we investigated a novel microparticle technology for the delivery of STING-agonist 3'3'-cGAMP for the treatment of triple negative breast cancer. In order to assess trafficking of Ace-DEX MPs in a tumor model, C3(1)/Tag triple negative breast cancer cells were inoculated into the mammary fat pad of FVB/NJ mice. When the tumors reached 4-6 mm³ in size, mice were inject i.v. with Texas-Red Ace-DEX MPs. Tumors and livers were collected at various time points after injection of the particles and fluorescence was assessed using an IVIS-Lumina imaging system. Fluorescent particles were found to rapidly accumulate in the tumor by 6 hours post-injection and remain detectable up to 72 hours later (FIG. 26). These data demonstrate that electrosprayed Ace-DEX MPs traffic to tumors in a murine model of breast cancer.

Figure 27:
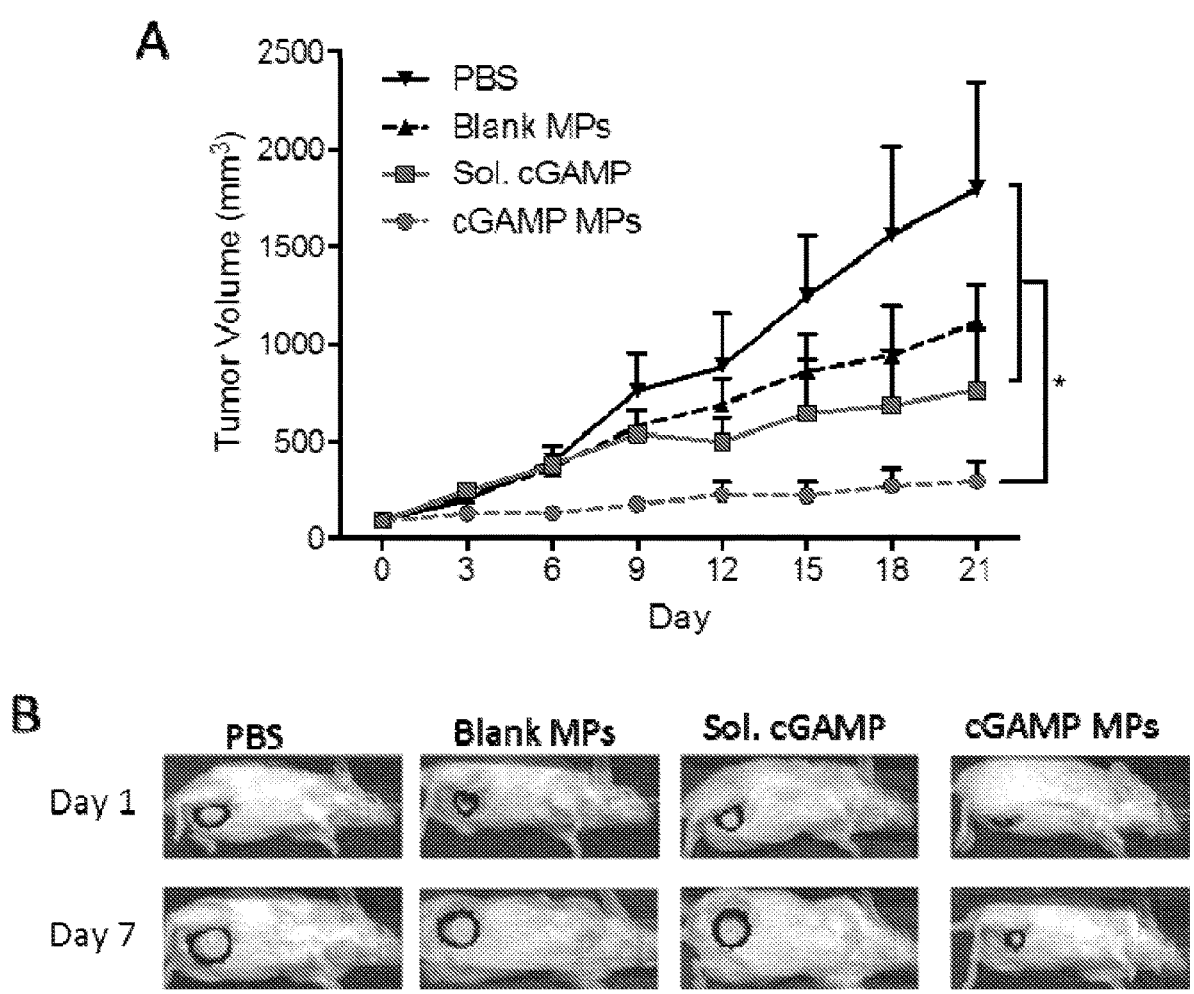
FIG. 27. Ace-DEX cGAMP MPs significantly delay tumor growth in a murine model of triple negative breast cancer. C3(1)/Tag breast cancer cells expressing luciferase were inoculated into the mammary fat pad of FVB/NJ mice. When tumors reached 4-6 mm$^3$ in size, mice were injected i.v. with PBS, blank Ace-DEX MPs (1 mg), soluble cGAMP (10 μg) or cGAMP MPs (10 μg in 1 mg MP) every 3 days for a total of 7 injections. (A) Tumor volume was measured every 3 days. (B) Tumor growth was tracked by luminescence on day 1 and day 7. (n=5-6±SEM).

To assess the potential of Ace-DEX cGAMP MPs as an immunotherapy for triple negative breast cancer, luciferase expressing C3(1)/Tag tumor cells were injected into the mammary fat pad of FVB/NJ mice. Once tumors reached 4-6 mm³ in size, mice were treated with i.v. injections of PBS, blank cGAMP MPs or 10 μg of soluble or Ace-DEX encapsulated cGAMP every 3 days, for a total of 7 injections. Tumor volume was monitored every 3 days, and luciferase activity was assessed on days 1 and 7 to monitor tumor growth (FIG. 27). Animals treated with cGAMP MPs showed significantly delayed tumor growth compared to all other groups.

Example 7: cGAMP MPs Polarize M2 Macrophages Towards M1 Phenotypes

Figure 28:
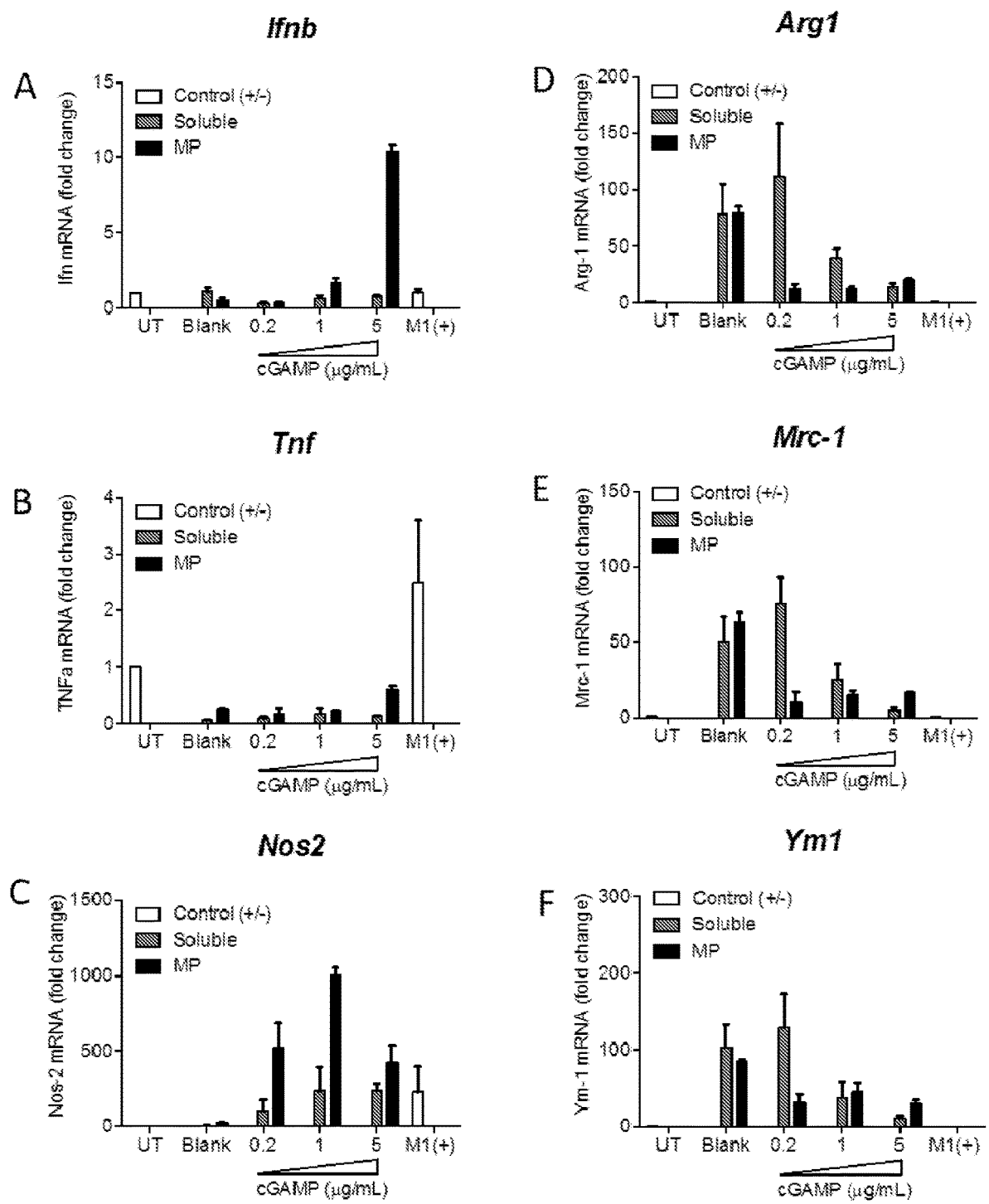
FIG. 28. Ace-DEX cGAMP MPs polarize M2 macrophages towards an M1 phenotype. Bone marrow derived macrophages were left untreated (UT), or polarized to M1 (M1+) or M2 macrophages. Cells were treated with the indicated dose of soluble, or Ace-DEX encapsulated cGAMP. Twenty-four hours later RNA was extracted and real time PCR was performed for the M1 markers (A) Ifnb, (B) Tnf and (C) Nos2 and the M2 markers (D) Arg1, (E) Mrc-1 and (F) Ym1. (n=4±SEM).

Tumor associated macrophages (TAMs) significantly contribute to tumor microenvironment where they promote tumor progression. TAMs display a plastic M2 phenotype and represent an exciting target for cancer immunotherapy. Hence there is a significant need for compounds capable of converting M2 macrophages into M1 cells. To examine whether ES Ace-DEX MPs are capable of converting M2 polarized macrophages into M1 cells, bone marrow derived macrophages (BMMs) were left unstimulated or polarized into M2 cells using IL-4. Alternatively, cells were treated with LPS and IFN-γ to generate an M1 control. M2 polarized cells were then treated with various doses of soluble or Ace-DEX encapsulated cGAMP for 24 hours after which RNA was extracted. PCR analysis was used to assess the M1 markers Ifnb, I16, and Nos2, as well as the M2 markers Arg1, Mrc1 and Ym1 (FIG. 28). ES Ace-DEX cGAMP MPs significantly reduced M2 markers, and increased M1 markers compared to soluble cGAMP and M2 controls. Encapsulation of cGAMP within Ace-DEX MPs also resulted in M1 polarization at significantly lower doses compared to the soluble CDN.

Figure 29:
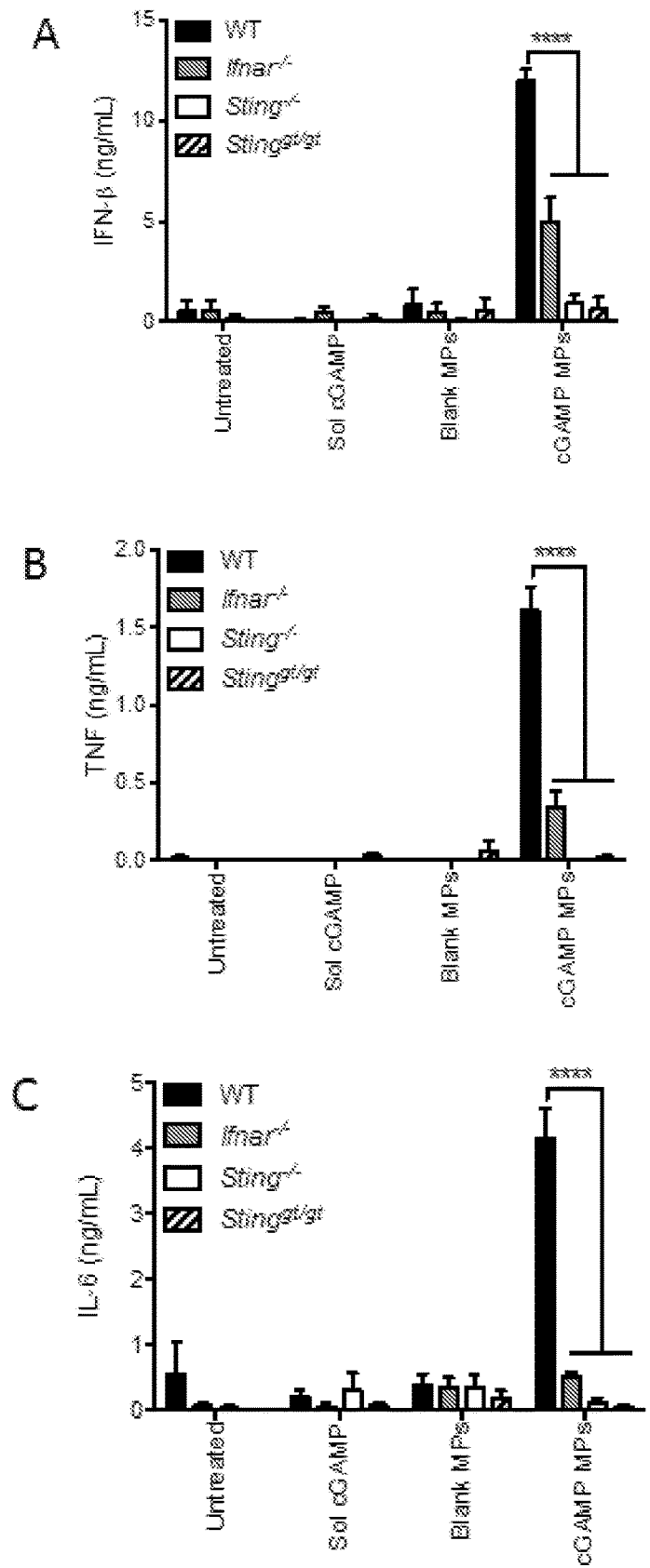
FIG. 29. cGAMP MP induce cytokines through the STING/IFNAR axis: Bone marrow derived macrophages were cultured from wild-type (WT), IFNAR-deficient (Ifnar$^{-/-}$), STING-deficient (Sting$^{-/-}$) or mice harboring a loss of function mutation in STING (Sting$^{gt/gt}$). Each genotype was treated was left untreated, or treated with 1 μg/mL cGAMP delivered as soluble (Sol cGAMP), or encapsulated within Ace-DEX MPs (cGAMP MPs), or an equivalent MP dose of unloaded Ace-DEX MPs (Blank MPs). Six hours later, supernatants were collected and analyzed for IFN-β (A), TNF (B) and IL-6 (C). (n=4±SEM,****p<0.0001).

Example 8: Ace-DEX cGAMP Microparticles Induce STING Dependent Immunity In Vitro and In Vivo To confirm that electrosprayed Ace-DEX cGAMP microparticles (MPs) induce immune responses through the predicted stimulator of interferon genes (STING)-dependent signaling pathways, bone marrow-derived dendritic cells (BMDCs) were prepared in vitro from wild-type mice, as well as mice deficient in Ifnar, the type-I interferon (IFN) receptor responsible for amplifying STING-dependent IFN production, Sting-deficient animals ($Sting^{-/-}$), or mice harboring a mutation which renders STING inactive ($Sting^{gt/gt}$). Both type-I IFN and cytokine responses were decreased in BMDCs deficient in Ifnar, and were completely ablated in cells derive from both Sting and $Sting^{-/-}$ and $Sting^{gt/gt}$ animals (FIG. 29). These results demonstrate that production of type-I IFN and pro-inflammatory cytokines induced by cGAMP MPs is mediated through a well-defined, STING-dependent and IFNAR-enhanced, mechanism of action.

Figure 30:
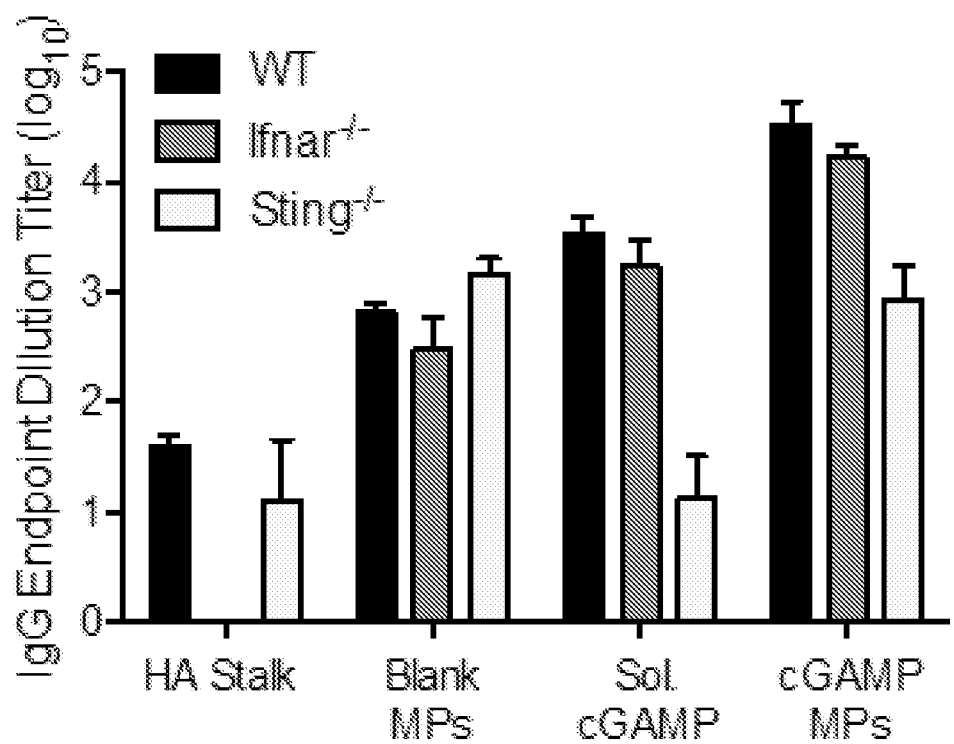
FIG. 30. cGAMP MP-induced humoral responses have both STING-dependent and independent components: 8 week old female C57BL/6 mice were immunized with soluble hemagglutinin stalk (HA Stalk, 10 μg) alone or combined with soluble cGAMP (Sol cGAMP, 10 μg) or Ace-DEX cGAMP microparticles (cGAMP MPs, 10 μg cGAMP in ~1 mg MP). A boost was administered 21 days later. Serum was collected on day 28 post-immunization and total HA (strain A/Puerto Rico/8/1934/H1N1) specific IgG (A) and IgG2c (B) specific endpoint titers were assessed (n=4).
Figure 30:
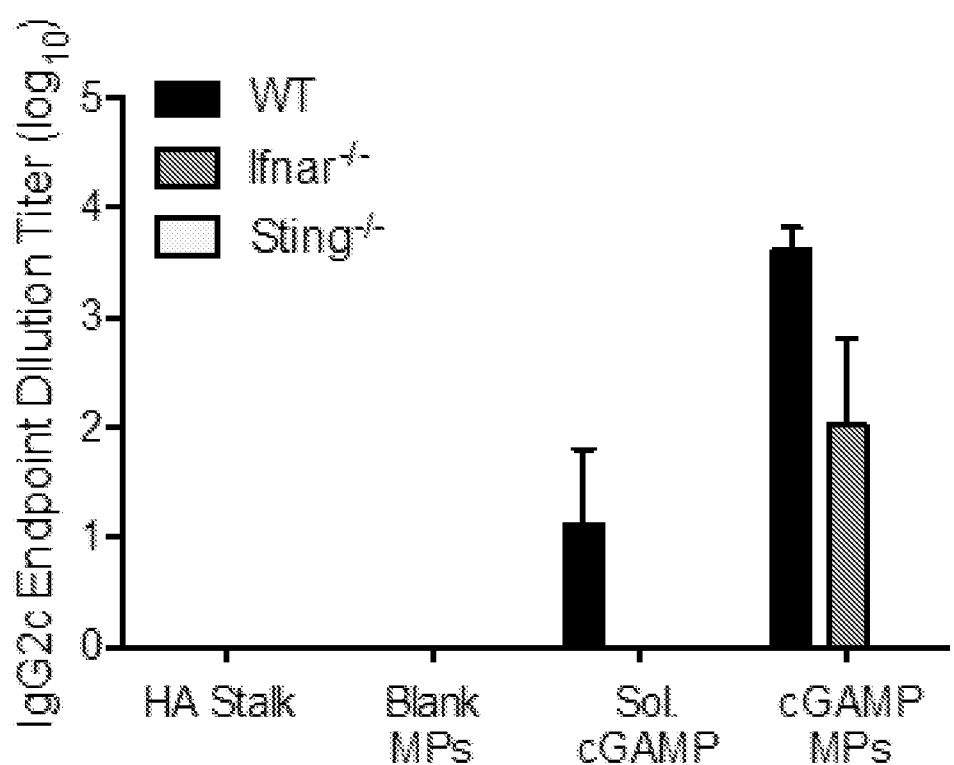

To confirm these observations in vivo, female C57BL/6 mice were immunized with stabilized hemagglutinin (HA)-stalk protein representing a universal influenza antigen[4] alone or adjuvanted with Blank Ace-DEX MPs, soluble cGAMP or Ace-DEX cGAMP MPs. Following a boost 21 days later, blood was collected and HA (A/Puerto Rico/08/34, H1N1) specific IgG and IgG2c titers were assessed (FIG. 30). For total IgG production soluble cGAMP adjuvant activity was entirely Sting-dependent, while the adjuvant effects of Blank MPs were unaffected by Sting-deficiency. In contrast, the adjuvant activity of Ace-DEX cGAMP MPs was partially reduced in Sting-deficient mice, to the level of Blank MPs, indicating that there are both Sting-dependent (cGAMP) and Sting-independent (MP) components to the overall adjuvant activity of the particles. Ifnar-deficiency did not impact total IgG responses, indicated that in contrast to in vitro findings, Ifnar was dispensable for the adjuvant activity of the Ace-DEX cGAMP MPs in vivo. IgG2c is an antibody isotype associated with Th1-polarized immunity. In contrast to total IgG levels, the production of IgG2c was completely dependent upon STING, indicating that the polymeric particles contribute to total IgG production in a Sting-independent manner, while encapsulated cGAMP drives Th1 polarization through a Sting-dependent mechanism.

Figure 31:
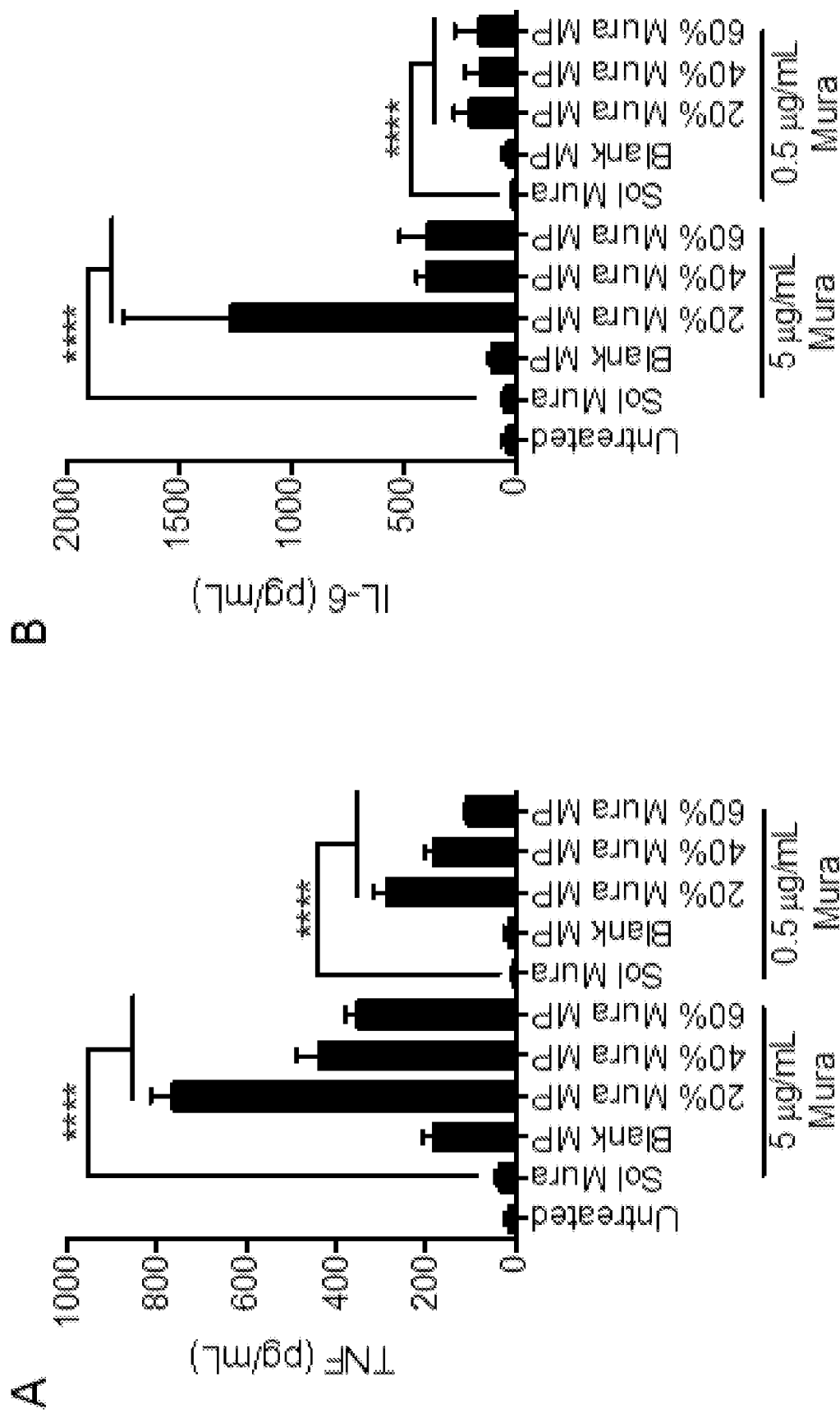
FIG. 31. Low cyclic coverage on murabutide loaded Ace-DEX MPs induces optimal responses in vitro: Bone marrow derived dendritic cells were cultured from C57BL/6 mice, then left untreated, or stimulated with the indicated dose of soluble murabitude, unloaded Ace-DEX MPs (Blank), or murabutide loaded Ace-DEX MPs (Mura MP) with relative cyclic acetal coverages of 20, 40 or 60%. Twenty four hours later, supernatants were collected and analyzed for TNF (A) and IL-6 (B) (n=4±SEM, ****p<0.0001).

Example 9: Tuning Ace-DEX Microparticle Degradation Rates Allows for Optimization of Murabutide's Immune Adjuvant Activity Murabutide is an agonist of the intracellular pathogen recognition receptor known as nucleotide-binding oligomerization domain-containing protein 2 (NOD2), an exciting targeted for both vaccine adjuvants[5] and cancer immunotherapies. However, the intracellular localization of NOD2 requires targeted delivery of its agonists into the cytosol for optimal biological activity. In order to optimize murabutide delivery it was encapsulated within electrosprayed Ace-DEX microparticles (MPs) with polymer relative cyclic acetal coverages (CACs) ranging from 20 to 60%. The degradation rates of these particles at acidic pH vary with the 20% CAC degrading most quickly, and the 60% CAC degrading most slowly. To assess how degradation rate impacts biological activity of murabutide, bone marrow-derived dendritic cells (BMDCs) were left untreated, treated with blank Ace-DEX MPs, or with different concentration of murabutide Ace-DEX MPs with the indicated cyclic coverages. Eighteen hours later supernatants were harvest and the cytokines TNF and IL-6 was assessed by ELISA (FIG. 31). Critically, all murabutide Ace-DEX MPs demonstrated significantly greater biological activity than soluble murabutide. However, the optimal biological responses in vitro were observed with the lower CAC, indicating that rapidly degrading particles are ideal for murabutide delivery.

Figure 32:
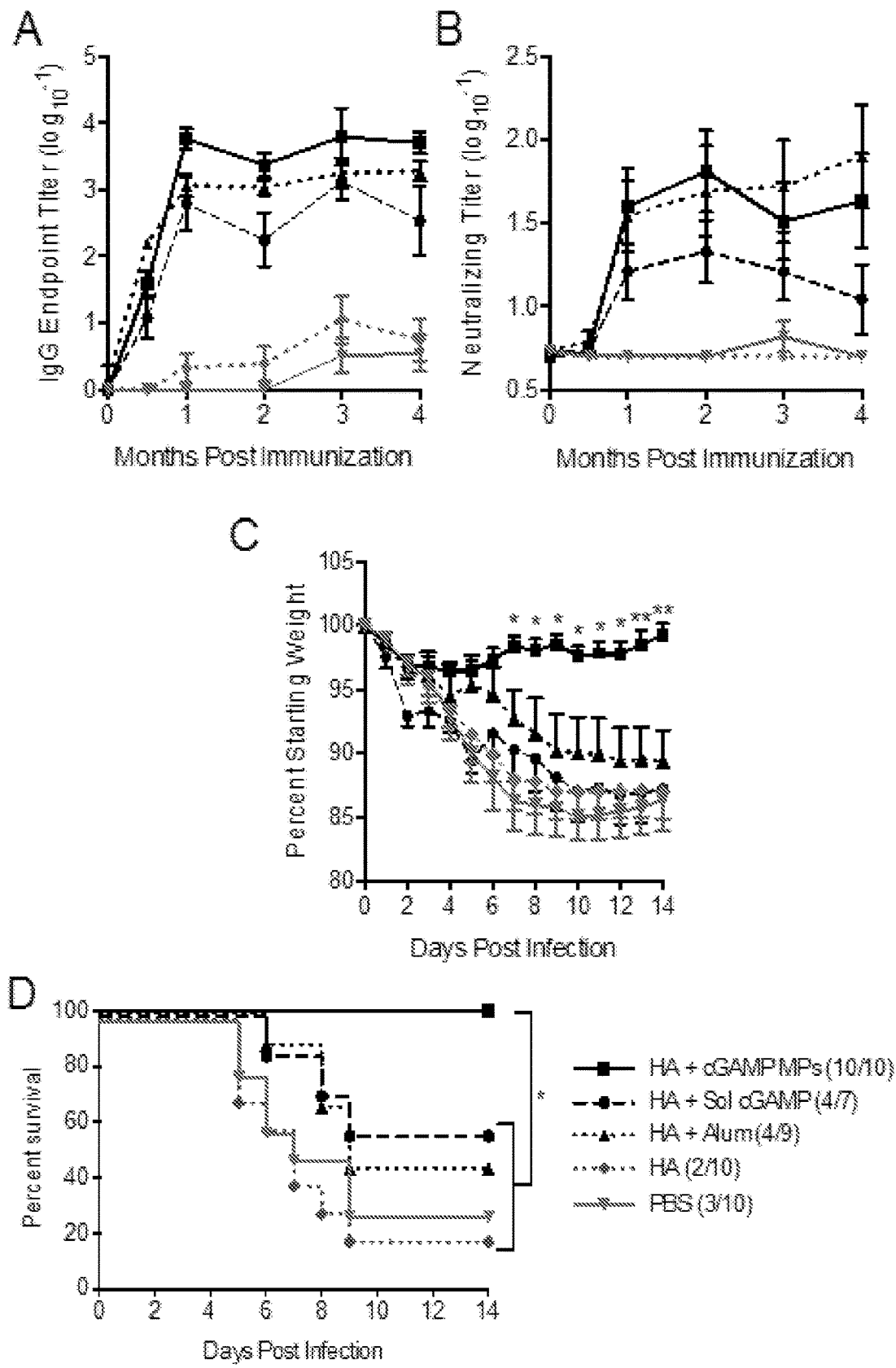
FIG. 32. Ace-DEX cGAMP MPs provide long term protection against lethal influenza challenge: 8 week old female C57BL/6 mice were immunized with PBS, or soluble hemagglutinin (HA, 1 μg) from strain A/Puerto Rico/8/1934/H1N1 either alone or combined with soluble cGAMP (HA+Sol cGAMP, 0.2 μg), cGAMP microparticles (HA+cGAMP MPs, 0.2 μg cGAMP in 1 mg MP) or Alhydrogel 2% (HA+Alum 1:1 by volume). A boost was administered 21 days later. (A) Total HA specific IgG endpoint titers (B) and virus neutralizing titers were assessed over 4 months. Seven months post-immunization mice were infected intranasally with 2,000 ffu of A/Puerto Rico/8/1934/H1N1. (C) Survival, (D) weight loss, and (E) disease score were assessed daily for 14 days. The last recorded weight and disease score for deceased animals were used to calculate group averages at subsequent time points (n=7-10±SD. *p<0.05, **p<0.01).

Example 10: Ace-DEX cGAMP Microparticles Provide Long Term Protection Against Influenza Infection A significant drawback of current influenza vaccines is that they induce relatively short-lived immunity. In order to assess the longevity of the protection provided by influenza hemagglutinin (HA) protein (from A/Puerto Rico/8/34 H1N1 virus) adjuvanted with electrosprayed Ace-DEX cGAMP microparticles (MPs), mice were left unimmunized or immunized with HA alone, or HA adjuvanted with soluble cGAMP, cGAMP MPs, or alum. Animals received a boost with the same formulation 21 days later. Serum was collected monthly, and then HA-specific IgG and neutralizing antibody titers were monitored (FIG. 32A-B). Alum, soluble cGAMP, and cGAMP MPs provided sustained levels of HA-specific IgG over time, with cGAMP MPs providing the highest overall titers. Similarly, serum collected from mice that were immunized with alum or cGAMP MP adjuvants resulted in sustained virus neutralizing activity, while the neutralizing capacity of serum from mice immunized with soluble cGAMP began to wane by 4 months post-immunization. In order to assess whether mice were protected over the timeframe of a clinical flu season, they were challenged with a lethal dose of A/Puerto Rico/8/34 H1N1 influenza virus seven months post-immunization. Mice immunized with cGAMP MPs maintained body weight post-infection, showing significantly less weight loss than all other groups tested (FIG. 32C). Similarly, of the groups tested, only cGAMP MPs provided complete protection (FIG. 32D). Some protection was conferred by soluble cGAMP and unadjuvanted HA, as seen in short term infection studies as well. Furthermore, the protection afforded by the cGAMP MP-adjuvanted formulation was significantly superior to the alum group. Together these results demonstrate that immunization with a subunit influenza protein vaccine adjuvanted with cGAMP MPs provided long-term protection against a lethal influenza infection, superior to a state-of-the-art alum adjuvant.

Example 11: Ace-DEX cGAMP Microparticles Induce Cross-Reactive Antibodies when Formulated with a Universal Influenza Antigen The heterogeneity of influenza surface proteins such as hemagglutinin (HA), combined with rapid antigenic drift, necessitates annual reformulation of influenza vaccines. This approach leads to a number of problems including short term protection against only the strains predicted to circulate that season, and the risk of the predicted strains not matching the strains that actually circulate during flu season. In order to overcome these issues, many groups have undertaken the search for 'universal' influenza antigens which represent highly conserved regions of influenza proteins that do not vary between strains, and do not drift over time. Many antigens have been studied, and one of the most promising candidates is the stalk region of HA.

Figure 33:
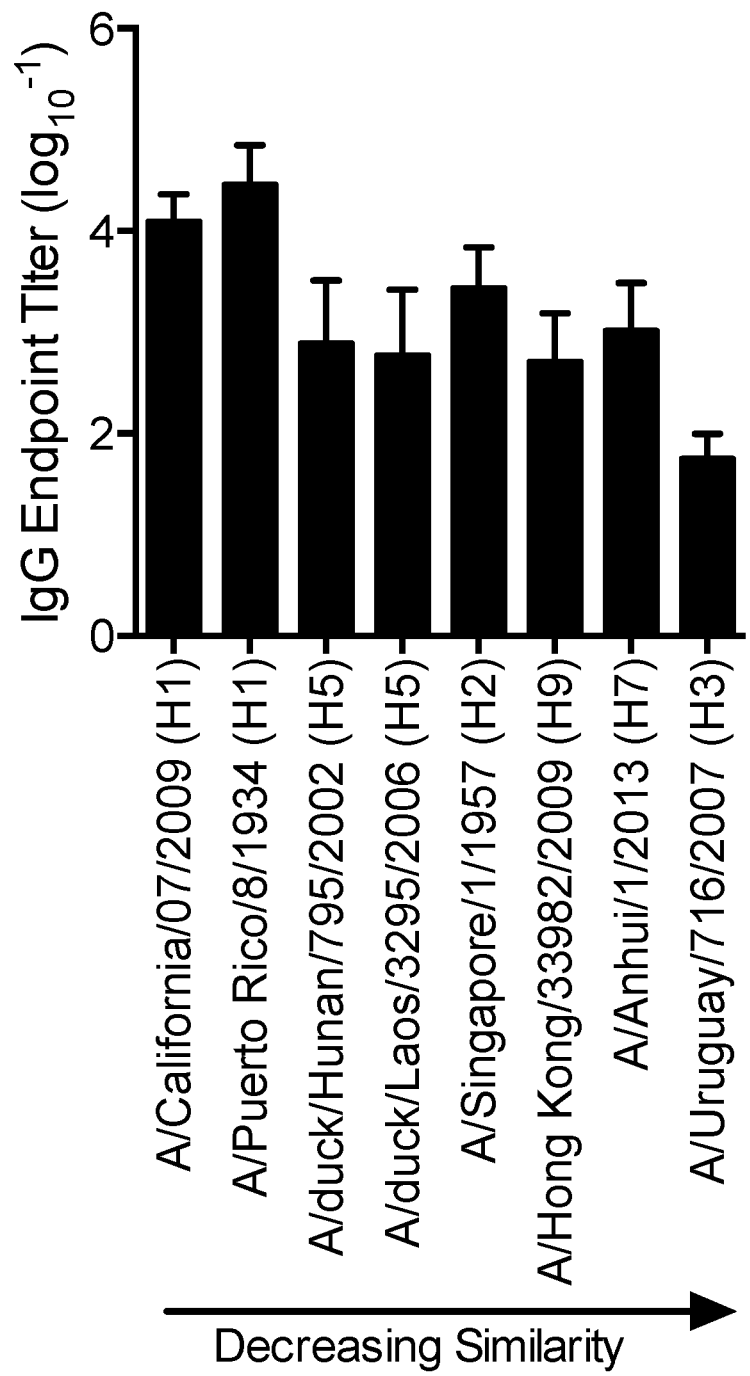
FIG. 33. Ace-DEX cGAMP MP adjuvanted universal influenza vaccine induces cross-reactive antibodies: Eight week old female C57BL/6 mice were immunized with 10 μg of a stabilized HA stalk protein from A/Brisbane/59/07 adjuvanted with 10 μg of cGAMP MPs. A boost was administered 21 days later, then serum was collected on day 28. Serum was analyzed for endpoint dilution titers against recombinant HA from the indicated strains of influenza (A). (n=10±SD).

Eight-week-old female mice were immunized with this HA Stalk influenza antigen, adjuvanted with electrosprayed Ace-DEX cGAMP microparticles (MPs). Following a boost on day 21, serum was collected on day 28 post immunization in order to examine the extent of cross-reactivity of the resulting antibodies against HA protein from a panel of influenza viruses, chosen to cover the major clinically relevant subtypes, and to reflect the antigenic diversity of the virus (FIG. 33). The HA stalk portion of the fusion protein was modified from strain A/Brisbane/59/07, an H1N1 virus. The greatest degree of reactivity was observed with other H1 strains. However, significant reactivity was observed against unrelated subtypes, and even across phylogenetic groups (H1 is a group 1 virus, while H3, H7 and H9 proteins are from group 2 viruses, reflecting extremely divergent antigens). These data confirm that Ace-DEX cGAMP MP adjuvanted HA Stalk protein induces highly cross-reactive antibodies which recognize antigenically diverse virus.

Figure 34A:
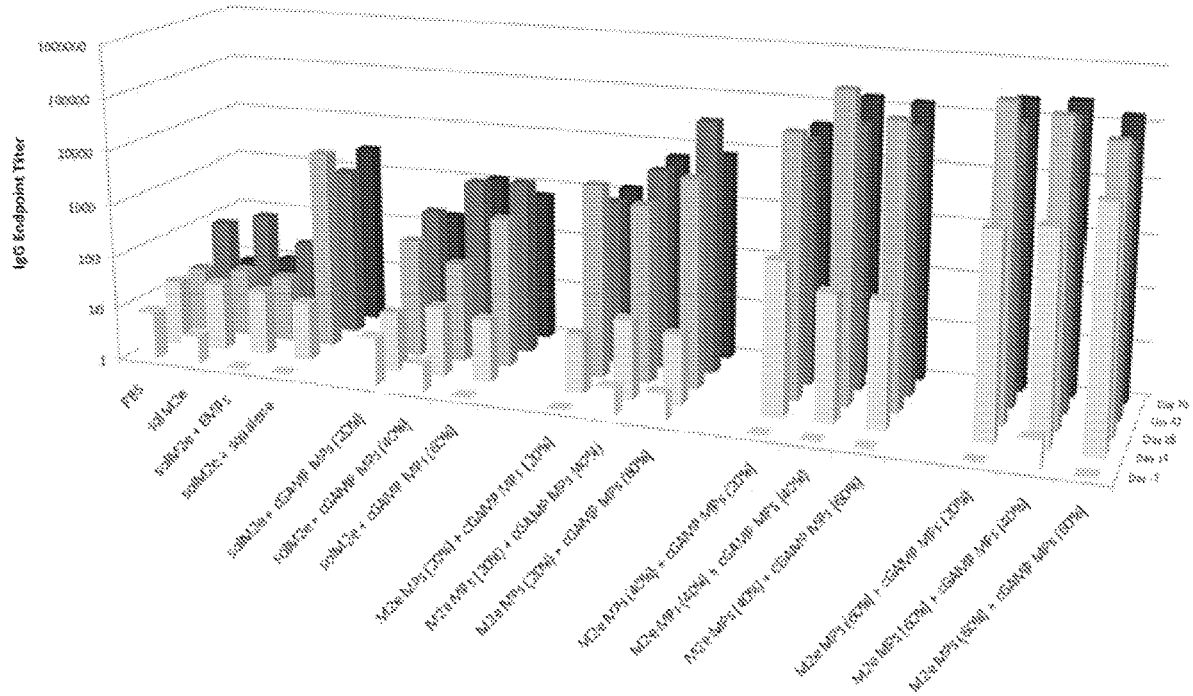
FIG. 34. Ace-DEX cGAMP MP improve efficacy of a universal influenza vaccine: Eight week old female BALB/c mice were immunized on day 0 and 21 with PBS or soluble M2e (10 μg) either unadjuvanted, or adjuvanted with blank Ace-DEX microparticles (EMPs), MF59-like squalene AddaVax emulsion (squalene), or cGAMP (1 μg) MPs composed of various Ace-DEX relative cyclic acetal coverages (CACs; 20, 40, or 60%). Alternatively, mice were immunized with M2e (10 μg) encapsulated within Ace-DEX MPs with various CACs (20, 40, or 60%) and adjuvanted with cGAMP (1 μg) MPs composed of various Ace-DEX CACs (20, 40, or 60%). Anti-M2e serum antibodies in the form of (A) total IgG, (B) IgG1, or (C) IgG2a were assessed on days −7, 14, 28, 42, and 70.
Figure 34B:
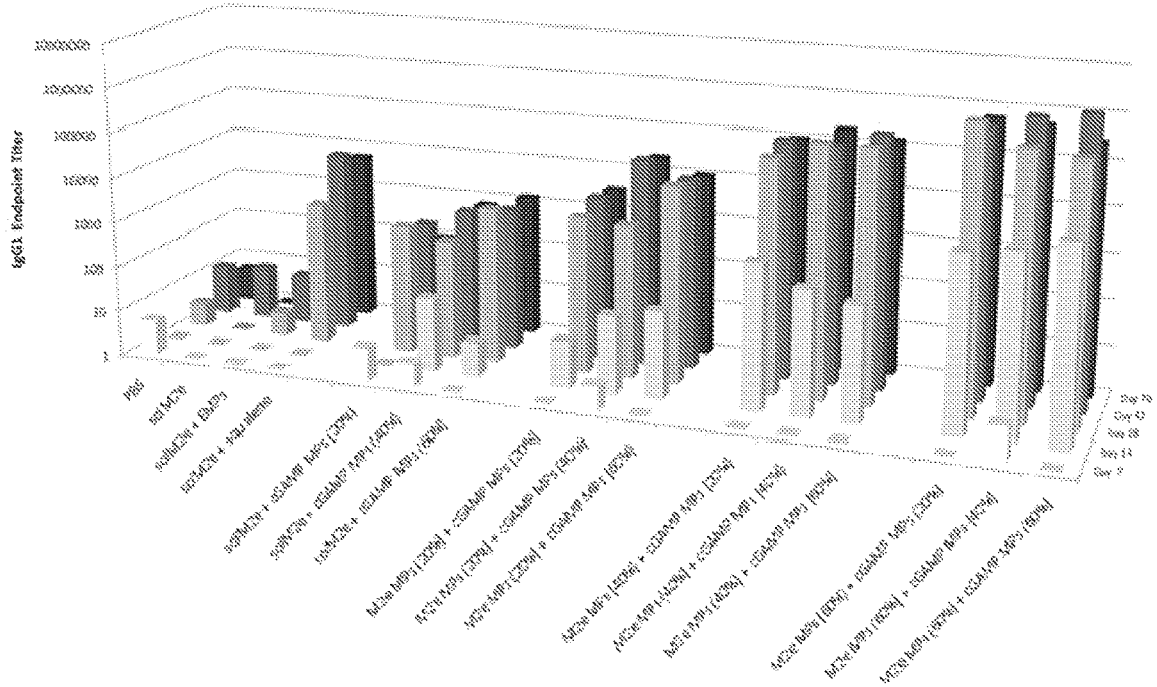
Figure 34C:
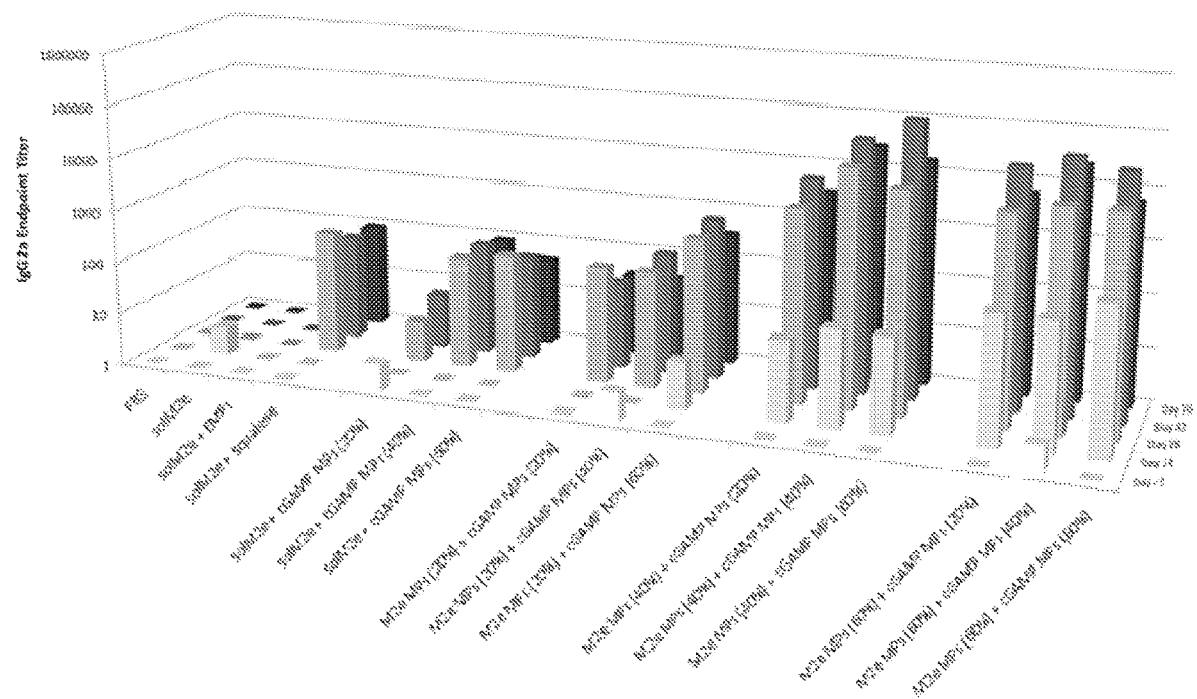
Figure 35A:
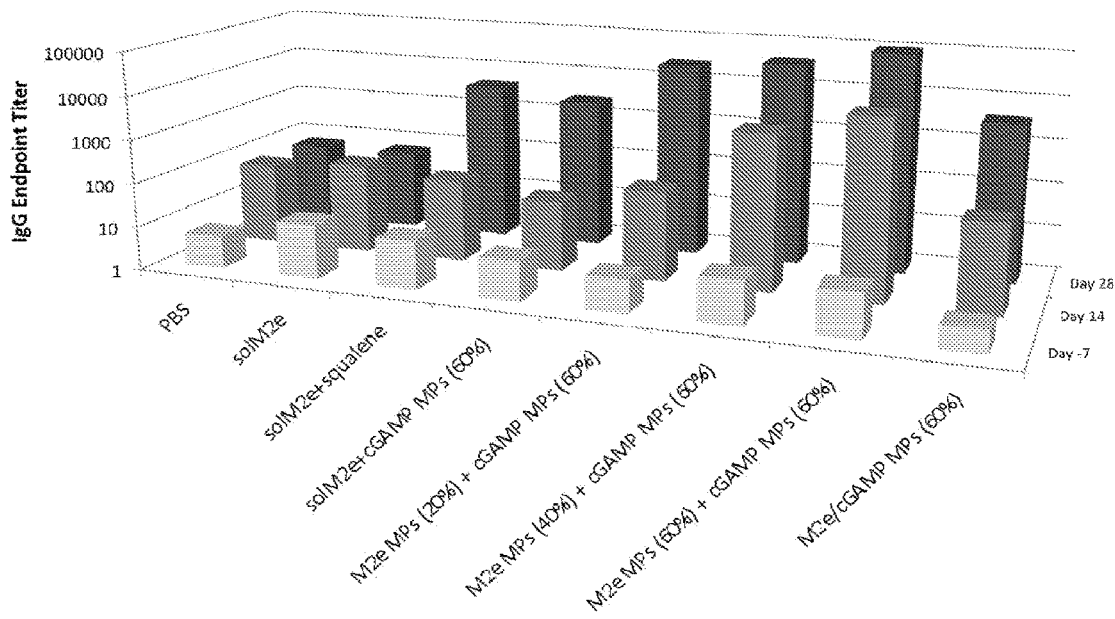
FIG. 35. Ace-DEX cGAMP MP improve efficacy of a universal influenza vaccine: Eight week old female BALB/c mice were immunized on day 0 and 21 with PBS or soluble M2e (10 μg) either unadjuvanted or adjuvanted with MF59-like squalene AddaVax emulsion (squalene). Alternatively, mice were immunized with M2e (10 μg) encapsulated within Ace-DEX MPs with various CACs (20, 40, or 60%) and adjuvanted with cGAMP (1 μg) MPs composed of 60% CAC Ace-DEX. Finally, one group of mice were immunized with M2e (10 μg) and cGAMP (1 μg) co-encapsulated in the same 60% CAC Ace-DEX MPs. Anti-M2e serum antibodies in the form of (A) total IgG, (B) IgG1, or (C) IgG2a were assessed on days −7, 14, and 28. On day 28, harvested splenocytes were unstimulated or restimulated with 10 ug/mL M2e. (D) Excreted cytokines were measured by ELISA, and (E) cytokine-forming cells were measured by ELISPOT.
Figure 35B:
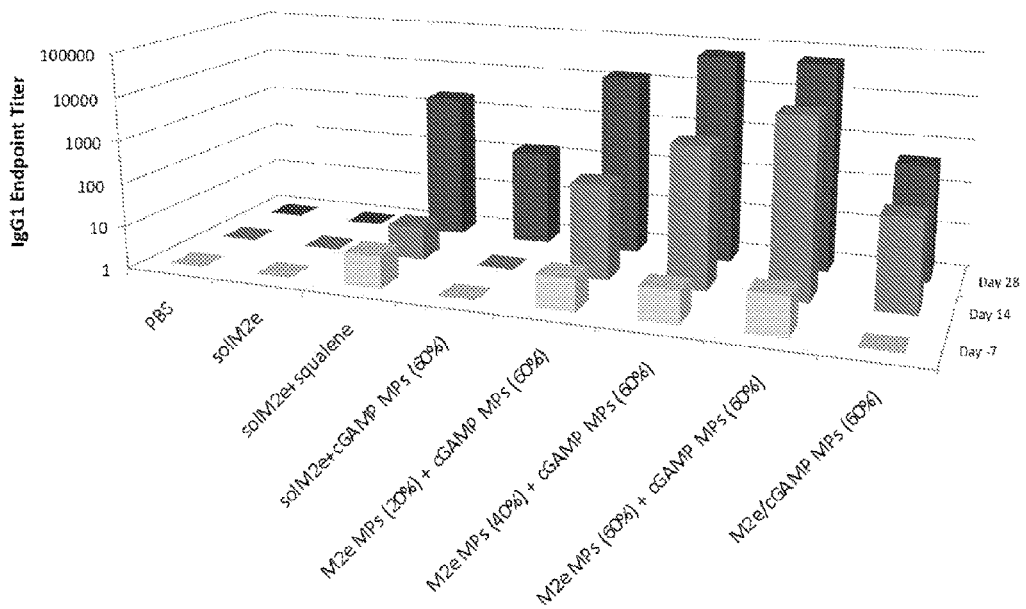
Figure 35C:
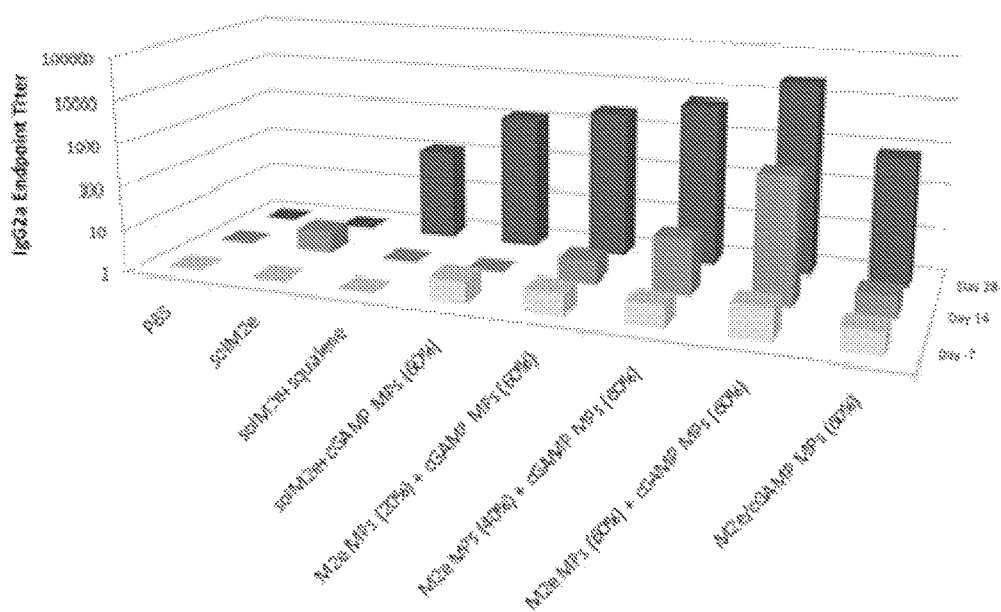
Figure 35D:
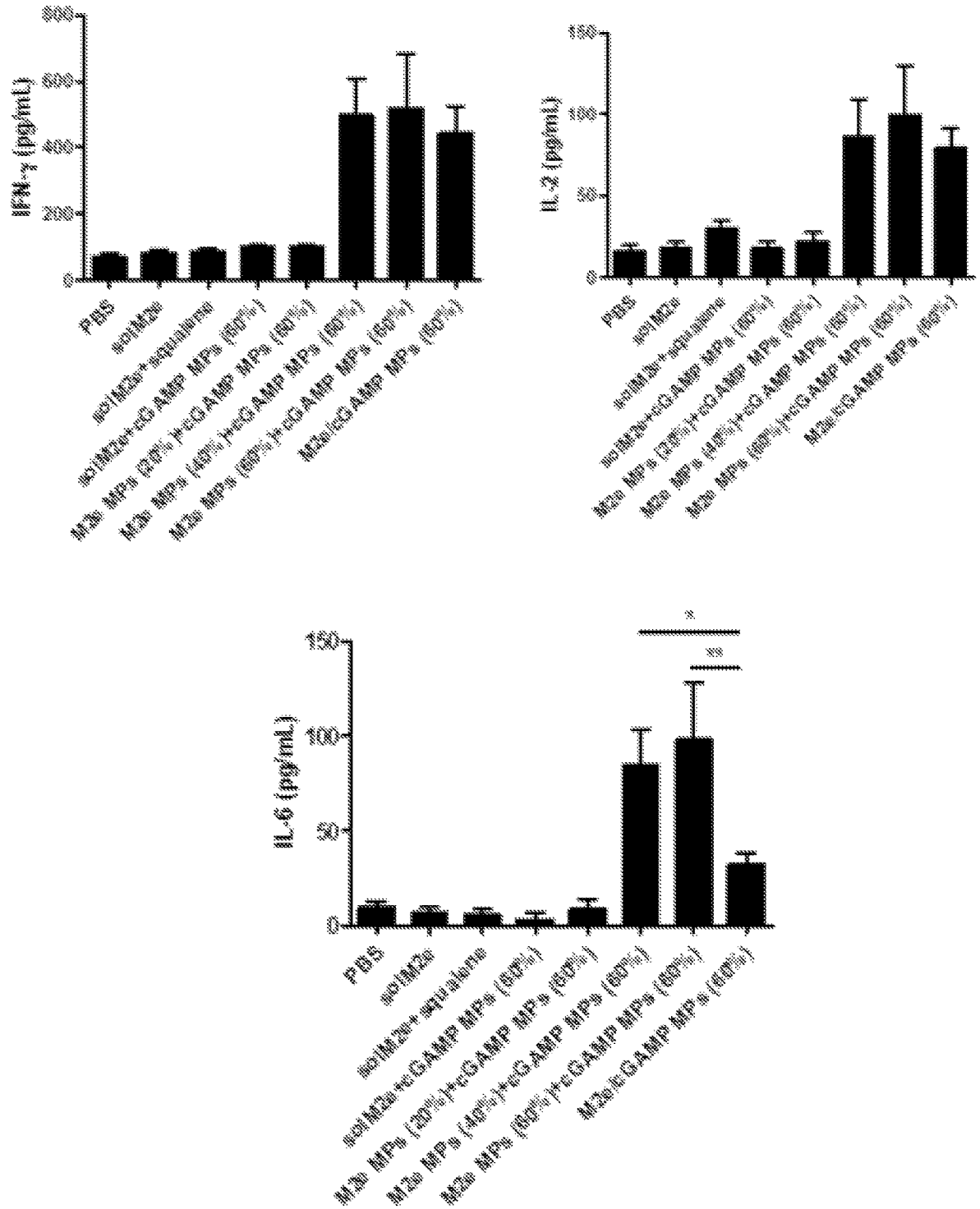
Figure 35E:
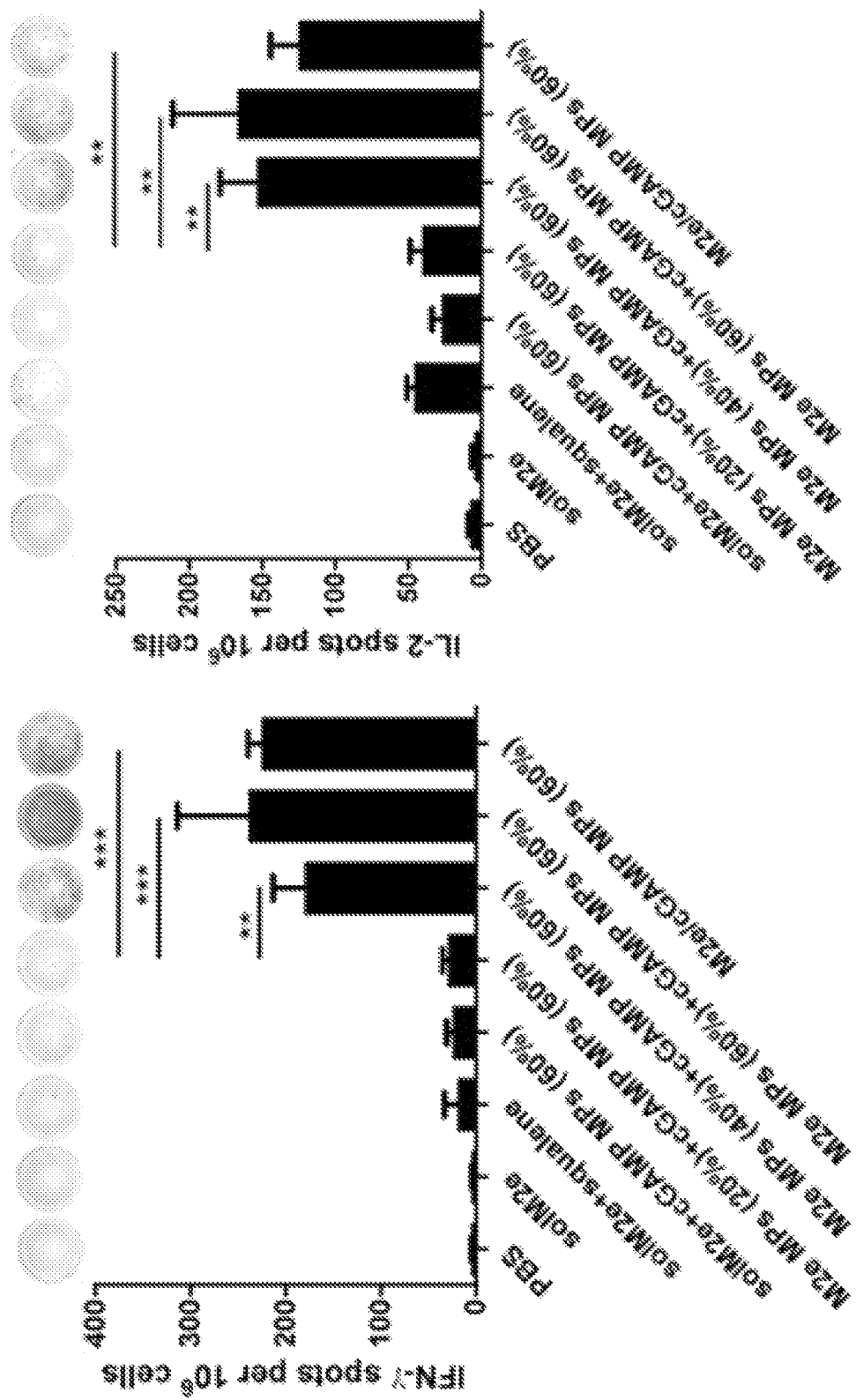

Example 12: Ace-DEX cGAMP Microparticles Combined with Ace-DEX M2e Microparticles Show Ability to Tune Humoral and Cellular Responses Against M2e The universal flu vaccine antigen, the ectodomain of matrix protein 2 (M2e), is not significantly immunostimulatory when administered on its own. In order to increase its immunogenicity, it was formulated using Ace-DEX microparticles (MPs), and then this M2e formulation was tested in vivo as part of a universal flu subunit vaccine. M2e was first encapsulated in three separate MPs (made by an emulsion via homogenization followed by solvent evaporation) composed of Ace-DEX with various relative cyclic acetal coverages (CAC; 20, 40, or 60%). The CAC determines the degradation rate of the MPs; higher CAC values mean slower degradation. cGAMP was used as the adjuvant in the vaccine formulation, and it was encapsulated in three separate emulsion MPs (made by homogenization) composed of the same three Ace-DEX polymers. BALB/c mice were immunized on Day 0 and Day 21 with the following groups: phosphate-buffered saline (PBS), soluble M2e alone, soluble M2e+blank MPs, soluble M2e+squalene emulsion (MF59-like AddaVax), soluble M2e+cGAMP MPs (20% CAC), soluble M2e+cGAMP MPs (40% CAC), soluble M2e+cGAMP MPs (60% CAC), M2e MPs (20% CAC)+cGAMP MPs (20% CAC), M2e MPs (20% CAC)+cGAMP MPs (40% CAC), M2e MPs (20% CAC)+cGAMP MPs (60% CAC), M2e MPs (40% CAC)+cGAMP MPs (20% CAC), M2e MPs (40% CAC)+cGAMP MPs (40% CAC), M2e MPs (40% CAC)+cGAMP MPs (60% CAC), M2e MPs (60% CAC)+cGAMP MPs (20% CAC), M2e MPs (60% CAC)+cGAMP MPs (40% CAC), or M2e MPs (60% CAC)+cGAMP MPs (60% CAC). The total IgG anti-M2e serum antibody titers, as well as anti-M2e IgG1 (Th2-bias) and IgG2a (Th1-bias) subtypes were measured (FIG. 34A-C). Significant results from this experiment were that the M2e MP formulations were more immunostimulatory than any of the soluble M2e formulations, including the one adjuvanted with clinically relevant MF59-like squalene AddaVax emulsion, which is similar to the adjuvant used in the FDA-approved FLUAD seasonal flu vaccine. Furthermore, among the groups adjuvanted with cGAMP MPs, the cGAMP MPs (60% CAC) trended toward the highest antibody titers when combined with M2e MPs composed of Ace-DEX with all three CACs. Finally, robust antibody titers were detected out to at least Day 70, which was 7 weeks following the boost immunization. 7 weeks is a significant fraction of a typical flu season. In a follow-up experiment BALB/c mice were again immunized on Day 0 and Day 21, but this time with groups of highest interest from the first experiment, with an emphasis on cGAMP MPs (60%): PBS, soluble M2e alone, soluble M2e+squalene emulsion (MF59-like AddaVax), soluble M2e+cGAMP MPs (60% CAC), M2e MPs (20% CAC)+cGAMP MPs (60% CAC), M2e MPs (40% CAC)+cGAMP MPs (60% CAC), M2e MPs (60% CAC)+cGAMP MPs (60% CAC), and co-encapsulated M2e/cGAMP MPs (60% CAC). The total IgG anti-M2e serum antibody titers, as well as anti-M2e IgG1 (Th2-bias) and IgG2a (Th1-bias) subtypes were again measured (FIG. 35A-C). The M2e encapsulated in separate MPs as the cGAMP again led to higher antibody titers than the soluble M2e+MF59-like squalene emulsion, as well as titers at least as high, if not higher than the M2e and cGAMP co-encapsulated in the same MPs. At Day 28, the mice from this study were euthanized, and their spleens were harvested. Splenocytes were restimulated with the M2e peptide, and the subsequent cellular response was assessed by looking at soluble cytokine (IFN-γ, IL-2, and IL-6) production by ELISA (FIG. 35D) and IFN-γ or IL-2-forming cells by ELISPOT (FIG. 35E). These results demonstrated that soluble M2e+MF59-like squalene emulsion did not lead to any cellular response, while the M2e MPs (40%)+cGAMP MPs (60%), M2e MPs (60%)+cGAMP MPs (60%), and co-encapsulated M2e/cGAMP MPs (60%) lead to significant cellular responses.

Figure 36:
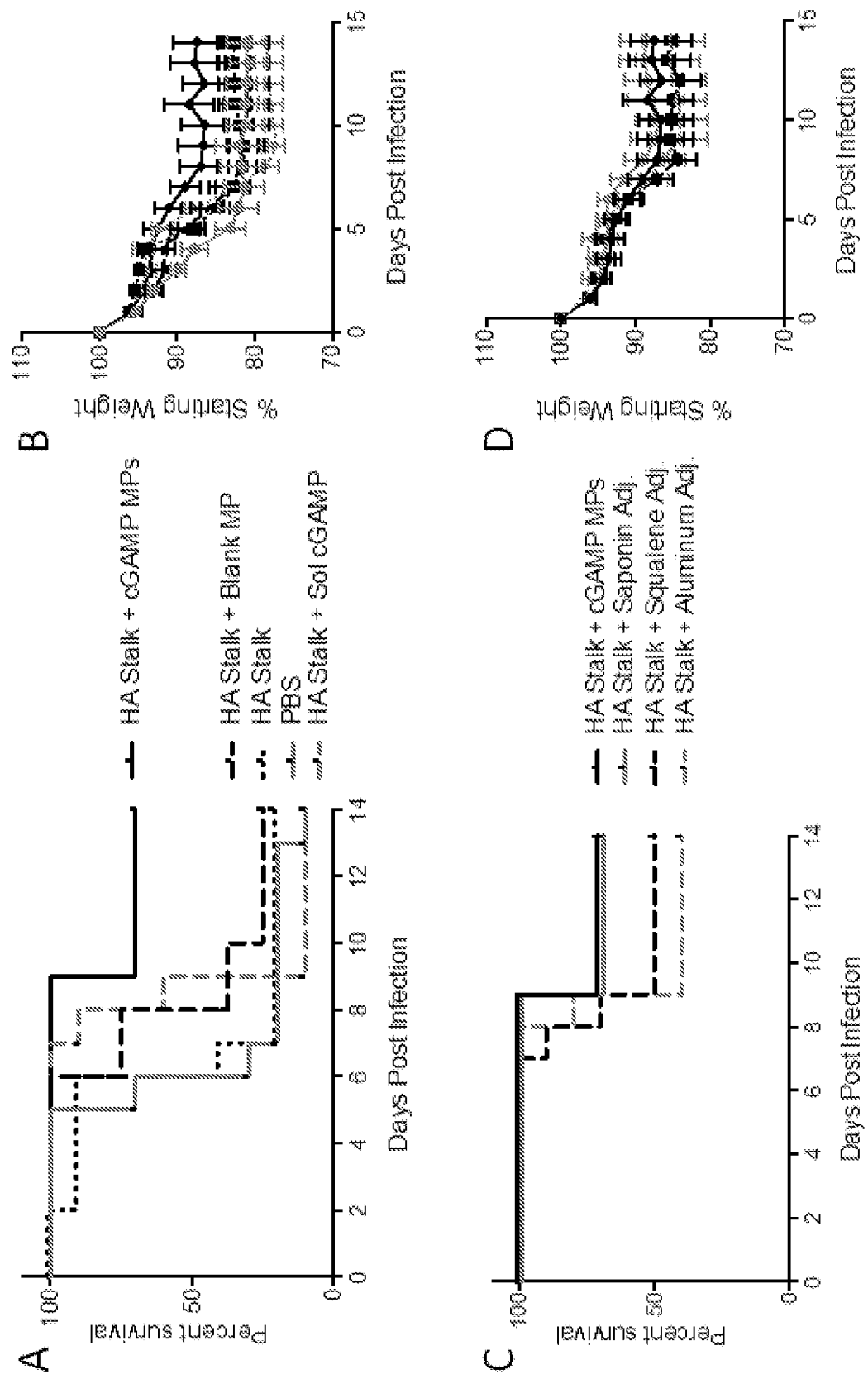
FIG. 36. Ace-DEX cGAMP MP improve efficacy of a universal influenza vaccine: Eight week old female C57BL/6 mice were immunized with PBS or with 10 μg of a stabilized HA stalk protein from A/Brisbane/59/07 alone or adjuvanted with 10 μg of soluble cGAMP, 10 μg cGAMP MPs, an equivalent MP dose of blank Ace-DEX MPs, a saponin based adjuvant (Quil A), a squalene based adjuvant (MF59-like AddaVax), or an aluminum based adjuvant (Alhydrogel). A boost was administered 21 days later. One month post boost, mice were infected intranasally with 2,000 ffu of A/Puerto Rico/8/1934/H1N1. Survival (A, C) and weight loss (B, D) was monitored for 14 days (n=10+ SD).

Example 13: Ace-DEX cGAMP Microparticles Adjuvanting HA Stalk Provides Superior Protection Against Homosubtypic Infection The stalk region of influenza hemagglutinin (HA) is highly conserved, and has be the subject of extensive study as a 'universal' vaccine adjuvant. However, these proteins are poorly immunogenic, and require a potent adjuvant in order to provide protective immunity. Using a previously described stabilized HA stalk protein, protection provided by the following vaccine formulations was tested: unadjuvanted HA stalk, HA stalk plus soluble cGAMP or electrosprayed Ace-DEX microparticle (MP)-encapsulated cGAMP, or HA stalk+electrosprayed blank MPs. Mice received a prime and then a boost with the same formulation 21 days later, and were challenged with a lethal dose of A/Puerto Rico/8/34 H1N1 virus on day 56. Survival and weight loss was monitored for 14 days post infection (FIG. 36A-B). Soluble cGAMP, unadjuvanted HA stalk protein, and blank MPs provided no survival advantage over unimmunized mice. cGAMP MPs, on the other hand, protected 70% of infected animals, and reduced weight loss following infection.

In order to assess how Ace-DEX cGAMP MPs compare to current 'state-of-the-art' adjuvants, animals were immunized as above with HA stalk protein adjuvanted with cGAMP MPs, a saponin-based Quil A adjuvant (used in Matrix M), a squalene based adjuvant (similar to MF59), and an aluminum based adjuvant (Alhydrogel). These formulations reflect the majority of adjuvant formulation currently used clinically. However, only the squalene based adjuvant is currently used in the FDA-approved FLUAD inactivated influenza vaccine, and this formulation is only recommended for elderly individuals. Following lethal challenge, cGAMP MPs and saponin based adjuvants provided the most robust protection, followed by squalene, then aluminum based adjuvants (FIG. 36C-D). These results indicate that cGAMP MPs provide equivalent or superior protection compared to conventional vaccine adjuvants, and outperformed adjuvants currently used in influenza vaccine formulations.

Figure 37A:
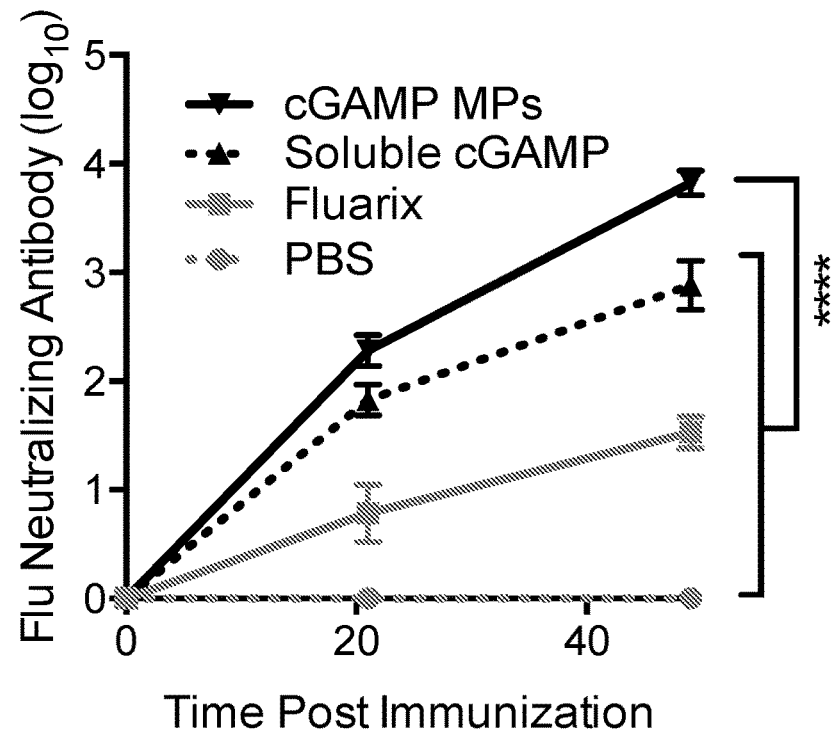
FIG. 37. Ace-DEX cGAMP MPs provide superior protection compared to commercial flu vaccine in ferrets: Eighteen week old male ferrets were immunized intramuscularly with PBS, the 2016 formulation of Fluarix, or 15 μg of recombinant hemagglutinin from strain A/California/07/09 adjuvanted with 15 μg of soluble cGAMP or with 15 μg cGAMP MPs. Animals received a boost with the same formulation 4 weeks later. Serum was prior to immunization, as well as 21 and 56 days post immunization to assess virus neutralizing antibody titers (A). Two months after the initial immunization, animals were challenged intranasally with 1.25×10$^7$ ffu of influenza strain A/California/07/09. Animal weight (B) and periodic combined clinical index (a measure of changes in respiratory effort and activity level) (C) was monitored daily for 19 days. Nasal lavage was collected on days 2 (D) and 4 (E) for analysis of viral load. (n=4+SD).
Figure 37B:
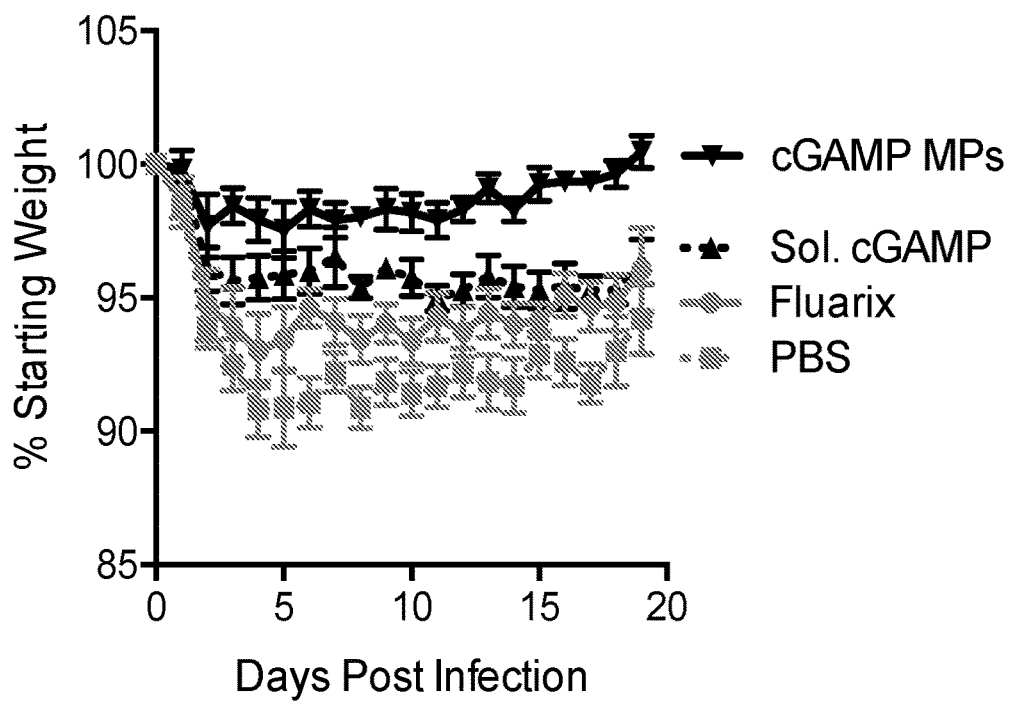
Figure 37C:
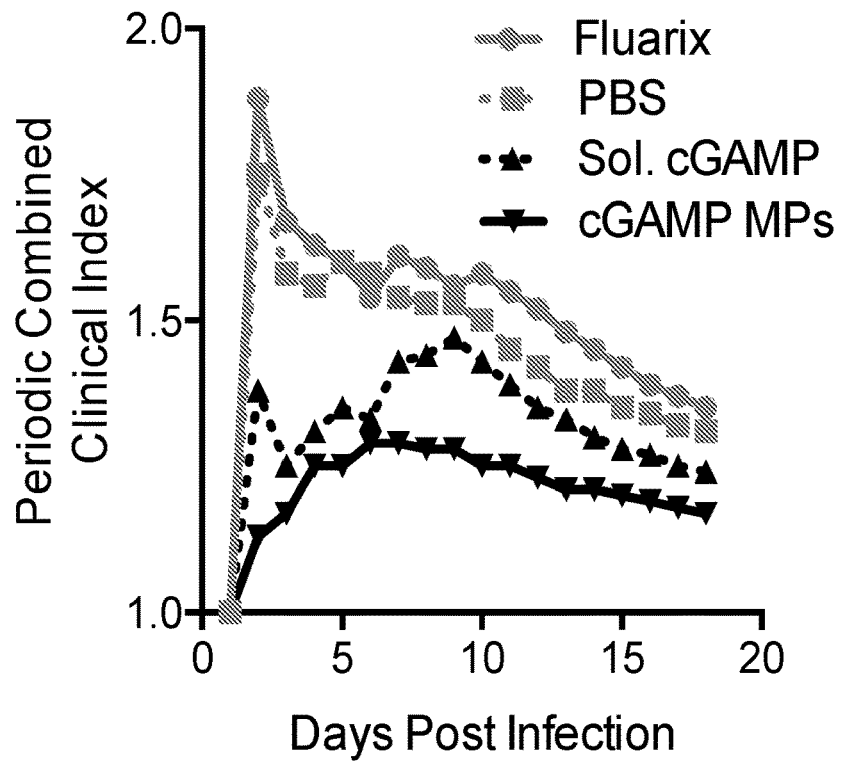
Figure 37D:
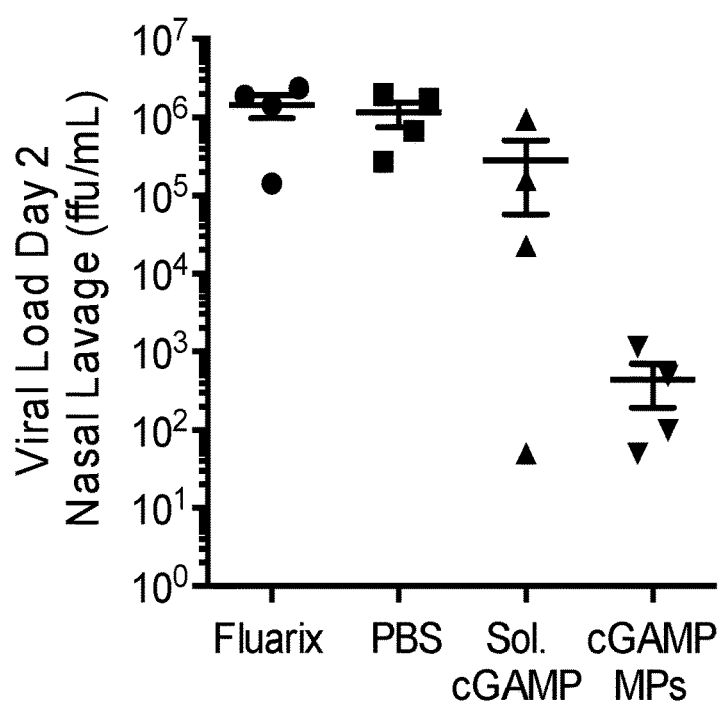
Figure 37E:
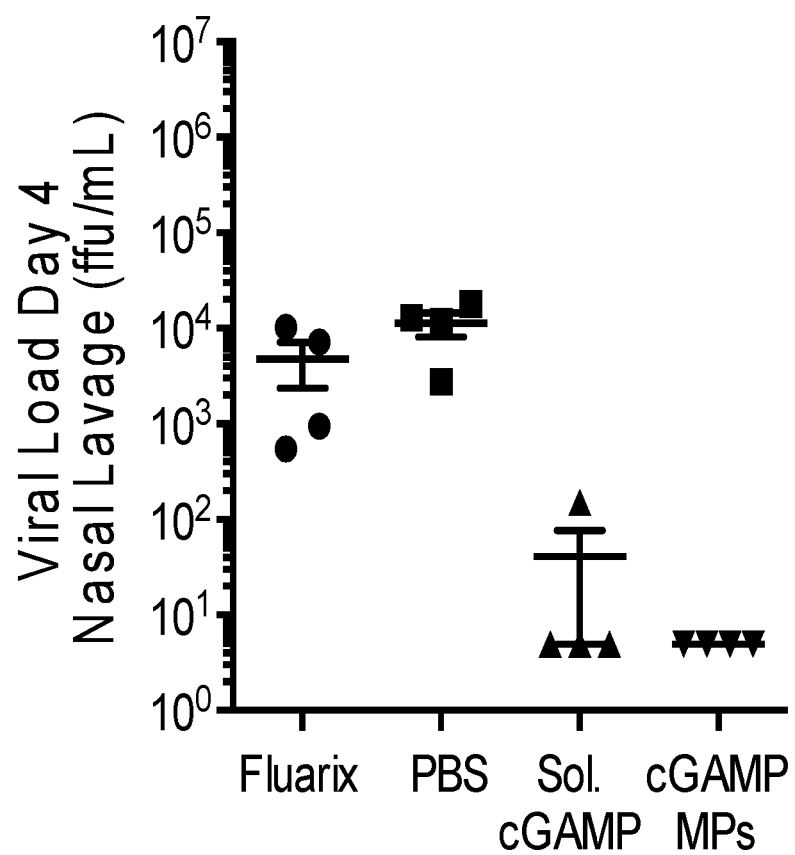

Example 14: Ace-DEX cGAMP Microparticles Provide Superior Protection Compared to an Existing Flu Vaccine in Ferrets Ferrets represent the gold-standard for studying pathogenicity and transmissibility of human and avian influenza viruses. In order to examine how an electrosprayed Ace-DEX cGAMP MP adjuvanted recombinant protein influenza vaccine compares to existing vaccines used in the clinic, ferrets were left unimmunized, immunized with recombinant hemagglutinin (HA) protein from influenza strain A/California/07/09 adjuvanted with soluble cGAMP or Ace-DEX microparticle (MP)-encapsulated cGAMP, or with the 2016 formulation of FDA-approved Fluarix, a quadrivalent inactivated influenza vaccine. Animal received a boost with the same formulation 28 days later, and virus neutralizing antibodies were assessed prior to immunization, as well as 21 and 56 days immunization (FIG. 37A). Ace-DEX cGAMP MPs provided the most robust virus neutralizing antibody responses, generating neutralizing titers 10-fold higher than formulation adjuvanted with soluble cGAMP, and greater than 100-fold higher than those achieved using the commercial Fluarix vaccine. To assess protection, ferrets were challenged on day 81 post immunization with a sublethal dose of influenza strain A/California/07/09. Weight loss and clinical symptoms (a composite score of activity level and respiratory effort) were monitored for 19 days post infection, and nasal washes were collected on days 2 and 4 post challenge to assess viral burden (FIG. 37B-E). Both recombinant HA+soluble cGAMP, and Fluarix immunized groups displayed significant weight loss after infection, which was only marginally improved compared to unimmunized ferrets. In contrast, Ace-DEX cGAMP MPs almost completely prevented weight loss post infection. Similarly, Fluarix did not reduce viral load in nasal washes taken on day 2 and 4 post infection, compared to unimmunized controls, while only 1 soluble cGAMP immunized animal displayed decreased viral load on day 2 post immunization. Ace-DEX cGAMP MPs, on the other hand, resulted in a greater than 1,000-fold decrease in viral load on day 2, and had completely cleared the virus by day 4 post infection. These results indicate that recombinant HA protein adjuvanted with Ace-DEX cGAMP MPs provides near complete protection in the gold-standard ferret model of influenza infection, and significantly outperformed the state of the art flu vaccine.

Figure 38:
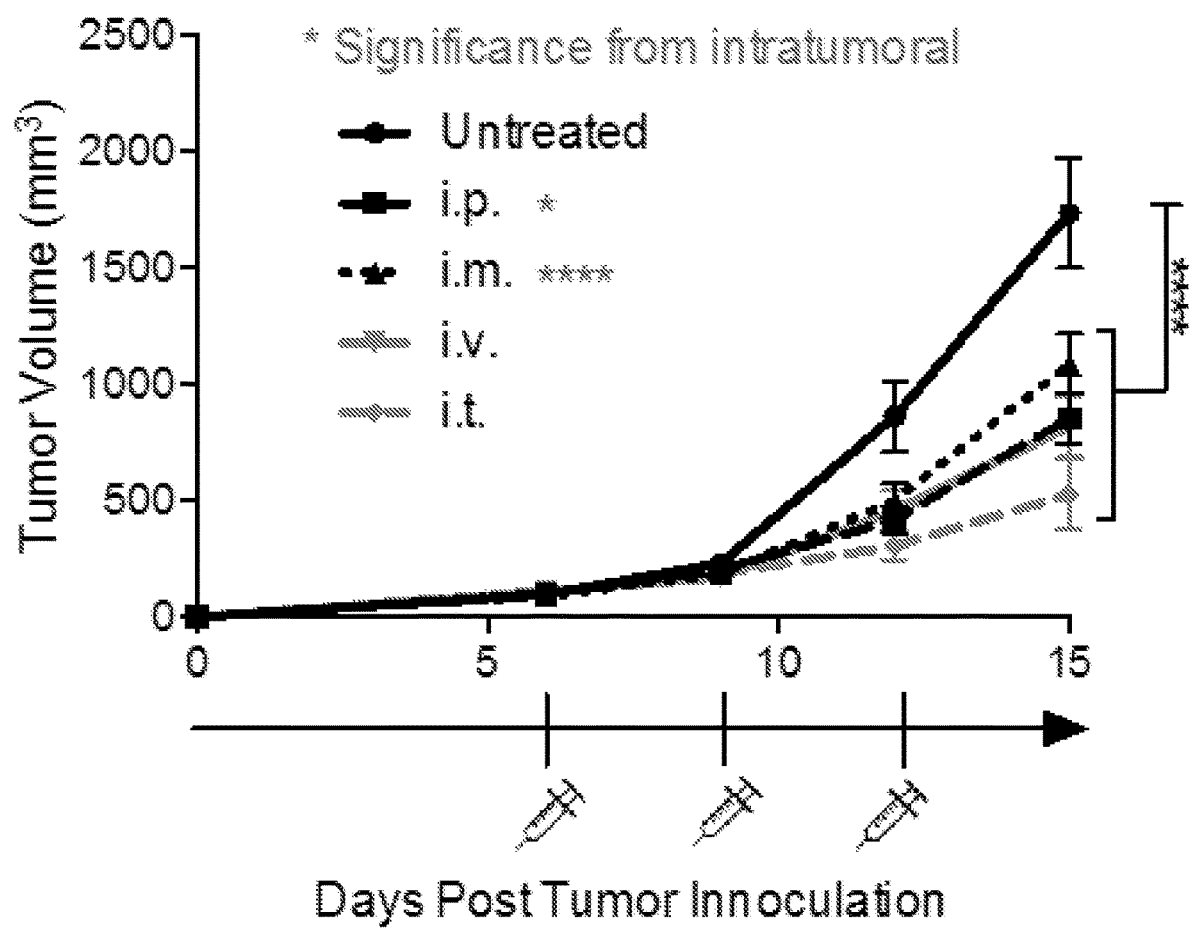
FIG. 38. Ace-DEX encapsulated cGAMP is an effective cancer immunotherapy when delivered through multiple routes: Eight week old female C57BL/6 mice were injected with 200,000 B16F10 melanoma cells subcutaneously. Treatments commenced once tumors were palpable, six days post instillation. Tumors were left untreated, or treated with 10 μg of Ace-DEX cGAMP MPs delivered intraperitoneally (i.p.), intramuscularly (i.m.), intravenously (i.v.) or intratumorally (i.t.) on days 6, 9 and 12. Tumor volume was measured every 3 days (n=12-15+SD, *p<0.05, ****p<0.0001).
Figure 39A:
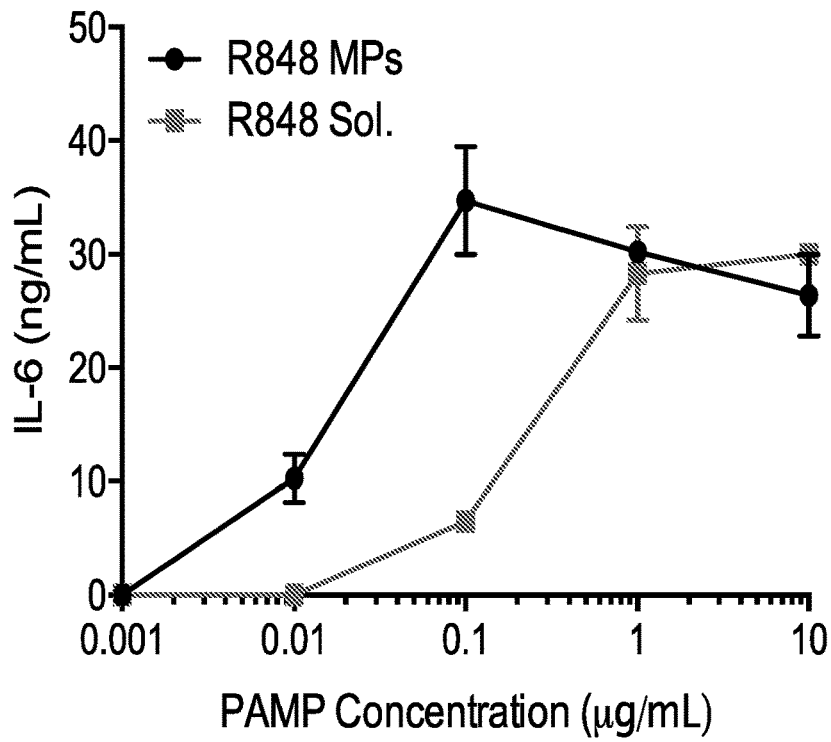
FIG. 39. Ace-DEX delivery of PAMPs provides dose sparing of cytokine responses: Bone marrow derived dendritic cells were cultured from C57BL/6 mice, then left stimulated with the indicated dose of soluble or Ace-DEX encapsulated (A, B) resiquimod (R848), (C, D) imiquimod (R837), (E, F) murabutide, or (G, H) cGAMP. Eighteen hours later supernatants were collected and analyzed for IL-6 and TNF. (n=2±SEM).
Figure 39B:
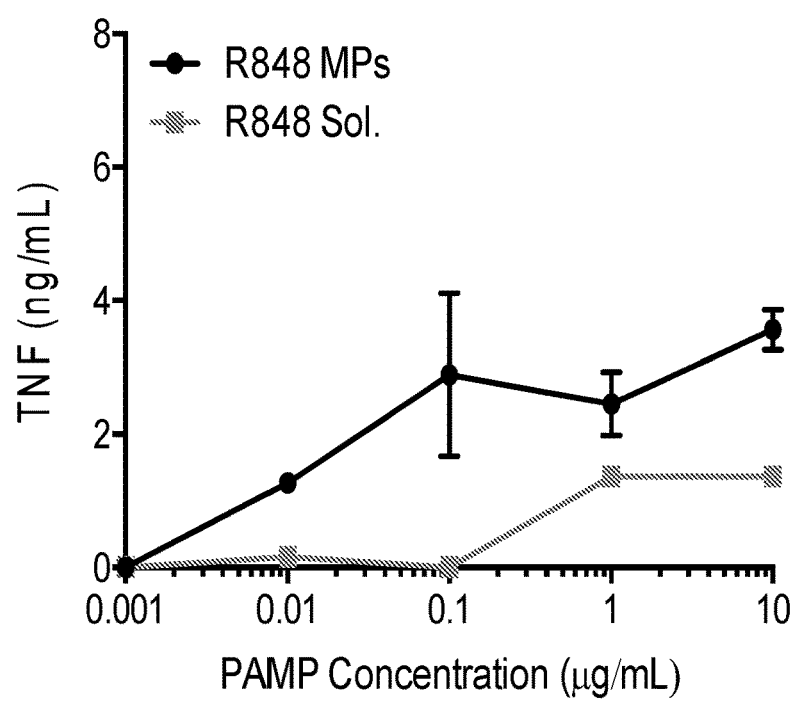
Figure 39C:
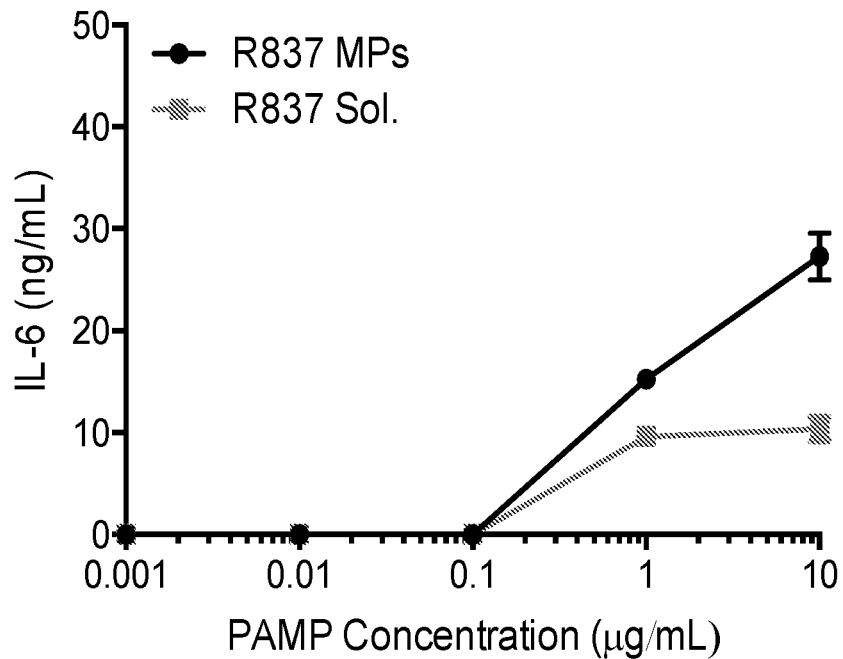
Figure 39D:
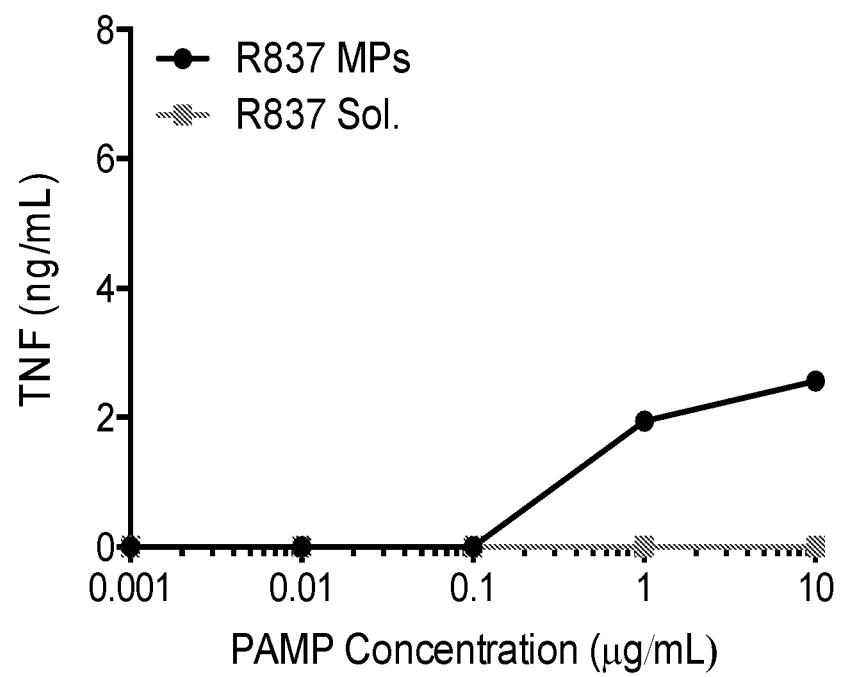
Figure 39E:
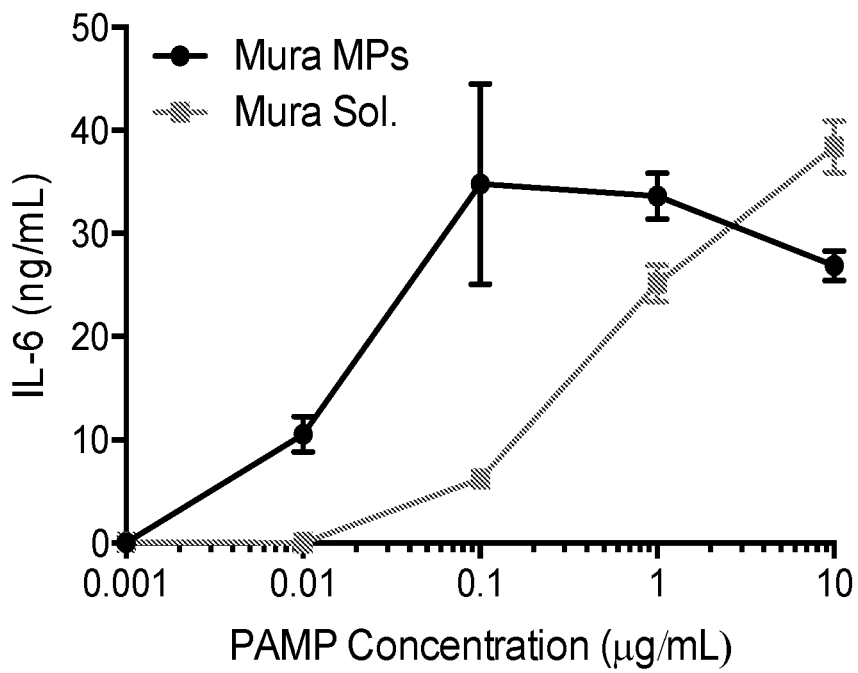
Figure 39F:
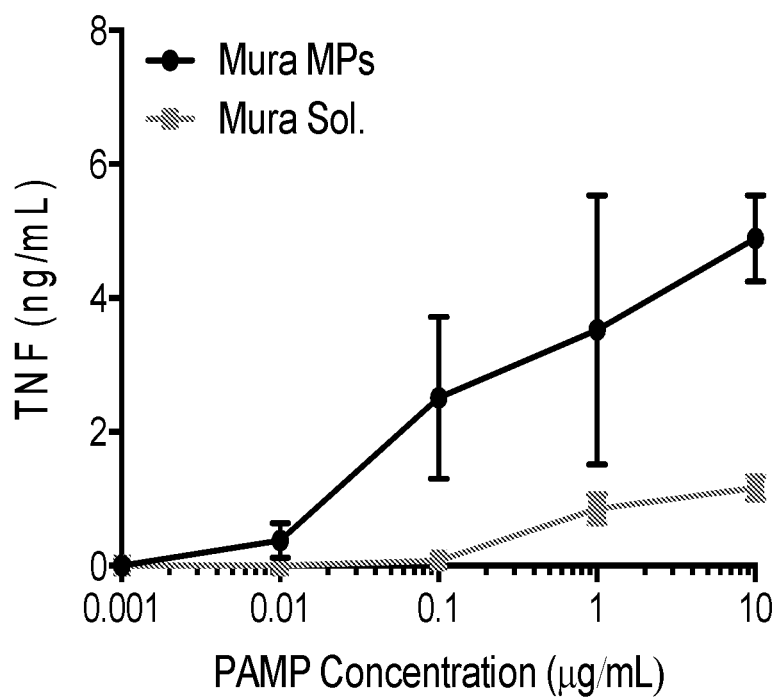
Figure 39G:
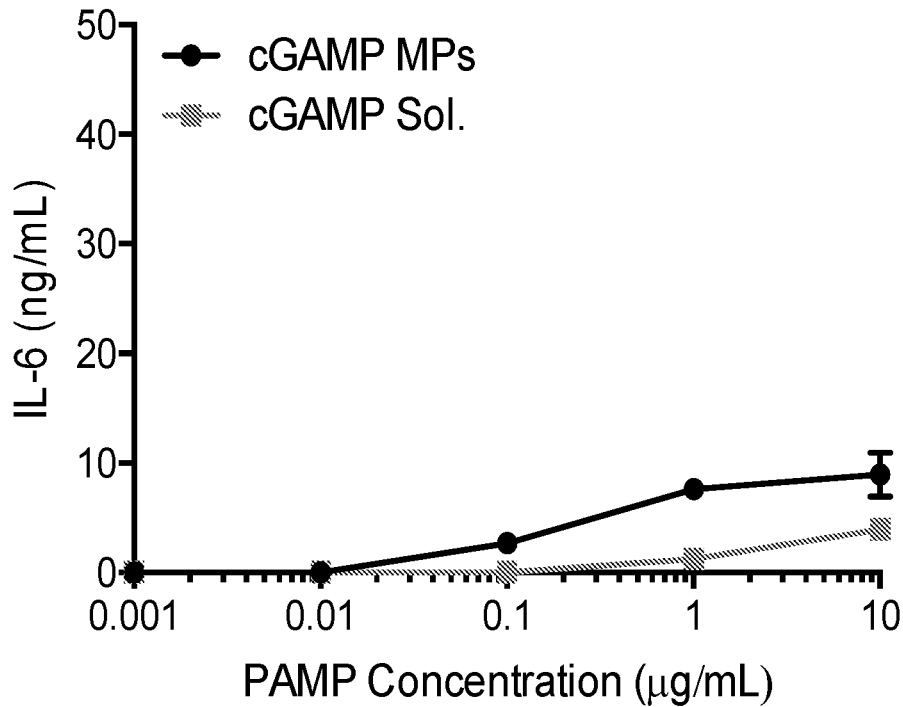
Figure 39H:
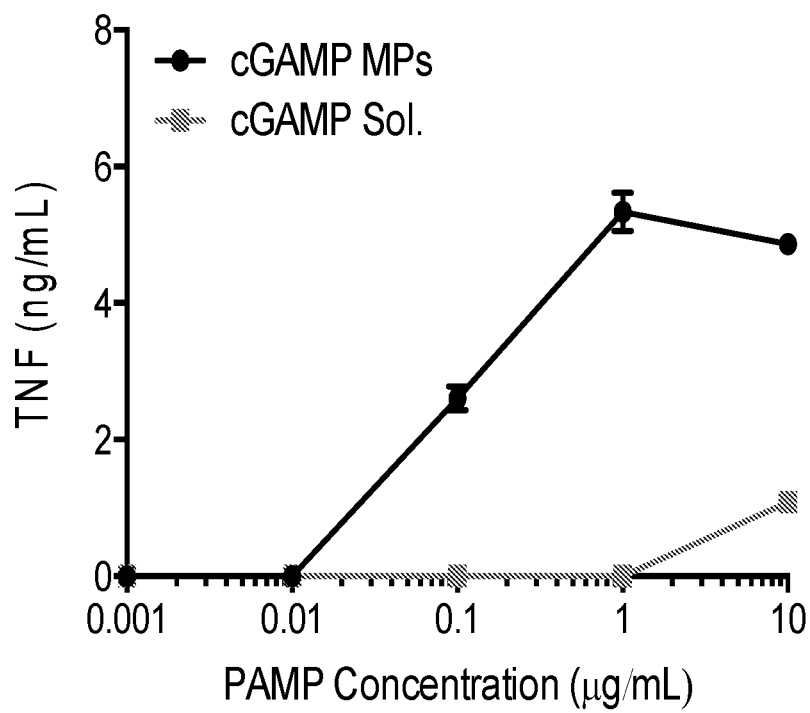

Example 15: Ace-DEX cGAMP Microparticles are an Effective Cancer Immunotherapy when Delivered Through Multiple Routes It was demonstrated that intravenously (i.v.) delivered electrosprayed Ace-DEX cGAMP microparticles (MPs) are a potent cancer immunotherapy. A study assessing which route of delivery provides optimal anti-tumor effects was completed. Eight-week-old C57BL/6 mice were injected subcutaneously with B16F10 melanoma cells. Tumors were left untreated, or treated with 10 µg of Ace-DEX MP-encapsulated cGAMP on 6, 9, and 12 days post tumor inoculation via intratumoral (i.t.), intraperitoneal (i.p.), intramuscular (i.m.), or i.v. routes. Tumor volume was assessed every 3 days (FIG. 38). On day 15, all routes significantly reduced tumor volume compared to untreated tumors. Intratumoral delivery resulted in optimal responses, which were significantly superior to i.p. and i.m. delivery. These data demonstrate that Ace-DEX cGAMP MPs are a potent cancer immunotherapy when delivered through multiple routes, and that optimal responses can achieved through direct i.t. delivery.

Figure 40A:
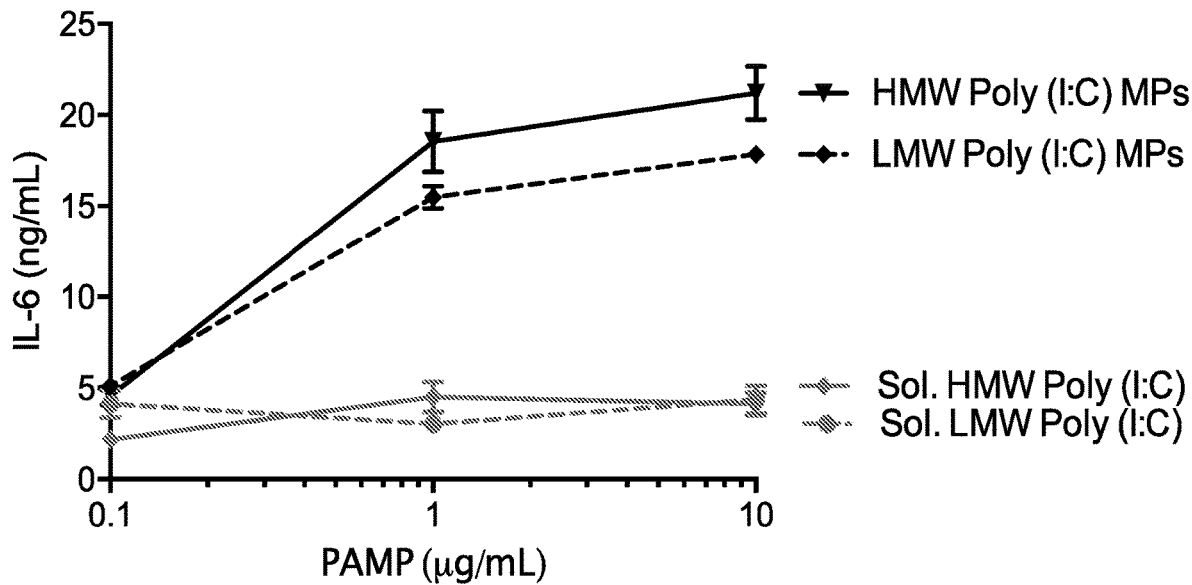
FIG. 40. Ace-DEX delivery of poly (I:C) provides dose sparing of cytokine responses: Primary peritoneal macrophages were collected from C57BL/6 mice, then stimulated with the indicated dose of soluble or Ace-DEX encapsulated low molecular weight (LMW) or high molecular weight (HMW) poly (I:C). Eighteen hours later supernatants were collected and analyzed for IL-6 (A) and TNF (B). (n=2±SEM).
Figure 40B:
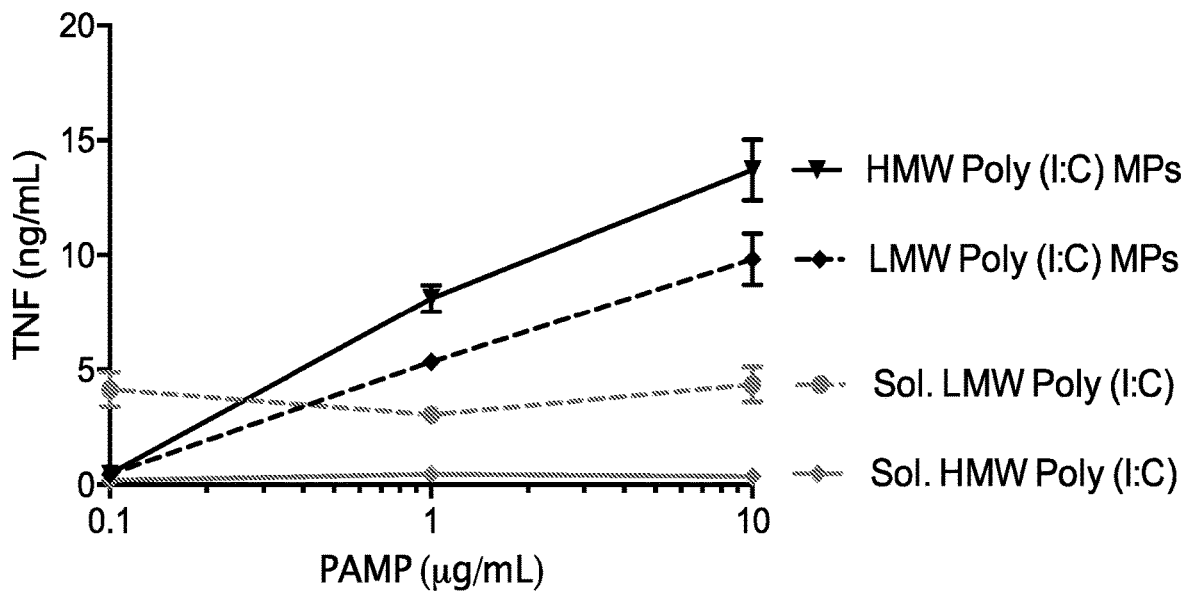

Example 16: Delivery of PAMP Adjuvants Via Ace-DEX Microparticles Provides Dose Sparing, Enhances Biological Activity, and Delays Tumor Growth In Vivo In order to assess the broad applicability of delivery of pathogen-associated molecular patterns (PAMPs) to intracellular targets using the Ace-DEX microparticle (MP) platform, and to demonstrate the ability to encapsulate multiple chemically diverse PAMPs, murabutide (nucleotide-binding oligomerization domain 2; NOD2 agonist), polyinosinic-polycytidylic acid (poly (I:C); toll-like receptor (TLR)-3/retinoic acid-inducible protein I (RIG-I) agonist), resiquimod (TLR-7/8 agonist), and imiquimod (TLR-7 agonist) were encapsulated. Critically, engagement of each pathway targeted by these PAMPs has been shown to have anti-cancer activity in the clinic. In order to assess whether bioactivity of each PAMP was enhanced through encapsulation within electrosprayed Ace-DEX MPs, bone marrow-derived dendritic cells (BMDCs) (FIG. 39A-H) or peritoneal macrophages (FIG. 40A-B) were treated with increasing doses of soluble or Ace-DEX MP-encapsulated PAMPs. As poly (I:C) can encompass a wide range of molecular weights, both high molecular weight and low molecular weight species were examined. Encapsulation of all PAMPs resulted both in increases in the maximal IL-6 and TNF responses and in significant dose sparing, as evidenced by a leftward shift in the dose curves.

Figure 41A:
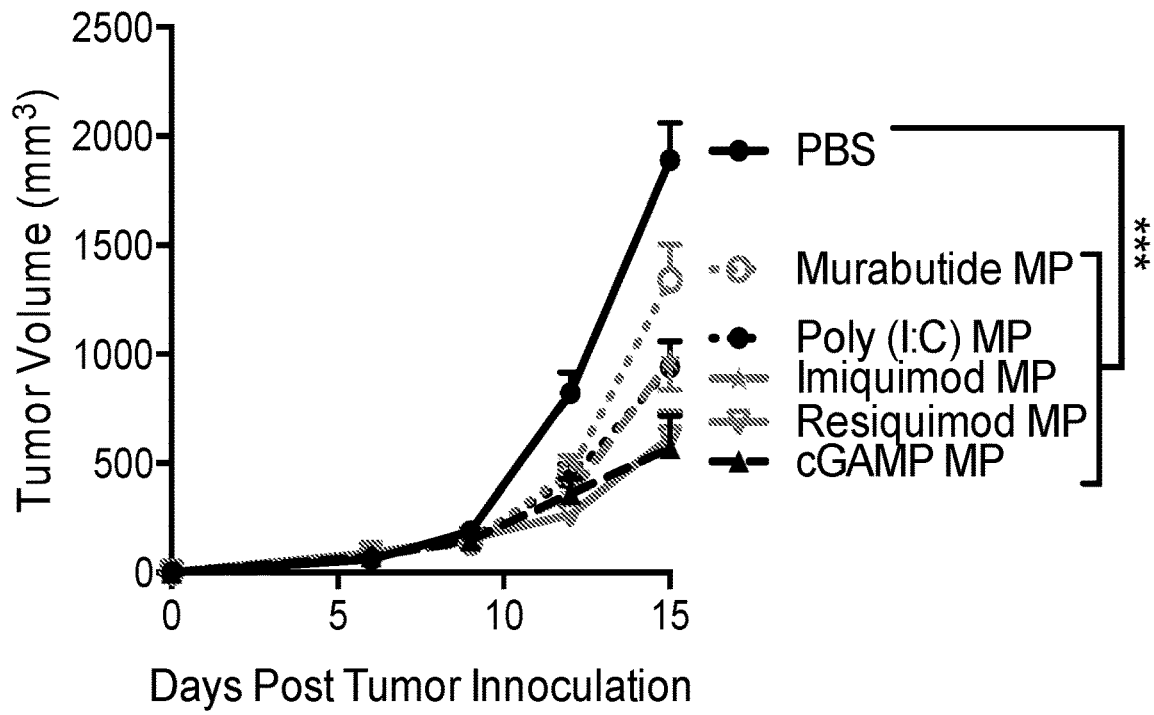
FIG. 41. Ace-DEX encapsulated PAMPs are efficient cancer immunotherapies: Eight week old female C57BL/6 mice were injected with 200,000 B16F10 melanoma cells subcutaneously. Treatments commenced once tumors were palpable, six days post inoculation. Infratemporal injections of PBS or 10 μg of Ace-DEX encapsulated murabutide, poly (I:C), cGAMP, resiquimod, or imiquimod were administered on days 6, 9 and 12 post tumor instillation. Tumor volume was measured every 3 days (A). Alternative tumors were treated with the indicated dose of Ace-DEX cGAMP MPs (B) or Ace-DEX resiquimod MPs (C). (n=10±SD, *p<0.001, **p<0.0001).
Figure 41B:
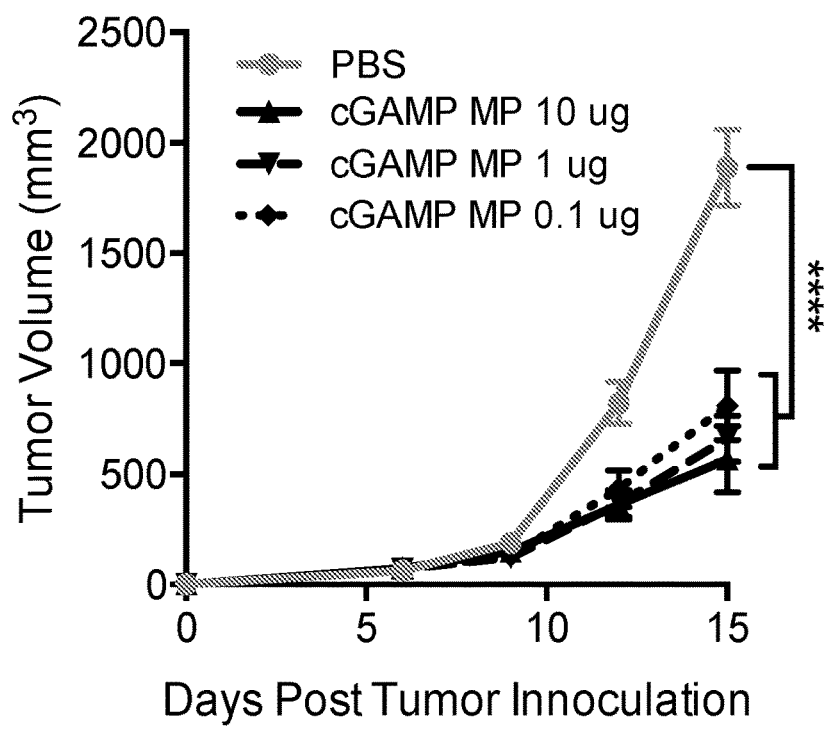
Figure 41C:
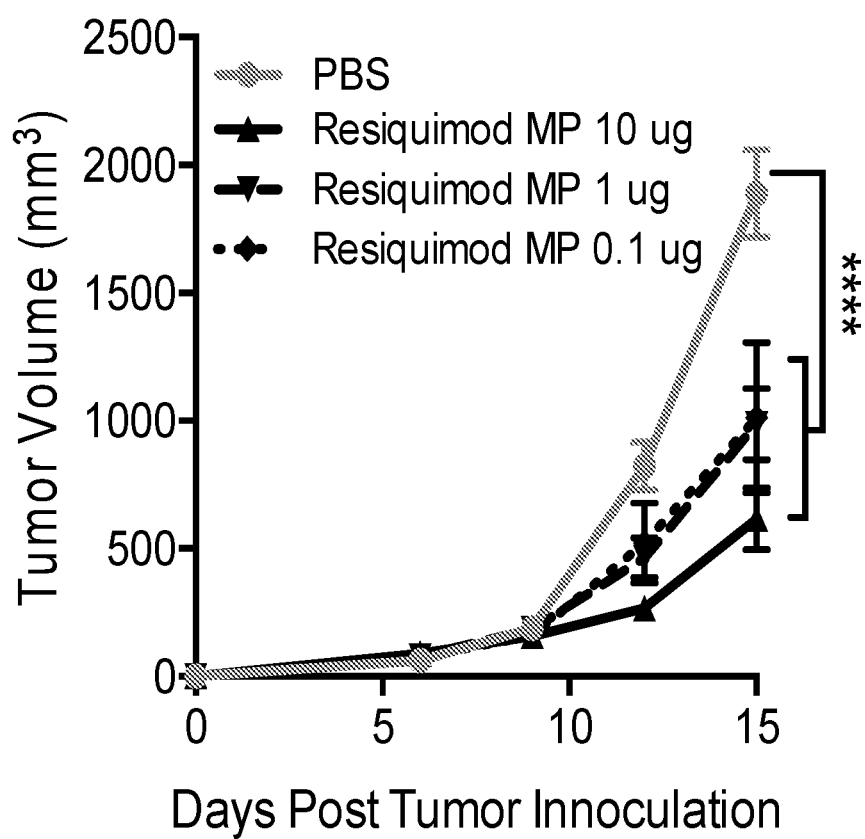

The efficacy of Ace-DEX PAMP MP formulations as a cancer immunotherapy was examined via the B16F10 melanoma model. Eight-week-old C57BL/6 mice were injected subcutaneously with B16F10 cells. Six, nine and twelve days post tumor inoculation, tumors were injected with phosphate-buffered saline (PBS), or 10 µg of Ace-DEX MP-encapsulated murabutide, poly (I:C), cGAMP, resiquimod (R848), or imiquimod (R837). Tumor volume was measured every 3 days (FIG. 41A). All formulations of Ace-DEX MP-encapsulated PAMPs significantly reduced tumor size on day 15 post tumor inoculation. The dose sparing of two lead Ace-DEX PAMP MP candidates (cGAMP and resiquimod) was assessed. In addition to the 10 µg dose described above, 1 and 0.1 µg doses were also assessed. Critically, for both cGAMP (FIG. 41B) and resiquimod (FIG. 41C), all doses significantly reduced tumor volume compared to PBS control. In addition, no differences in efficacy were observed as the dose was decreased. These results indicate that Ace-DEX delivery of PAMPs is a potent and effective cancer immunotherapy.

Figure 42:
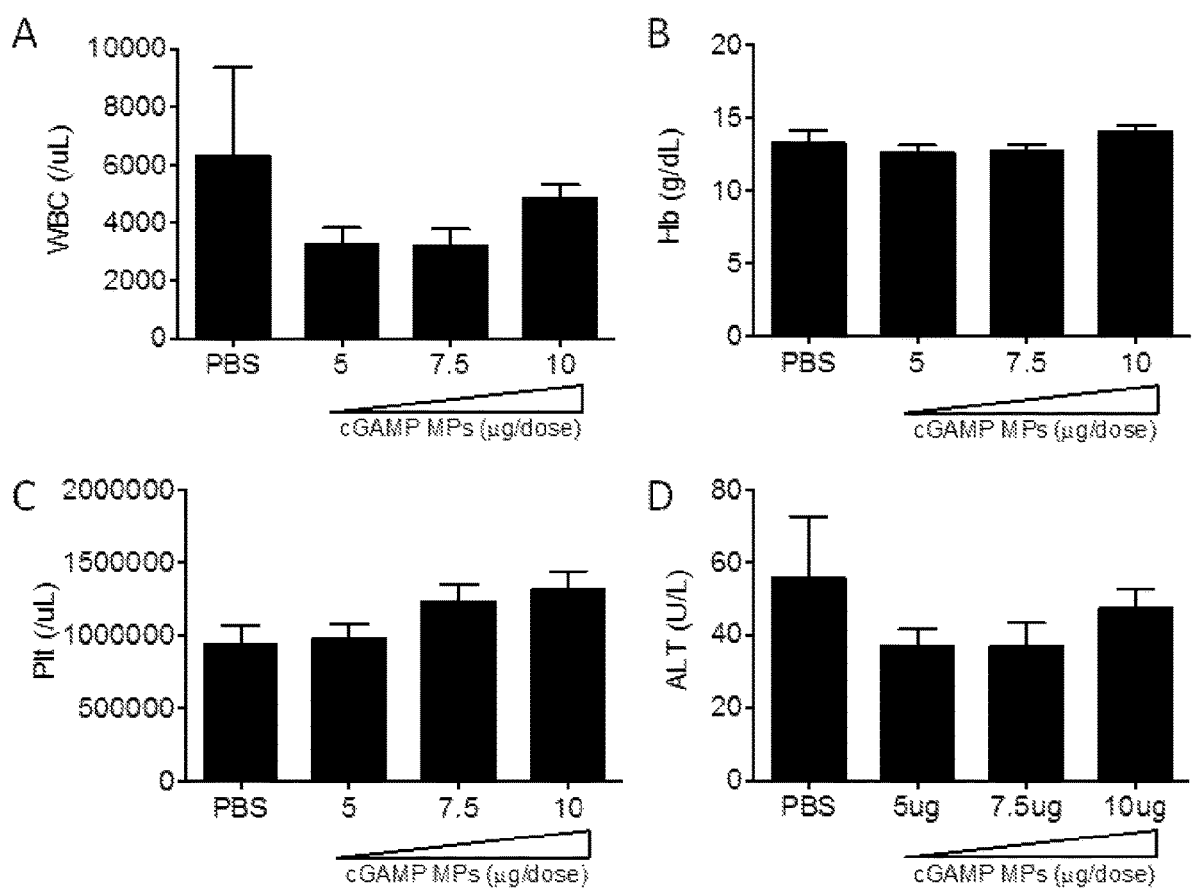
FIG. 42. Ace-DEX cGAMP MPs do not induce hematological changes, or liver toxicity in a model of autoimmunity. MOG(35-55) peptide emulsified in complete Freund adjuvant (4 mg/mL) was subcutaneously injected to sites adjacent to mouse tails. On days 0 and 2 post injection, 400 ng of pertussis toxin was injected intravenously (i.v.). After the onset of symptoms (Day 9) mice were left untreated, or received 5, 7.5 or 10 μg of cGAMP MPs (MP dose 500-1000 μg) i.m. Blood was collected 24 hours post injection and total white blood cells (WBC) (A), hemaglobin (Hg) (B), and platelet numbers (Plt) (C) were assessed. Liver toxicity was also assessed by alanine aminotransferase (ALT) activity (D).

Example 17: Ace-DEX cGAMP Microparticles do not Induce Hematological Changes or Liver Toxicity in a Model of Autoimmunity Treatment with electrosprayed Ace-DEX cGAMP microparticles (MPs) decreases symptoms in an experimental autoimmune encephalomyelitis (EAE) mouse model of multiple sclerosis. The stimulator of interferon genes (STING) pathway, the target of cGAMP, has been implicated in autoimmunity, and concerns have been raised about the safety of targeting this pathway for therapeutic interventions, particularly in autoimmune populations. In order to assess toxicity in a model of active autoimmunity, EAE was induced in C57BL/6 mice through subcutaneous injection of myelin oligodendrocyte glycoprotein (MOG) (35-55) peptide emulsified in complete Freund's adjuvant (4 mg/mL) at the base of the mouse tail. On days 0 and 2 post injection, 400 ng of pertussis toxin was injected intravenously (i.v.). After the onset of symptoms on Day 9 mice were left untreated, or received 5, 7.5, or 10 µg of Ace-DEX MP-encapsulated cGAMP (MP dose 500-1000 µg) intramuscularly. Blood was collected 24 hours post injection and total white blood cells (WBC), hemoglobin (Hg), and platelet numbers (Plt) were assessed (FIG. 42A-C). Liver toxicity was also assessed by alanine aminotransferase (ALT) activity (FIG. 42D). No hematological changes were observed with any of the doses tested. Similarly, no elevation in ALT activity was observed. Together these results indicate that Ace-DEX cGAMP MPs do not induce significant toxicity in a model of ongoing auto-immunity.

Figure 43:
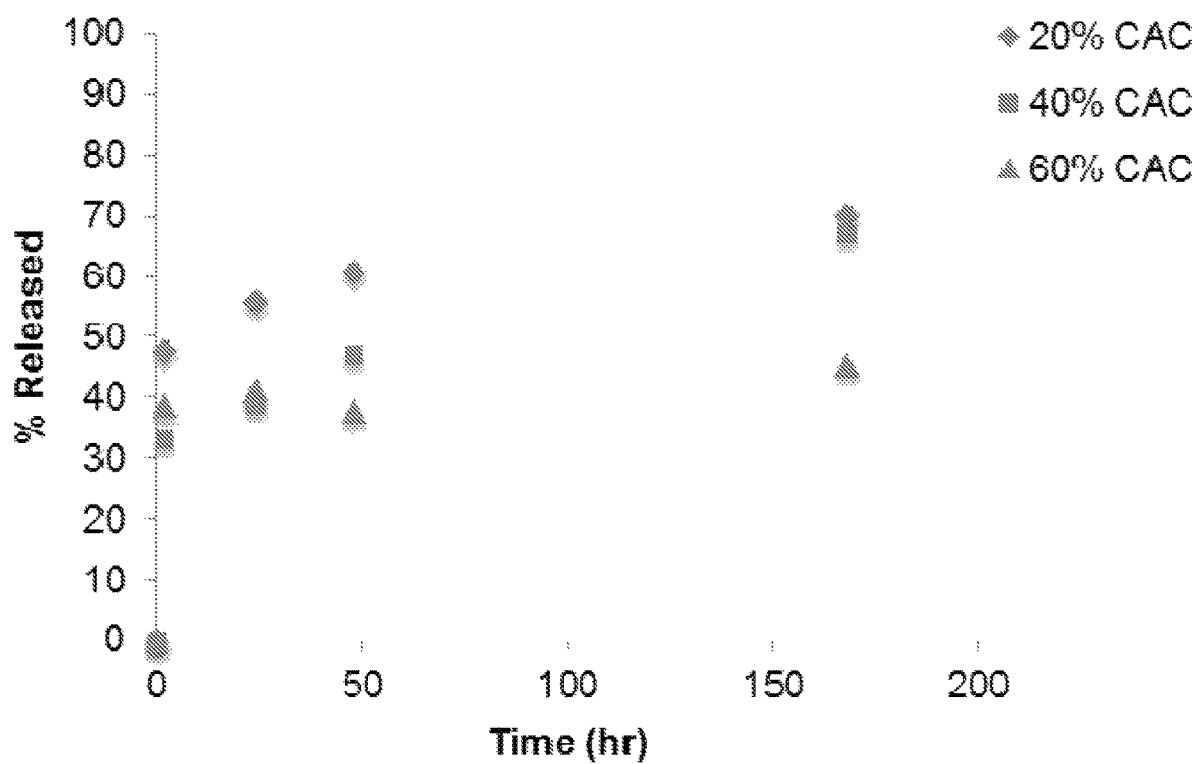
FIG. 43. Release profile of anti-PD-L1 antibody from MPs can be tuned based on Ace-DEX polymer cyclic acetal coverage. Ace-DEX MPs with various Ace-DEX relative cyclic acetal coverage (CAC) encapsulating an anti-PD-L1 antibody were incubated at physiological conditions (pH 7.4 and 37° C.) in phosphate-buffered saline. The percent release of the antibody into the supernatant was assessed out to 168 hours.

Example 18: Anti-PD-L1 Antibody can be Encapsulated within Ace-DEX Microparticles and its Affinity for Cell Surface Receptor PD-L1 is Maintained Antibodies against checkpoint molecules such as programmed cell death protein 1 (PD-1), programmed death-ligand 1 (PD-L1), and cytotoxic T-lymphocyte antigen 4 (CTLA-4) have become increasingly popular as cancer immunotherapies since the FDA approved the first one in the early 2010s. Most, if not all of these antibody therapies are administered intravenously (i.v.). The clearance rate of the antibodies from the bloodstream is relatively rapid, requiring frequent i.v. infusions (once every few weeks). Encapsulation of the antibodies within a delivery vehicle such as Ace-DEX microparticles (MPs) would enable sustained delivery of antibodies over time. This has positive implications for dose-sparing, increased patient adherence to the dosage schedule, fewer side effects, lower therapeutic index, and longer time in the therapeutic window. Here an anti-PD-L1 antibody has been encapsulated within Ace-DEX MPs using a water-in-oil-in-water emulsion formed by homogenization, followed by solvent evaporation (at an efficiency of >40%). Ace-DEX polymers of varying relative cyclic acetal coverages (CAC), including 20, 40, and 60%, were used. The release profile of the anti-PD-L1 antibody from the Ace-DEX MPs, when incubated at physiological conditions (pH 7.4 and 37° C.), could be tuned based on the polymer CAC (FIG. 43). Furthermore, the antibodies maintained >70% affinity for its target PD-L1 protein (as measured by ELISA) after 1 week incubation at physiological conditions.

All publications, patent applications, patents and other references cited herein are incorporated by reference in their entireties for the teachings relevant to the sentence and/or paragraph in which the reference is presented.

TABLE 1

Table 1. Final cGAMP loading was quantified by HPLC.

| Formulation | Nominal cGAMP Loading (µg/mg) | Final cGAMP Loading (µg/mg) | Hydrodynamic Diameter (µm) | Zeta Potential (mV) |
|---|---|---|---|---|
| Electrospray Ace-DEX MPs | 4.8 | 5.2 | 1.54 ± 0.47 | −32.0 ± 0.7 |
| Electrospray PLGA MPs | 4.8 | 3.0 | 2.89 ± 0.69 | −27.1 ± 1.7 |
| Emulsion Ace-DEX MPs | 10.0 | 4.1 | 0.77 ± 0.03 | −34.5 ± 0.3 |
| Liposome | 45.0 | 13.7 | 0.46 ± 0.04 | +25.5 ± 1.4 |

Hydrodynamic diameter and zeta potential were determined using a Zetasizer Nano Z.
Data are reported as mean ± SEM (n = 3).
Ace-DEX = acetalated dextran;
PLGA = poly(lactic-co-glycolic acid);
MPs = microparticles.

What is claimed is:

1. A method of ameliorating, alleviating, decreasing symptom(s), or delaying progression of an infectious disease, cancer, or an autoimmune disorder that requires activation of the stimulator of interferon genes (STING) pathway, comprising administering to a subject in need thereof an effective amount of a composition comprising:
   a) acetalated dextran;
   b) an agonist of the stimulator of interferon genes (STING) receptor and/or a different immunostimulatory agent; and
   c) optionally, an antigen,
wherein the composition is formulated in electrosprayed microparticles.

2. The method according to claim 1, further comprising administering an antibody to the subject.

* * * * *

UNITED STATES PATENT AND TRADEMARK OFFICE
CERTIFICATE OF CORRECTION

PATENT NO. : 11,052,149 B2  
APPLICATION NO. : 16/334153  
DATED : July 6, 2021  
INVENTOR(S) : Ting et al.

Page 1 of 1

It is certified that error appears in the above-identified patent and that said Letters Patent is hereby corrected as shown below:

In the Specification

Column 4, Line 24: Please correct "10 g/mL" to read -- 10 µg/mL --

Column 4, Lines 48-49: Please correct "$CD^{4+}$ and $CD^{8+}$" to read -- $CD4^+$ and $CD8^+$ --

Column 4, Line 56: Please correct "0.2 gig" to read -- 0.2 µg --

Column 6, Line 5: Please correct "IFN-3" to read -- IFN-β --

Column 6, Line 41: Please insert a paragraph break in between "(n=5+SD)" and "FIG. 20."

Column 6, Line 41: Please correct "(n=5+SD)" to read -- (n=5±SD) --

Column 18, Line 31: Please correct "I(MSP1)" to read -- 1(MSP1) --

Column 18, Line 48: Please correct "E1 to E21" to read -- E11 to E21 --

Column 19, Line 63: Please correct "N-glycinyl" to read -- N1-glycinyl --

Column 29, Line 34: Please correct "1B kinase" to read -- IκB kinase --

Column 31, Line 50: Please correct "0.2 fig" to read -- 0.2 µg --

Column 43, Line 23: Please correct "116" to read -- Il6 --

Signed and Sealed this  
Twenty-third Day of November, 2021

Drew Hirshfeld  
*Performing the Functions and Duties of the  
Under Secretary of Commerce for Intellectual Property and  
Director of the United States Patent and Trademark Office*